(12) United States Patent
Dann et al.

(10) Patent No.: US 8,118,774 B2
(45) Date of Patent: Feb. 21, 2012

(54) TOPOSCOPIC ACCESS AND DELIVERY DEVICES

(75) Inventors: Mitchell Dann, Wilson, WY (US); Greg Fluet, Jackson, WY (US); James Wright, Carpinteria, CA (US)

(73) Assignee: ValenTx, Inc., Carpinteria, CA (US)

( * ) Notice: Subject to any disclaimer, the term of this patent is extended or adjusted under 35 U.S.C. 154(b) by 0 days.

(21) Appl. No.: 11/861,156

(22) Filed: Sep. 25, 2007

(65) Prior Publication Data

US 2008/0167606 A1    Jul. 10, 2008

Related U.S. Application Data

(60) Provisional application No. 60/826,862, filed on Sep. 25, 2006.

(51) Int. Cl.
*A61M 31/00*    (2006.01)
(52) U.S. Cl. .................................... 604/95.04
(58) Field of Classification Search ............ 604/93.01, 604/95.04, 104, 123, 198, 42
See application file for complete search history.

(56) References Cited

U.S. PATENT DOCUMENTS

| | | |
|---|---|---|
| 3,589,356 A | 6/1971 | Silverman |
| 3,982,554 A | 9/1976 | Saito et al. |
| 4,043,345 A | 8/1977 | Kramann et al. |
| 4,109,659 A | 8/1978 | Sheridan |
| 4,134,405 A | 1/1979 | Smit |
| 4,217,664 A | 8/1980 | Faso |
| 4,252,131 A | 2/1981 | Hon et al. |
| 4,271,839 A | 6/1981 | Fogarty et al. |
| 4,315,509 A | 2/1982 | Smit |
| 4,329,995 A | 5/1982 | Anthracite |
| 4,501,264 A | 2/1985 | Rockey |
| 4,606,347 A | 8/1986 | Fogarty et al. |
| 4,630,609 A | 12/1986 | Chin |
| 4,641,653 A | 2/1987 | Rockey |
| 4,719,916 A | 1/1988 | Ravo |
| 4,763,653 A | 8/1988 | Rockey |

(Continued)

FOREIGN PATENT DOCUMENTS

WO    WO 98/56440 A1    12/1998

OTHER PUBLICATIONS

International Preliminary Report on Patentability, PCT/US2007/079460 issued Mar. 31, 2009.

(Continued)

*Primary Examiner* — Nicholas Lucchesi
*Assistant Examiner* — Diva Ranade
(74) *Attorney, Agent, or Firm* — Knobbe, Martens, Olson & Bear LLP

(57) ABSTRACT

Disclosed herein are elongate flexible medical devices which are capable of axial elongation through the mechanism of eversion or toposcopic expansion. In general, this may be accomplished by providing a flexible tubular device having a proximal end and a distal end. Retraction of the distal end in a proximal direction through the tubular body inverts the tube upon itself, causing an axial shortening of the overall length of the device. The original length of the device can be restored by coupling a pressurized media to the proximal end of the sleeve. If the distal end of the sleeve is temporarily restricted or closed, the pressurized media causes the distal end of the sleeve to travel distally until the full length of the sleeve has been restored.

13 Claims, 36 Drawing Sheets

U.S. PATENT DOCUMENTS

| | | | |
|---|---|---|---|
| 4,863,440 A | 9/1989 | Chin | |
| 4,905,693 A | 3/1990 | Ravo | |
| 4,946,440 A | 8/1990 | Hall | |
| 5,171,305 A | 12/1992 | Schickling et al. | |
| 5,236,423 A | 8/1993 | Mix et al. | |
| 5,306,300 A | 4/1994 | Berry | |
| 5,458,573 A | 10/1995 | Summers | |
| 5,676,688 A | 10/1997 | Jaker et al. | |
| 5,785,684 A | 7/1998 | Zimmon | |
| 5,820,584 A | 10/1998 | Crabb | |
| 6,254,642 B1 | 7/2001 | Taylor | |
| 6,338,345 B1 | 1/2002 | Johnson et al. | |
| 6,544,291 B2 | 4/2003 | Taylor | |
| 6,558,429 B2 | 5/2003 | Taylor | |
| 6,675,809 B2 | 1/2004 | Stack et al. | |
| 6,702,735 B2 | 3/2004 | Kelly | |
| 6,740,121 B2 | 5/2004 | Geitz | |
| 6,746,489 B2 | 6/2004 | Dua et al. | |
| 6,845,776 B2 | 1/2005 | Stack et al. | |
| 6,946,002 B2 | 9/2005 | Geitz | |
| 6,994,095 B2 | 2/2006 | Burnett et al. | |
| 7,025,791 B2 | 4/2006 | Levine et al. | |
| 7,037,344 B2 | 5/2006 | Kagan et al. | |
| 7,083,629 B2 | 8/2006 | Weller et al. | |
| 7,097,665 B2 | 8/2006 | Stack et al. | |
| 7,111,627 B2 | 9/2006 | Stack et al. | |
| 7,121,283 B2 | 10/2006 | Stack et al. | |
| 7,122,058 B2 | 10/2006 | Levine et al. | |
| 7,146,984 B2 | 12/2006 | Stack et al. | |
| 7,152,607 B2 | 12/2006 | Stack et al. | |
| RE39,533 E * | 3/2007 | Ranoux | 600/34 |
| 7,211,114 B2 | 5/2007 | Bessler | |
| 7,220,237 B2 | 5/2007 | Gannoe et al. | |
| 7,220,284 B2 | 5/2007 | Kagan et al. | |
| 7,229,428 B2 | 6/2007 | Gannoe et al. | |
| 7,244,270 B2 * | 7/2007 | Lesh | 623/1.11 |
| 7,267,694 B2 | 9/2007 | Levine et al. | |
| 7,288,101 B2 | 10/2007 | Deem et al. | |
| 7,314,489 B2 | 1/2008 | McKenna et al. | |
| 7,316,716 B2 | 1/2008 | Egan | |
| 7,329,285 B2 | 2/2008 | Levine et al. | |
| 7,338,505 B2 | 3/2008 | Belson | |
| 7,347,875 B2 | 3/2008 | Levine et al. | |
| 7,354,454 B2 | 4/2008 | Stack et al. | |
| 7,431,725 B2 | 10/2008 | Stack et al. | |
| 7,468,060 B2 | 12/2008 | Utley et al. | |
| 7,476,256 B2 | 1/2009 | Meade et al. | |
| 7,483,754 B2 | 1/2009 | Imran et al. | |
| 7,520,874 B2 | 4/2009 | Koyama et al. | |
| 2001/0044595 A1 | 11/2001 | Reydel et al. | |
| 2002/0016607 A1 | 2/2002 | Bonadio et al. | |
| 2002/0058960 A1 * | 5/2002 | Hudson et al. | 606/192 |
| 2003/0199990 A1 | 10/2003 | Stack et al. | |
| 2003/0199991 A1 | 10/2003 | Stack et al. | |
| 2004/0092892 A1 | 5/2004 | Kagan et al. | |
| 2004/0093065 A1 | 5/2004 | Yachia et al. | |
| 2004/0102855 A1 | 5/2004 | Shank | |
| 2004/0117031 A1 | 6/2004 | Stack et al. | |
| 2004/0133147 A1 | 7/2004 | Woo | |
| 2004/0138529 A1 | 7/2004 | Wiltshire et al. | |
| 2004/0138761 A1 | 7/2004 | Stack et al. | |
| 2004/0143342 A1 | 7/2004 | Stack et al. | |
| 2004/0181242 A1 | 9/2004 | Stack et al. | |
| 2004/0186514 A1 | 9/2004 | Swain et al. | |
| 2004/0220682 A1 | 11/2004 | Levine et al. | |
| 2004/0243152 A1 | 12/2004 | Taylor et al. | |
| 2004/0249362 A1 | 12/2004 | Levine et al. | |
| 2005/0033331 A1 | 2/2005 | Burnett et al. | |
| 2005/0049718 A1 * | 3/2005 | Dann et al. | 623/23.65 |
| 2005/0080431 A1 | 4/2005 | Levine et al. | |
| 2005/0085787 A1 | 4/2005 | Laufer | |
| 2005/0085900 A1 * | 4/2005 | Case et al. | 623/1.24 |
| 2005/0096750 A1 | 5/2005 | Kagan et al. | |
| 2005/0101977 A1 | 5/2005 | Gannoe | |
| 2005/0125020 A1 | 6/2005 | Meade et al. | |
| 2005/0177181 A1 * | 8/2005 | Kagan et al. | 606/151 |
| 2005/0197714 A1 | 9/2005 | Sayet | |
| 2005/0222592 A1 | 10/2005 | Gannoe et al. | |
| 2005/0228504 A1 | 10/2005 | Demerais | |
| 2005/0240279 A1 * | 10/2005 | Kagan et al. | 623/23.65 |
| 2005/0247320 A1 | 11/2005 | Stack et al. | |
| 2005/0261549 A1 | 11/2005 | Hewit et al. | |
| 2005/0267499 A1 | 12/2005 | Stack et al. | |
| 2006/0009858 A1 | 1/2006 | Levine et al. | |
| 2006/0015125 A1 | 1/2006 | Swain | |
| 2006/0020164 A1 | 1/2006 | Butler et al. | |
| 2006/0020247 A1 | 1/2006 | Kagan et al. | |
| 2006/0020254 A1 | 1/2006 | von Hoffmann | |
| 2006/0020278 A1 | 1/2006 | Burnett et al. | |
| 2006/0155312 A1 | 7/2006 | Levine et al. | |
| 2006/0155375 A1 * | 7/2006 | Kagan et al. | 623/11.11 |
| 2006/0161139 A1 | 7/2006 | Levine et al. | |
| 2006/0161172 A1 | 7/2006 | Levine et al. | |
| 2006/0161187 A1 | 7/2006 | Levine et al. | |
| 2006/0161265 A1 | 7/2006 | Levine et al. | |
| 2006/0173422 A1 * | 8/2006 | Reydel et al. | 604/271 |
| 2006/0206063 A1 * | 9/2006 | Kagan et al. | 604/264 |
| 2006/0206064 A1 * | 9/2006 | Kagan et al. | 604/264 |
| 2006/0265082 A1 * | 11/2006 | Meade et al. | 623/23.65 |
| 2006/0287734 A1 | 12/2006 | Stack et al. | |
| 2006/0293742 A1 | 12/2006 | Dann et al. | |
| 2007/0005147 A1 | 1/2007 | Levine et al. | |
| 2007/0010794 A1 | 1/2007 | Dann et al. | |
| 2007/0010864 A1 | 1/2007 | Dann et al. | |
| 2007/0010865 A1 | 1/2007 | Dann et al. | |
| 2007/0010866 A1 | 1/2007 | Dann et al. | |
| 2007/0016244 A1 * | 1/2007 | Behl et al. | 606/200 |
| 2007/0027548 A1 | 2/2007 | Levine et al. | |
| 2007/0032879 A1 | 2/2007 | Levine et al. | |
| 2007/0083271 A1 | 4/2007 | Levine et al. | |
| 2007/0106233 A1 * | 5/2007 | Huang et al. | 604/271 |
| 2007/0129719 A1 * | 6/2007 | Kendale et al. | 606/41 |
| 2007/0156248 A1 | 7/2007 | Marco et al. | |
| 2007/0198074 A1 | 8/2007 | Dann et al. | |
| 2007/0225555 A1 | 9/2007 | Stefanchik | |
| 2007/0233162 A1 | 10/2007 | Gannoe et al. | |
| 2007/0293885 A1 | 12/2007 | Binmoeller | |
| 2008/0004606 A1 | 1/2008 | Swain et al. | |
| 2008/0033574 A1 | 2/2008 | Bessler et al. | |
| 2008/0058887 A1 | 3/2008 | Griffin et al. | |
| 2008/0103604 A1 | 5/2008 | Levine et al. | |
| 2008/0167606 A1 | 7/2008 | Dann et al. | |
| 2008/0167629 A1 | 7/2008 | Dann et al. | |
| 2008/0195226 A1 | 8/2008 | Williams et al. | |
| 2008/0208355 A1 | 8/2008 | Stack et al. | |
| 2008/0208356 A1 | 8/2008 | Stack et al. | |
| 2008/0208357 A1 | 8/2008 | Melanson et al. | |
| 2008/0221597 A1 | 9/2008 | Wallace et al. | |
| 2008/0249533 A1 | 10/2008 | Godin | |
| 2008/0255587 A1 | 10/2008 | Cully et al. | |
| 2008/0255594 A1 | 10/2008 | Cully et al. | |
| 2008/0255678 A1 | 10/2008 | Cully et al. | |
| 2008/0269797 A1 | 10/2008 | Stack et al. | |
| 2009/0012356 A1 | 1/2009 | Dann et al. | |
| 2009/0012541 A1 | 1/2009 | Dahl et al. | |
| 2009/0012544 A1 | 1/2009 | Thompson et al. | |
| 2009/0012553 A1 | 1/2009 | Swain et al. | |

OTHER PUBLICATIONS

U.S. Appl. No. 11/431,040, filed May 9, 2006, Kagan et al.
Office Action for U.S. Appl. No. 11/861,172 mailed Nov. 10, 2008.
Office Action for U.S. Appl. No. 11/861,172 mailed Jul. 14, 2009.
Endoscopic suturing, C. Paul Swain MD, *Balliere's Clinical Gastroenterology*, vol. 13, No. 1, pp. 97-108, 1999.
Progression rate of self-propelled feeding tubes in critically ill patients, Mette M. Berger et al., *Intensive Care Med* Oct. 29, 2002, pp. 1768-1774.
Iatrogenic Intussusception: a Complication of Long Intestinal Tubes, Patricia Redmond, M.D., et al., *American Jounal of Gastroenterology*, vol. 77, No. 1, 1982, pp. 39-42.
Design and Testing of a New, Small Diameter, Single Stitch Endoscopic Sewing Machine, C.P. Swain et al., *Abstracts Submitted to A/S/G/E/ 1990*, Vo. 36, No. 2, 1990, pp. 213, 214.
An endoscopic stapling device: the development of new flexible endoscopically controlled device for placing multiple transmural staples in gastrointestinal tissue, C. Paul Swain, MD et al., *Gastrointestinal Endoscopy*, vol. 35, No. 4, 1989 pp. 338-339.

An endoscopically deliverable tissue-transfixing device for securing biosensors in the gastrointestinal tract, C. Paul Swain, MD et al. *Gastrointestinal Endoscopy*, 1994 vol. 40 No. 6 pp. 730-734.

Synthetic Biodegradable Polymers as Medical Devices, John C. Middleton et al., *Medical Plastics and Biomaterials Magazine MPS Article Index*, Mar. 1998.

*Experimental study on in situ tissue engineering of the stomach by an acellular collagen sponge scaffold graft*, Hori Y. Nakamura et al., Abstract, May 2001.

*Repair of Full-Thickness Defects in Alimentary Tract Wall with Patches of Expanded Polytetrafluoroethylene*, Daniel S. Oh, MD et al., Annals of Surgery 2002; 235:708-712.

*Stents in the small intestine*, Singh S, Gagneja HK, Abstract, Oct. 2002.

*Evaluation of porcine-derived small intestine submucosa as a biodegradable graft for gastrointestinal healing*, SG del la Fuente et al., Abstract, J. Gastrointest Surg Jan. 2003.

Bard EndoCinch: the device, the technique and pre-clinical studies, Paul Swain, M.D. et al., *Gastrointestinal Endoscopy Clinics of North America*, 13, 2003 pp. 75-88.

Effect of Duodenal-Jejunal Exclusion of a Non-obese Animal Model of Type 2 Diabetes, Francesco Rubino, MD et al., *Annals of Surgery*, vol. 239, No. 1, Jan. 2004, pp. 1-11.

*The LAP-BAND Solution*, BioEnterics Corporation, Brochure, http://www.bioenterics.com/.

*Obesity Treatment*, Medical Innovation Development, Brochure.

*The Remote Controlled Swedish Band, The method of choice in modern treatment of morbid obesity*, Obtech Medical AG, Brochure.

*The Bard EndoCinch Procedure*, Introducing Endoscopic Technology for the Treatment of GERD.

*Microvasive WALLSTENT® Colonic and Duodenal Endoprosthesis*, Boston Scientific website, www.bostonscientific.com, Sep. 20, 2002.

*Bioabsorable Polymers*, William B. Gleason, University of Minnesota, 1998.

Three-dimensional manometric imaging of the lower esophageal sphincter, Hubert J. Stein, Md. *Surgery*, 1995 vol. 117 No. 6 pp. 692-698.

A new method of enteroscopy—The double-balloon method, Yamamoto et al., *Can J. Gastroenterol*, vol. 17, No. 4 Apr. 2003, pp. 273-274.

Radiocontrolled Movement of a Robot Endoscope in the Human Gastrointestinal Tract, Paul Swain et al., Abstract—*Gastrointestinal Endoscopy*, vol. 61, No. 5 DDW Abstract Issue: Apr. 2005.

Techniques for Advancing Guide Wires and Devices in the Lumen of the Gastrointestinal Tract, Long et al., *Gastrointestial Endoscopy*, vol. 57, No. 5 Apr. 2003 Abstract, 2003 ASGE Meeting, May 18-21, Orlando Florida.

\* cited by examiner

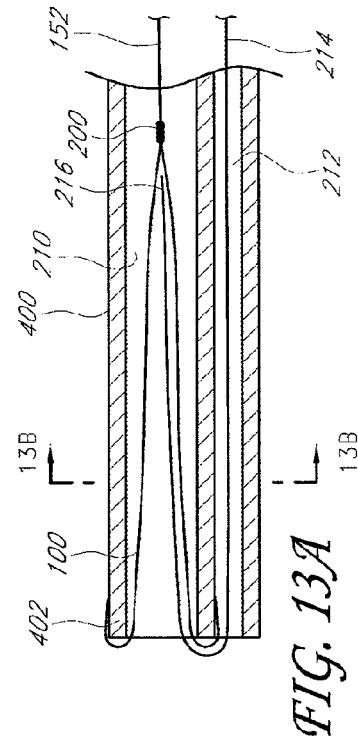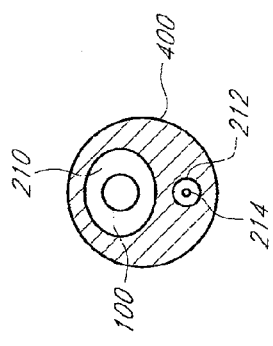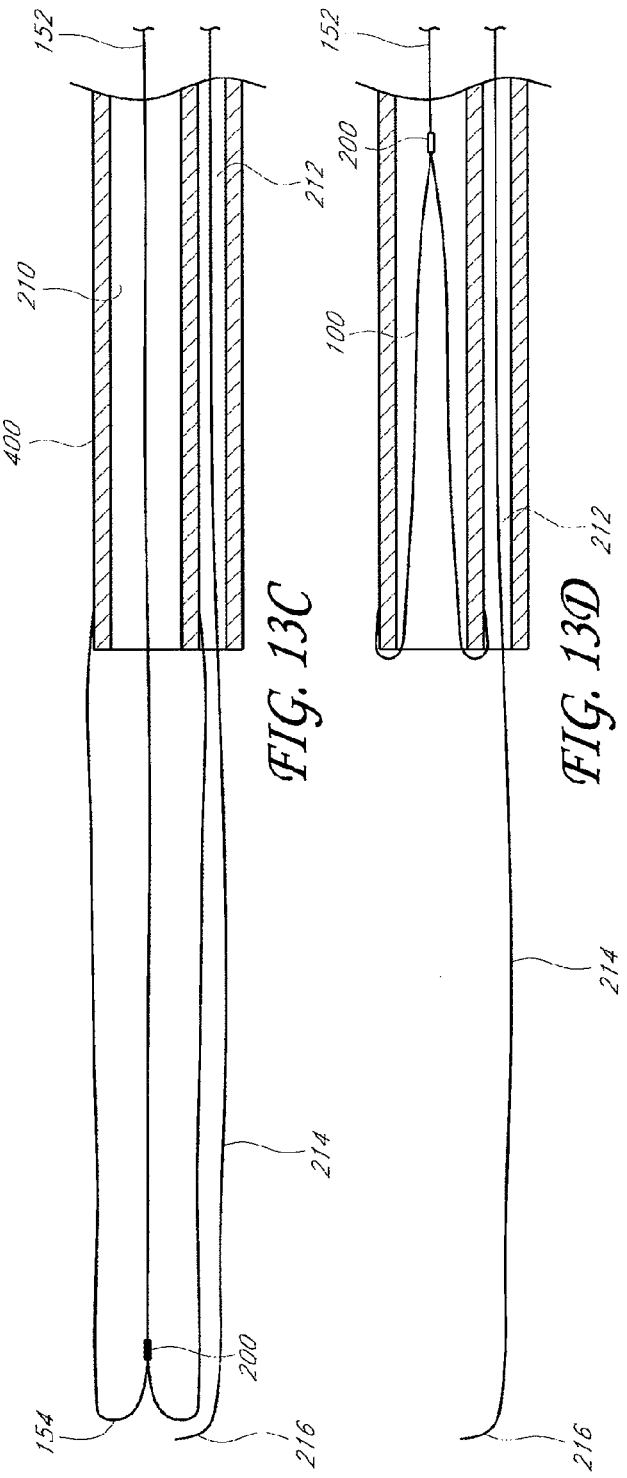
FIG. 13A
FIG. 13B
FIG. 13C
FIG. 13D

TOPOSCOPIC ACCESS AND DELIVERY DEVICES

This application claims priority under 35 U.S.C. §119(e) to U.S. Provisional Application No. 60/826,862 filed Sep. 25, 2006, which is hereby incorporated by reference in its entirety.

U.S. patent application Ser. No. 10/698,148, filed Oct. 31, 2003, published May 13, 2004 as U.S. Patent Pub. No. 2004-0092892 A1 and entitled "APPARATUS AND METHODS FOR TREATMENT OF MORBID OBESITY" (and may be referred to herein as the "Kagan '148 application"); U.S. patent application Ser. No. 11/025,364, filed Dec. 29, 2004, published Aug. 11, 2005 as U.S. Patent Pub. No. 2005-0177181 A1 and entitled "DEVICES AND METHODS FOR TREATING MORBID OBESITY" (and may be referred to herein as the "Kagan '181 application"); U.S. patent application Ser. No. 11/124,634, filed May 5, 2005, published Jan. 26, 2006 as U.S. Patent Pub. No. 2006-0020247 A1 and entitled "DEVICES AND METHODS FOR ATTACHMENT OF AN ENDOLUMENAL GASTROINTESTINAL IMPLANT" (and may be referred to herein as the "Kagan '634 application"); U.S. patent application Ser. No. 11/400,724, filed Apr. 7, 2006, published Jan. 11, 2007 as U.S. Patent Pub. No. 2007-0010794 A1 and entitled "DEVICES AND METHODS FOR ENDOLUMENAL GASTROINTESTINAL BYPASS" (and may be referred to herein as the "Dann '724 application"); and U.S. patent application Ser. No. 11/548,605, filed Oct. 11, 2006, entitled "DEVICES AND METHODS FOR ENDOLUMENAL GASTROINTESTINAL BYPASS" (and may be referred to herein as the "Dann '605 application") are hereby incorporated by reference in their entireties herein, as well as any additional applications, patents, or publications noted in the specification below.

BACKGROUND OF THE INVENTION

A wide variety of medical procedures involve the introduction of catheters, endoscopes, and other devices through natural lumen and artificially created passageways in the body. Certain applications require creating a device path through a sphincter or narrow body lumen, or through a long, tortuous pathway. Conventional distal axial advance (i.e., pushing) of a device is sometimes unable to reach a desired treatment or diagnostic site, and may in any event cause discomfort to the patient or trauma to delicate or sensitive tissues as the device is being advanced.

Lubricants and lubricious polymers or other coatings can reduce these effects, but not always to a sufficient degree. In the biliary system, as one example, passing a biliary catheter through the ampulla of Vater and into the common bile duct often results in swelling and subsequent closure of the opening, compromising normal drainage and making subsequent access difficult. Similar problems with discomfort or edema or failure to achieve proper device placement can be experienced by the patients when other anatomical sites are being accessed, for example, in the nasal passages, urethra, small intestine, colon, rectum, etc. While patient comfort may not be an issue when navigating internally such as within the biliary tree, the introduced device may be difficult or even impossible to advance as a result of frictional forces acting against it, especially since these obstructions and narrowed passages often cannot be adequately visualized.

Besides the biliary system, a variety of other sites within the body present an opportunity for improved access, patient comfort and reduced trauma during the introduction of a device. For example, the nasal passages are especially sensitive and recent trends have brought about an increase in the number of devices, such as endoscopes and tubes, being introduced via that route concomitant with the use of analgesics or sedatives to reduce patient discomfort.

Another setting where improved access would be important is for any of a variety of diagnostic or therapeutic procedures in the lower gastrointestinal tract. Accessing the small intestines is a significant challenge with current endoscopic technologies. The intestines are substantially unconstrained, mobile and follow a tortuous path so it is difficult to advance a pushable device through the intestinal lumen. Using an enteroscope to access the intestines can often provide access to the proximal region and the newer double balloon enteroscopes can access more distally by using the two balloons to push and pull against the wall of the intestines. However, both methods rely on applying a pushing force on the device or using the device to apply force against the walls of the intestine to advance the devices. Using a device as described herein would enable deployment of a device throughout the small intestine with less force acting on the intestine. The device as described could be used as a guide conduit for advancing an enteroscope or other device or it could deploy a guide wire or deliver therapeutic or diagnostic devices to affect treatment of the small intestine.

Therefore, what is needed is a medical device introducer system that can be incorporated into or used with a variety of catheter(s), sheath(s), endoscope(s) or other medical devices to permit the safe and comfortable passageway into and/or through a bodily passage to a remote procedure site.

SUMMARY OF THE INVENTION

In one embodiment, disclosed is a toposcopic deployment system that includes a filling catheter, a sleeve configured to be delivered within a body lumen, and a grasping member configured to be attached to the sleeve and mechanically promote eversion of the sleeve. The sleeve is at least partially inverted within the filling catheter. In some embodiments, the system includes a pump for infusing inflation media to the filling catheter. The system can also include a source of filling media. The grasping member may include a loop snare. The sleeve may include a plurality of tail elements, such as, for example, three tail elements spaced substantially equidistant with respect to the circumference of a lumen of the sleeve. The filling catheter may be a pushable tube. The filling catheter may be collapsible in some embodiments, or alternatively semi-rigid. The delivery system may include at least one pull wire operably attached to the filling catheter to steer the filling catheter within a body lumen. The system may include, in some embodiments, a guidewire and/or an overtube. The sleeve may be biodegradable. The system may also include a diagnostic or therapeutic device operably connected to the sleeve selected from the group consisting of: endoscopes, guidewires, catheters, tubular bypass conduits, drugs, adhesives, radiopaque contrast media, cameras, lasers, ultrasound transducers, electrodes, LEDs, cryogenic energy sources, balloons, forceps, graspers, electrosurgical instruments, snares, biopsy devices, needles, guidewires and rail systems.

In another embodiment, also disclosed herein is a method of toposcopically delivering a sleeve to a body lumen, according to some embodiments of the invention. The method includes the steps of providing the sleeve at least partially inverted within a filling catheter, the sleeve comprising a proximal end, a distal end, and an elongate body, the proximal end of the sleeve attached to a distal end of the filling catheter; advancing the sleeve and the filling catheter to position the distal end of the filling catheter at a first point in the body lumen; and flowing inflation media within the sleeve to promote eversion of the sleeve to a second point in the body lumen. The body lumen can be the gastrointestinal tract. The method can also include the step of at least partially inverting the sleeve within the filling catheter. In some embodiments, the method also includes the step of sealing the distal end of the sleeve. Sealing the distal end of the sleeve may include attaching a grasping member to the distal end of the inverted sleeve. The method may also include the step of actuating the grasping member distally to promote eversion of the sleeve. The grasping member can be a loop snare. In some embodiments, the distal end of the inverted sleeve includes a plurality of tail elements. In some embodiments, flowing the inflation media within the sleeve to evert the sleeve is accomplished at a pressure of less than about 3 psi. In some embodiments, the method further includes steering the filling catheter within the body lumen using one or more pull wires operably attached to the filling catheter.

In some embodiments, also disclosed herein is a method of delivering a sleeve to a body lumen, including the steps of providing a sleeve configured to be delivered within a body lumen, the sleeve having an axially compressed configuration for delivery to a body lumen and an axially elongate configuration after the sleeve is delivered, wherein at least a portion of the sleeve has accordion-like features; operably connecting the sleeve to a filling catheter in the sleeve's axially compressed configuration; and flowing inflation media within the sleeve to promote transformation of the sleeve from the axially compressed configuration to an axially elongate configuration.

In some embodiments, disclosed is a toposcopic delivery system including a filling catheter and a sleeve configured to be delivered within a body lumen, the sleeve having an axially compressed configuration for delivery to a body lumen and an axially elongate configuration after the sleeve is delivered. The length of the sleeve in its axially elongate configuration can be at least about 100% longer than a length of the sleeve in its axially compressed configuration. In some embodiments, the sleeve includes a portion with accordion-like features.

BRIEF DESCRIPTION OF THE DRAWINGS

FIG. 13A-13D schematically illustrate an alternative toposcopic guidewire delivery system in accordance with the present invention.

DETAILED DESCRIPTION OF THE PREFERRED EMBODIMENTS

Figure 1A:
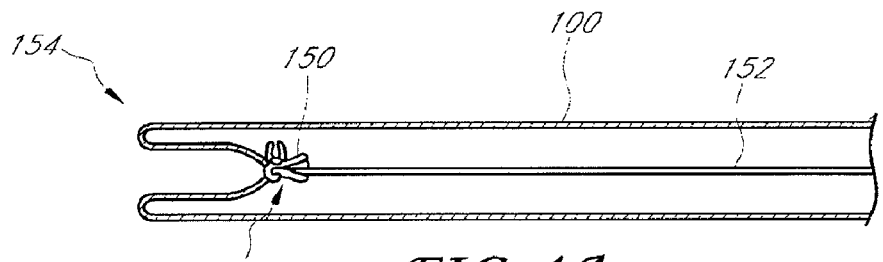
FIG. 1A is a schematic cross-sectional view of a toposcopic sleeve partially inverted within itself.

The present invention relates to elongate flexible medical devices which are capable of axial elongation through the mechanism of eversion or toposcopic expansion. In general, this may be accomplished by providing a flexible tubular device having a proximal end and a distal end. Retraction of the distal end in a proximal direction through the tubular body inverts the tube upon itself, causing an axial shortening of the overall length of the device. The original length of the device can be restored by coupling a pressurized media to the proximal end of the sleeve. If the distal end of the sleeve is temporarily restricted or closed, the pressurized media causes the distal end of the sleeve to travel distally until the full length of the sleeve has been restored. The general topic of toposcopic deployment is understood in the art.

In general, the toposcopic devices in accordance with the present invention may be utilized for any of a variety of purposes, some of which are exemplified below. For example, the toposcopic sleeve may be utilized as a conduit for enabling the introduction of any of a variety of diagnostic or therapeutic devices. These include endoscopes, guidewires, catheters, tubular bypass conduits, drugs, adhesives, radiopaque contrast media, cameras, lasers, ultrasound transducers, electrodes, LEDs or other light sources, cryogenic energy sources, balloons, forceps, graspers, electrosurgical instruments, snares, biopsy devices, needles, guidewires and rail or other guidance systems for guiding additional instrumentation.

In one embodiment of the current invention, a delivery device is used to advance the distal end of an inverted sleeve to a desired deployment site in a lumen. The delivery device may be a pushable filling catheter itself or a secondary device that is used to advance a non-pushable filling catheter. Examples of a separate delivery device used to advance the distal end of the inverted sleeve include a pediatric colonoscope, enteroscope, endoscope, duodenoscope, or a simple pushable rod or catheter that can be attached to the filling catheter. Once at the desired deployment site, for example, past the pylorus, a fluid, either compressible or non-compressible, is delivered into the filling catheter to deploy the toposcopic element. U.S. Application 2001/0044595A1 filed May 2, 2001, entitled Introducer Apparatus with Eversible Sleeve, the disclosure of which is incorporated in its entirety herein by reference, describes a pushable catheter with an everting distal end used to access the small intestines, however in this device the medium that is advanced to deploy the everting section is a solid inner member.

In addition, although the toposcopic sleeve will be disclosed below primarily in the context of a gastrointestinal access device or gastrointestinal implant, devices in accordance with the present invention may be utilized to access any of a wide variety of natural lumen, hollow organs, or artificially created tissue tracts throughout the body. The length, diameter, wall thicknesses, construction of the filling tube and other features disclosed below may be modified to suit the intended target or access pathway as will be apparent by those of skill in the art in view of the disclosure herein.

For example, in the gastrointestinal system, the toposcopic sleeve may be utilized to access the esophagus, lower esophagus, gastroesophageal junction, stomach, the pylorus, biliary ducts, the gallbladder, the small intestine, the appendix, the caecum, the large intestine, the anus, or other locations in between. Toposcopic devices in accordance with the present invention may also be utilized throughout the cardiovascular system, as well as the airways including the trachea and bronchial tree.

From a procedure standpoint, the toposcopic sleeves of the present invention may be utilized to deliver devices or otherwise assist with ERCP, nasal gastric tube delivery, diagnosis and treatment of intestinal bleeding, using electro coagulation or other technique, treating ulcers, remove polyps, intestinal biopsy, stent deployment, dilatation of strictures, tagging or marking areas for subsequent surgeries such as treatment sites within the intestine, creating a sterile conduit for accessing a treatment site, any of a wide variety of endoscopic and transgastric procedures, stomach pumping, tracheostomy tube delivery and bronchoscopy. Potential procedures also include biopsy of any of a variety of organs such as liver biopsy, removal of any of a variety of organs or tumors such as appendectomy, and localized delivery of pharmaceutical agents or biologically active agents to a treatment site.

In addition to utilizing the everting tubes of the present invention to access a wide variety of sites to accomplish any of a variety of procedures, the toposcopic delivery sleeve may also be utilized as a transport vehicle to carry wires or secondary devices to the treatment site. This may be accomplished by attaching the distal end of the tube to a device or guide, and everting the tube thereby carrying the device or guide in a distal direction for placement in the patient. Any of a wide variety of diagnostic or therapeutic devices may be carried to a remote site, such as radiofrequency diagnostic or therapeutic devices, diagnostic or therapeutic ultrasound, EM, piezoelectric pressure sensors, micro fluidic sensors, endoscopes, such as capsule endoscopes, and the like. The everting tube may also be utilized to deliver guidewires, catheters, tethers, rail systems or NG tubes to the desired site or the everting tube itself may serve as a guide conduit or overtube for other devices. In the example of a guidewire, the wire could be delivered using one of the following examples. The guidewire can be attached to the distal end of the tube and reside in the delivery catheter before the everting tube is deployed. In this method, the everting process pulls the guidewire distally as the sleeve everts. In another embodiment, the wire can reside along the outer surface of the everting tube before deployment, the wire making a 180° bend around the inverted radius of the sleeve and being attached or placed at or near the distal end of the sleeve. In this way it is always along what will be the outer diameter of the sleeve after deployment. The more proximal section of the guidewire in this embodiment could be held by a lumen alongside the OD of the filling catheter or a series of eyelets or clasps. In this method, as the sleeve is deployed the distal radius of the sleeve as it transitions form inverted to everted lays the guidewire down between the sleeve and the body lumen in which it is being deployed. Once fully everted the guidewire would be deployed alongside the delivery device. If desired, the delivery device could then be re-inverted by a retrieval wire (or grasping element, such as a snare, described in more detail below) in the central lumen of the delivery device attached to the distal end of the everting section. Re-inverting of the delivery device would leave the guidewire in place and the filling catheter could be pulled out of the lumen over the wire. Partial re-inverting could also be utilized to expose various locations of the small intestine as needed during a procedure to enable better visualization with a scope, tissue biopsy, ablation, coagulation, drug delivery or whatever a procedure may require.

Certain exemplary applications of the present invention will be described below. Modifications to accomplish any of the preceding applications may be made by those of skill in the art in view of the disclosure herein.

In one implementation of the invention, an endolumenal bypass sleeve may be deployed within the intestine using a toposcopic, or everting technique. Additional details are disclosed in U.S. patent application Ser. No. 11/400,724 entitled Devices and Methods for Endolumenal Gastrointestinal Bypass, filed Apr. 7, 2006, the disclosure of which is incorporated herein in it entirety by reference. Pressurization may be accomplished by placing the proximal end of the axially inverted sleeve in communication with a source of inflation or everting media, such as a liquid or gas. Liquid such as water or saline may be preferred, and may additionally be provided with a radiopaque additive to permit real time fluoroscopic visualization of the progress of the deployment within the GI system. The use of lubricants is discussed below. Additional additives may also be provided, such as antibiotics, nutritional supplements or others as may be desired.

Figure 1B:
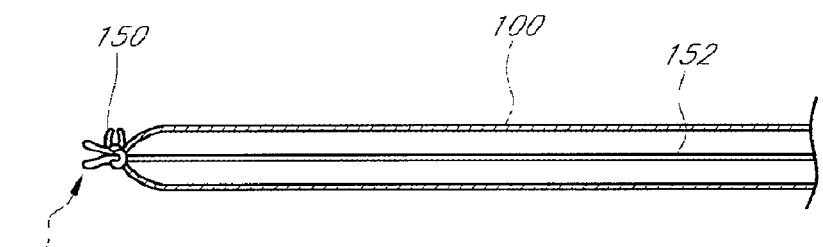
FIG. 1B is a schematic illustration as in FIG. 1A, with the toposcopic sleeve fully distally extended.

To maintain the internal fluid pressure used to assist in everting the inverted gastrointestinal sleeve, the distal end of the sleeve may be temporarily occluded or sealed during deployment. FIGS. 1A-1B illustrate one of a number of options for sealing the distal end 112 of a gastrointestinal sleeve 100 during delivery and deployment. FIG. 1A shows the distal end 112 of the gastrointestinal sleeve 100 inverted within the sleeve 100 and retracted a short distance in the proximal direction. The otherwise open distal end 112 is shown sealed with a suture or tie 150 which may be degradable and formulated to dissolve within a desired time such as no more than approximately 2 or 6 or 24 hours following deployment in the intestines. Dissolution of the biodegradable tie 150 can be aided by introduction of a solvent, or active agent, or inducing a pH change that is ingested or placed in the everting fluid. The distal end 112 may also be releasably secured to a pull line 152 such as a suture or wire, or a grasping member such as a snare, to assist in inverting the sleeve as will be apparent to those of skill in the art. Alternatively, the suture, wire, or grasper could be delivered by the sleeve and act as a guide wire for the placement of any of a number of other devices in the GI tract. FIG. 1B shows the noninverted (everted, or deployed) distal end 112 of the gastrointestinal sleeve 100 sealed with a biodegradable tie 150 that may be formulated to dissolve within the intestines.

Figure 1C:
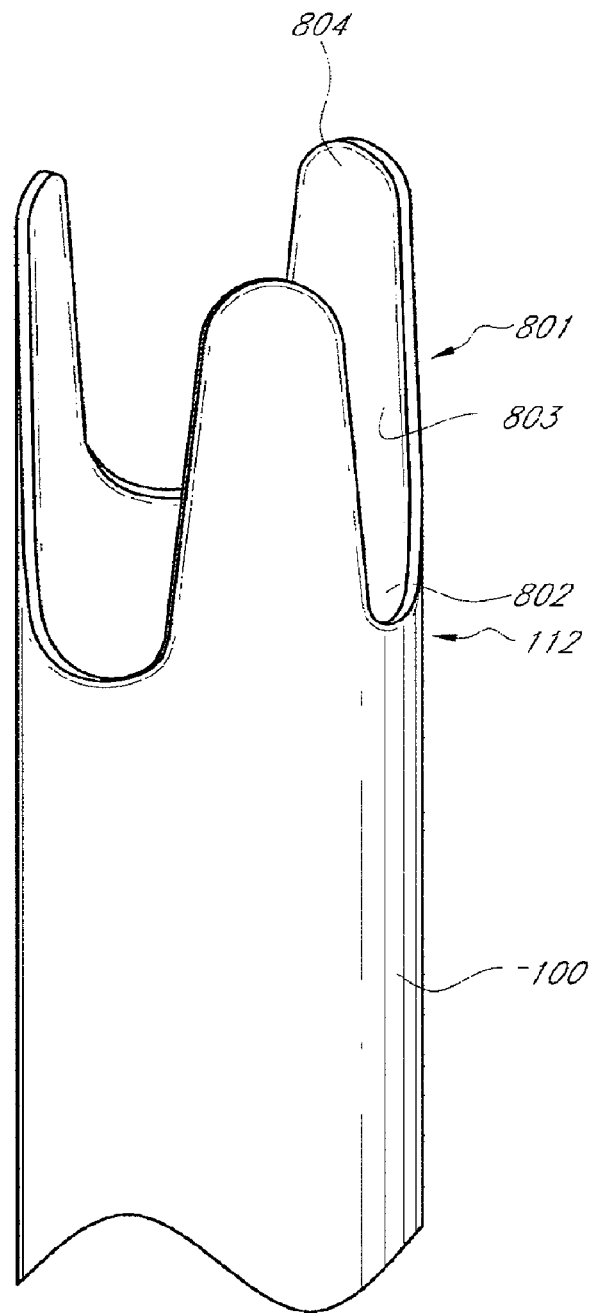
FIG. 1C is a schematic illustration of a sleeve with a plurality of distal elongate tail elements.

FIG. 1C illustrates an embodiment of a sleeve 100 with a plurality of elongate projections 801 (also referred to herein as tails) herein that can extend distally past the distal opening 112 of the sleeve 100. The tails 801 have a proximal end 802, an elongate body 803, and a distal end 804. The tails 801 can be integrally formed with the rest of the sleeve 100, or alternatively operably attached to the sleeve 100 by adhesive, bonding, annealing, suturing, or the like. The elongate tails 801 can advantageously be secured together at their distal ends 804 as shown below in FIGS. 14D-14F, such as with a tie, adhesive, or a grasping device, such as a snare (as will be described below). The tails 801 are preferably spaced substantially equally apart with respect to the circumference of the distal opening 112 of the sleeve 100, and sized to provide a consistent fluid-tight or near fluid-tight seal of the distal end 112 of the sleeve 100 as well as to promote substantially symmetric and predictable inversion and eversion of the sleeve 100 using inflation media. In one embodiment, the sleeve 100 includes 3 tail elements 801 spaced approximately 120 degrees apart with respect to the circumference of the distal opening 112 of the sleeve 100. In other embodiments, the sleeve 100 includes 2, 4, 5, 6, 7, 8, or more tails. In some embodiments, such as for a sleeve deployed into the intestine, the tails 801 are at least about 3 cm, 4 cm, 5 cm, 6 cm, 7 cm, 8 cm, 10 cm, or longer in length, and have a width of no more than about 1 cm, 2 cm, or 3 cm.

The distal end 112 of a sleeve may alternatively be temporarily occluded using adhesives, such as a water soluble adhesive or pressure sensitive adhesive applied to the interior surface of the distal end 112 of the sleeve. Alternatively, the distal end of the sleeve may be collapsed and folded over onto itself with or without the use of adhesives. Solvent bonding, thermal spot welding or other bonding technique may be used to close the distal end 112, in a manner that a slight increase in pressure can be applied to the inflation media following full deployment, to rupture the seal. A tie line may alternatively extend proximally from the distal end 112, either inside of the lumen or outside of the sleeve 100. Proximal retraction of the tie line following sleeve placement will untie a knot or otherwise release the distal end 112. Otherwise the distal end may be simply left open during the deployment process. Alternatively, the tie line may not release the end of the sleeve but could act as a retrieval line for re-inverting the sleeve back into the filling catheter if so desired.

Figure 2A:
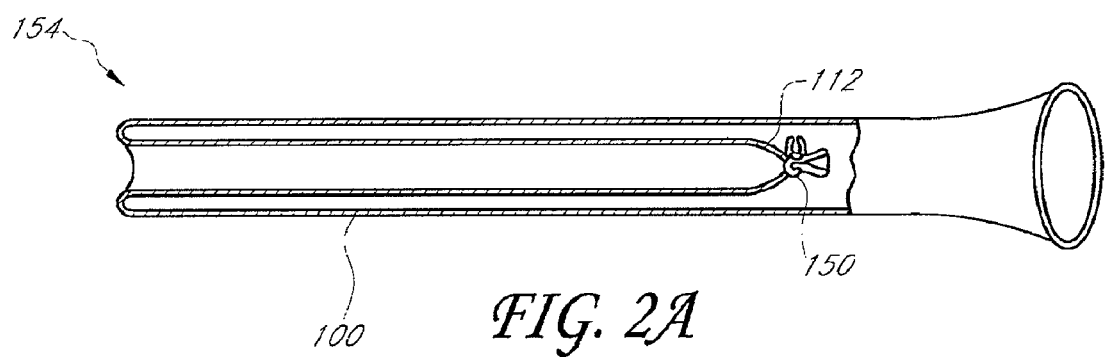
FIG. 2A is a schematic illustration as in FIG. 1A, with the toposcopic sleeve more fully inverted within itself.
Figure 2B:
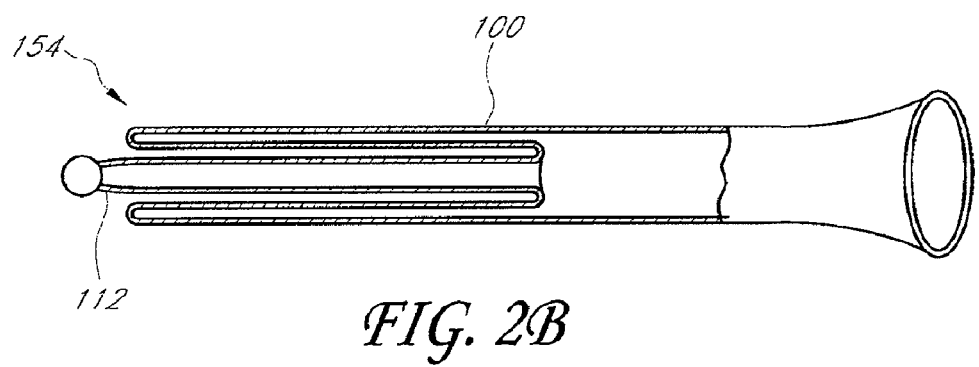
FIG. 2B is a schematic illustration as in FIG. 2A, with a double inversion of the toposcopic sleeve.

FIG. 2A shows a gastrointestinal sleeve 100 retracted proximally inside of itself in an inverted configuration. FIG. 2B shows a gastrointestinal sleeve 100 loaded in a double-inverted configuration. A full single inversion will reduce the length of the sleeve 100 by at least about 50%, while a full double inversion will reduce the length of the sleeve 100 to no more than about 25% of its original length. The sleeve can be inverted up to 100% with a single inversion by pulling the distal end 112 proximally of the proximal end of the sleeve, such as into a filling tube or other placement device.

Deployment of the sleeve may be accomplished by positioning the distal end 154 of the inverted sleeve 100 at a first position within the target lumen such as the GI tract, and then second everting the sleeve to position the everted distal end at a second position within the GI tract, downstream (from a device deployment perspective) from the first position. The second position will normally be at least about 50 cm and often at least about 75 cm or 100 cm or more distally of the pylorus. The second position could potentially be to anywhere in the small intestine, to the mecum, to the colon, or even all the way through the GI tract and out the anus. The first position where the distal end 154 of the inverted sleeve is placed may be at about the pylorus, within about 20 cm of the pylorus, or within about 50 cm of the pylorus, depending upon the device design and desired deployment procedure.

Inverting the sleeve simplifies the delivery and deployment of the device, but it adds some additional constraints to the configuration of the device. The inverting segments can have very thin walls and inverting interfaces can be highly lubricious for easy and reliable deployment. For example, blow molded 90A durometer polyurethane of a wall thickness on the order of 0.005" or less, preferably about 0.002", with a lubricious coating may work in this manner. Another example of a suitable material is PTFE. Eversion within the intestine may be accompanied by introduction of an irrigating or lubricating fluid on the outside of the sleeve 100, and/or provision of a lubricant in between contacting surfaces of the inverted sleeve. Additional details are disclosed in co-pending application Ser. No. 10/698,148, filed Oct. 31, 2003, entitled Apparatus and Methods for Treatment of Morbid Obesity, the disclosure of which is incorporated in its entirety herein by reference.

Figure 2C:
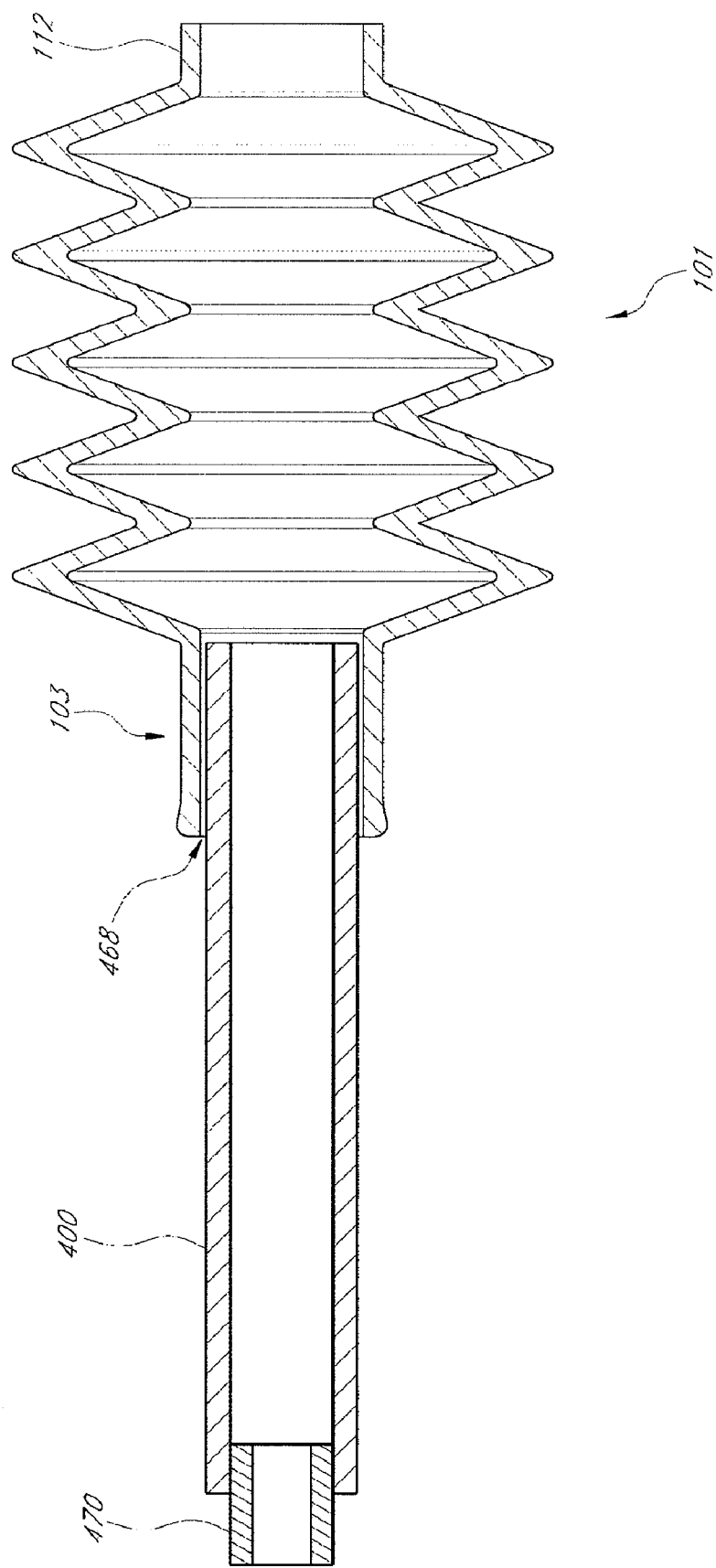
FIG. 2C is a schematic illustration of a sleeve with accordion-like features that can be axially expanded.
Figure 2D:
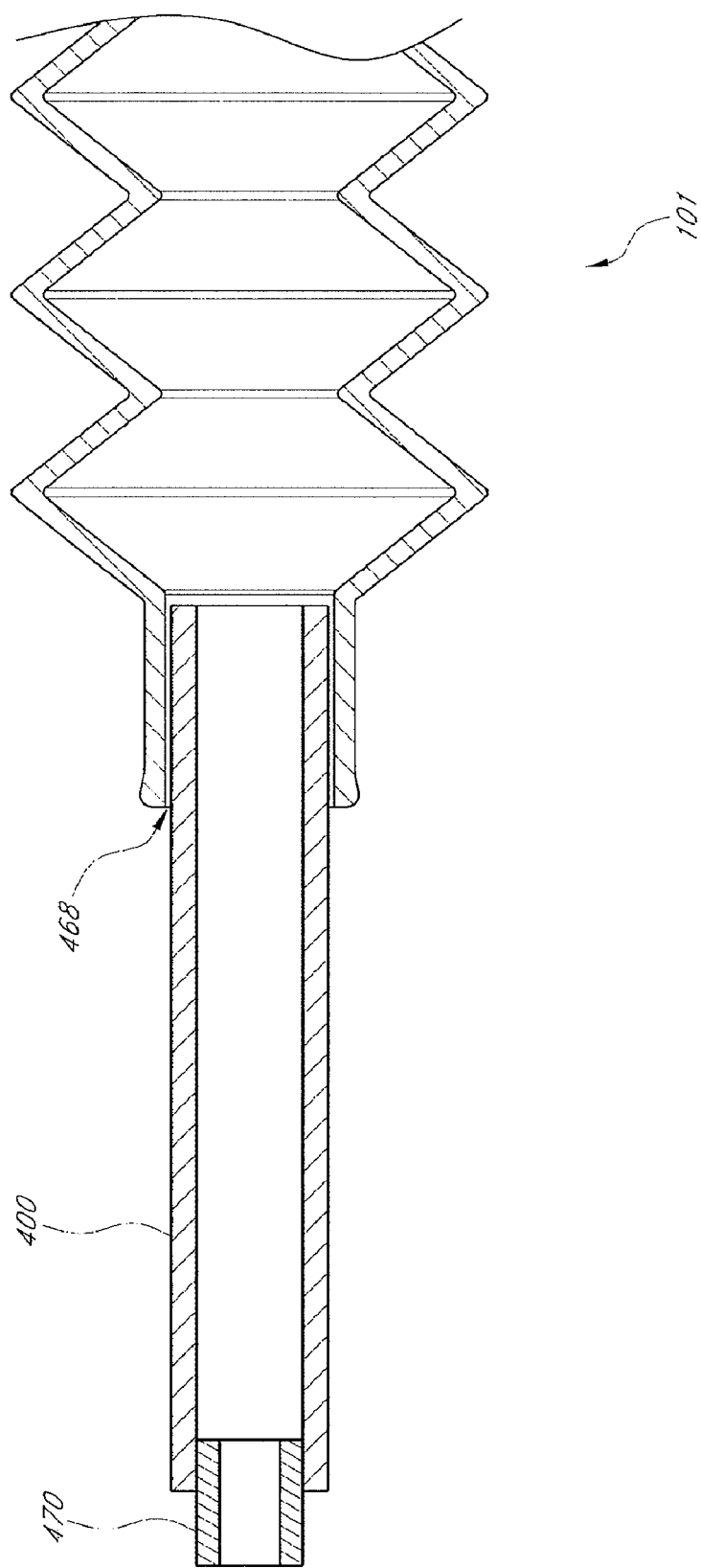
FIG. 2D is a schematic illustration as in FIG. 2C, where the sleeve is partially axially expanded.
Figure 2E:
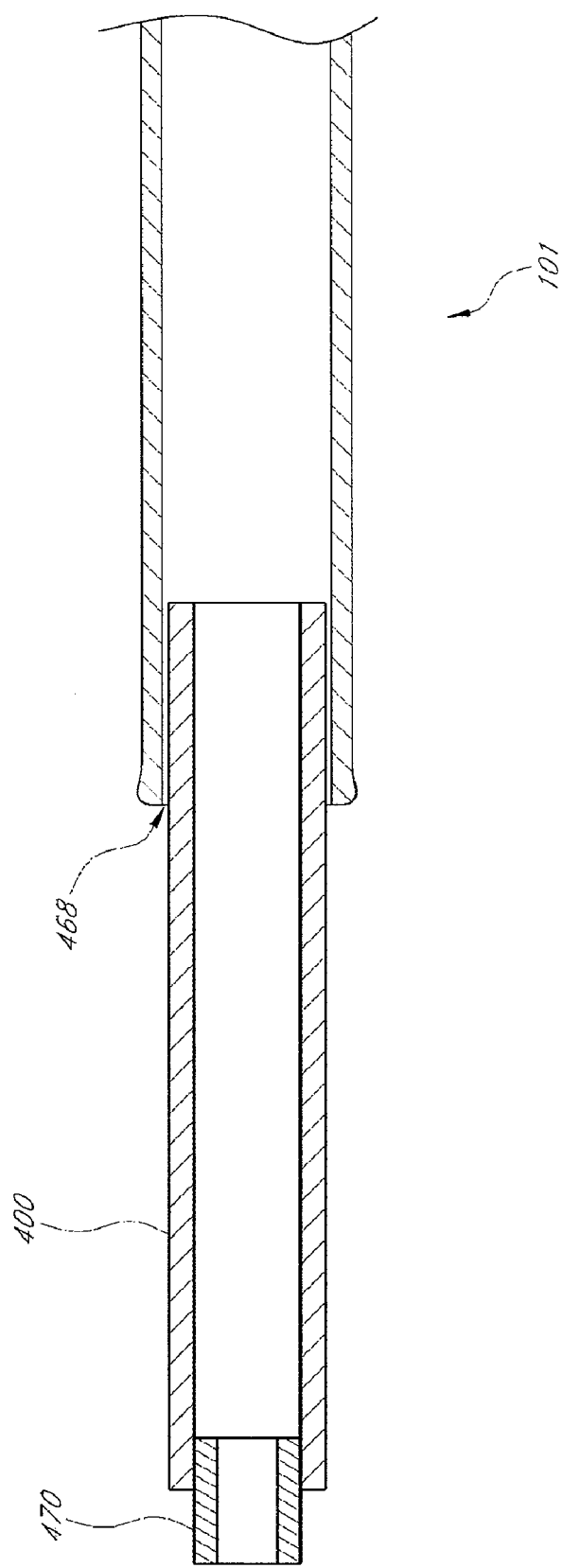
FIG. 2E is a schematic illustration as in FIG. 2D, where the sleeve is completely axially expanded.

FIGS. 2C-2E illustrates an embodiment of a sleeve 101 that does not require inversion prior to delivery within the body lumen. The sleeve 101 is shown operably attached at its proximal end 103 and forming a fluid-tight seal 468 with filling catheter 400, as described further below. The sleeve 101 shown is configured to form an axially compressed shape, such as having an accordion-like portion 103 for delivery, transforming into an axially elongated configuration after delivery, as shown in FIG. 2E. FIG. 2D illustrates an intermediate configuration where the sleeve 101 is in process of elongating to the axially elongated configuration. In some embodiments, the sleeve 101 may be pleated to form a bellows-like device. The sleeve 101 may be made of any appropriate material, although we have discovered that PTFE (TEFLON®) is especially well-suited for axially compressing the sleeve 101 in an accordion-like fashion.

The sleeve 101 can be transformed from an axially compressed configuration to an axially elongated configuration by flowing inflation media through the lumen of the sleeve 101 as disclosed above. The sleeve can also be transformed using a grasping tool, such as a snare, to provide a mechanical force to promote transformation and decrease the pressure and/or volume of inflation media required, as will be discussed below.

The distal end 112 of the sleeve 101 may be temporarily occluded or sealed during deployment to facilitate the pressure gradient sufficient to allow sleeve 101 to axially expand. In one embodiment, filling catheter 400 passes into the lumen of sleeve 101 and a fluid-tight seal 468 is created between the proximal end of sleeve 101 and the distal end of filling catheter 400, as shown. Tubing 470 can be utilized to provide a passageway between filling catheter 400 and device 416. In some embodiments, a temporary barrier can be created at distal end 112 of sleeve 101. The temporary barrier may be created by collapse of distal end 112 caused by the influx of fluid through filling catheter 400. In other embodiments, distal end 112 can be blocked with an absorbable or degradable plug comprising cellulose, sugar-based substances, PLA, as well as other techniques discussed elsewhere herein. Distal end 112 may also be closed with a grasping member such as a loop snare discussed elsewhere herein.

In some embodiments, the sleeve with an accordion-like portion as shown in FIGS. 2C-E can be expanded axially by at least about 50%, 75%, 100%, 125%, 150%, 200%, 250%, 300%, 400% or more of its axially compressed length. In some embodiments, the sleeve can be both inverted and axially compressed.

In some embodiments, the sleeve may include one or more elements that can be configured to be biased such that eversion of the sleeve is promoted. For example, the sleeve may have one or more embedded elements within or proximate to the wall of the sleeve with a spring force (e.g., a metal, such as a nitinol ribbon) biased to facilitate eversion.

Figure 3A:
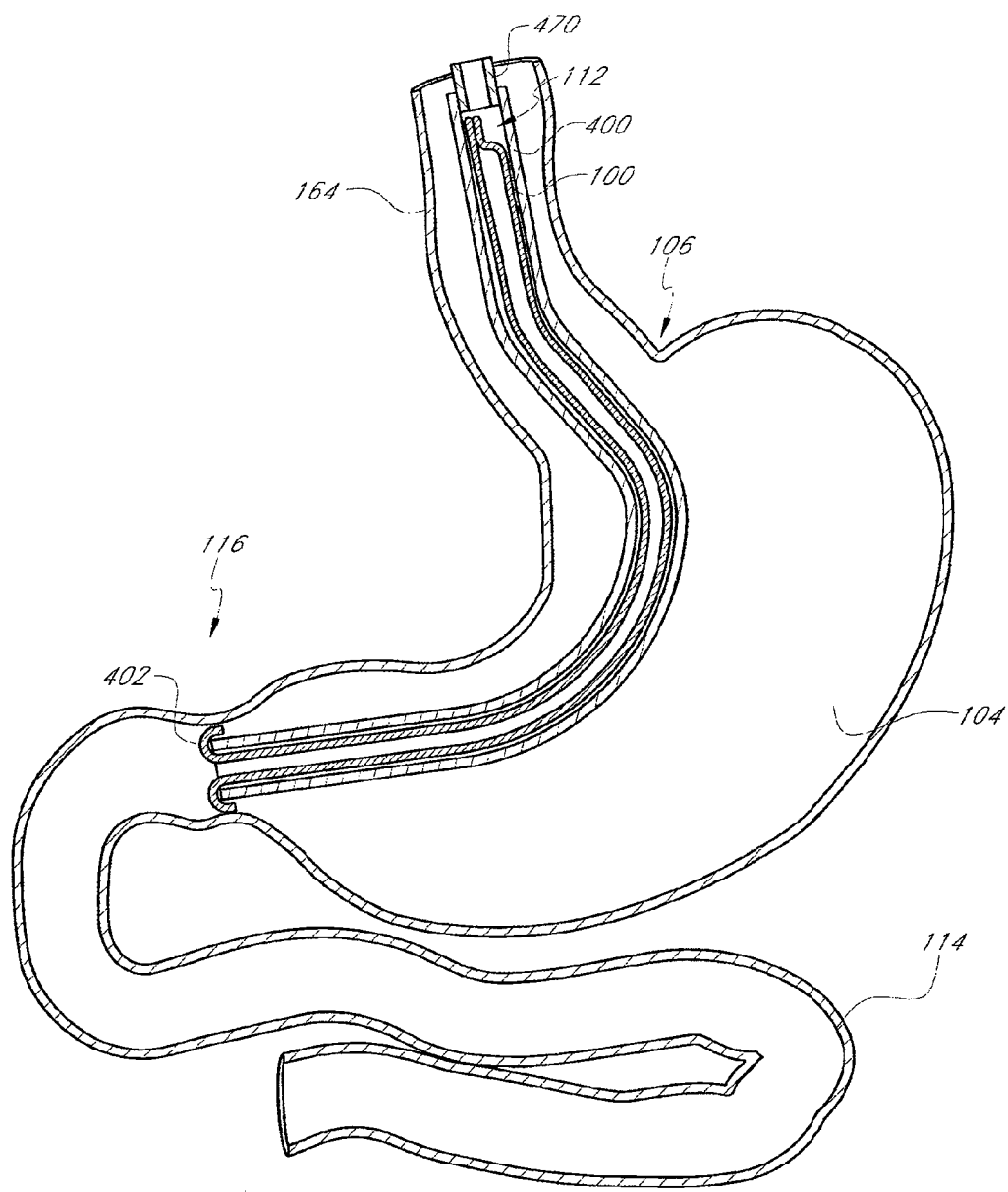
FIG. 3A is a schematic illustration of a filling tube extending through the stomach to the pylorus, having a toposcopically deliverable sleeve proximally retracted therein.

FIG. 3A shows an elongate, flexible filling catheter 400 transesophageally positioned such that it extends across the length of the stomach and its distal end 402 is about at the pylorus 116, or alternatively past the pylorus 116. The proximal end of sleeve 100 is attached to the distal end of filling catheter 400, and the distal end 112 of sleeve 100 retracted proximally within the filling catheter 400 at least as far as the esophagus 164 to fully invert the sleeve 100 within the filling catheter 100.

As used herein, the term "filling catheter" is intended to refer to any of a wide variety of structures which are capable of placing an evertable sleeve 100 in communication with a source of inflation media. In general, the filling catheter will include at least one lumen for conveying inflation media. In the illustrated embodiment, the central lumen of the filling catheter 400 is also utilized to receive the proximally retracted distal end 112 of the sleeve 100.

The filling catheter may exhibit sufficient column strength to enable distal advance of the distal end 402 to the desired site where eversion is to commence. Alternatively, collapsible filling catheters may be carried into position by a secondary instrument such as an endoscope, as is discussed below. The filling catheter may be a single lumen tube, as schematically illustrated in FIG. 3A, or a multi-lumen structure as will be apparent to those of skill in the art in view of the disclosure herein. To simplify the discussion herein, the filling catheter 400 will primarily be illustrated in its simplest form as an elongate flexible single lumen tubular body.

Figure 3B:
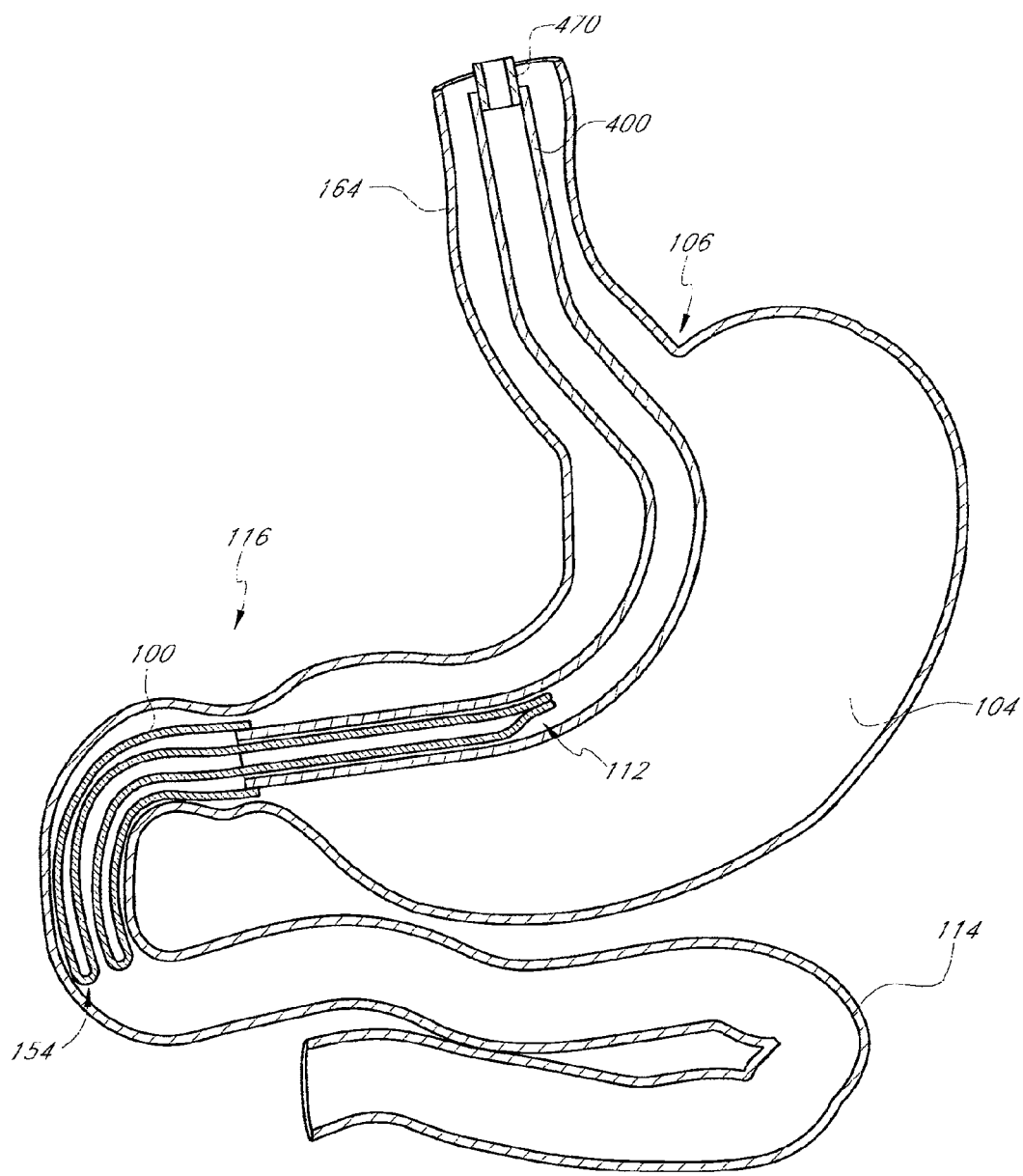
FIG. 3B is a schematic view as in FIG. 3A, with the sleeve partially everted into the intestine.

FIG. 3B shows sleeve 100 partially deployed such that distal end 112 has advanced past GEJ 106. As the sleeve 100 is deployed under the influence of an everting force, a leading fold or distal end 154 continually advances down the intestine until the sleeve 100 has been fully deployed. At that point, the leading fold 154 disappears, and distal end 112 of the sleeve 100 everts from the interior of the sleeve 100 to its final, fully extended configuration. See FIG. 3C.

Figure 3C:
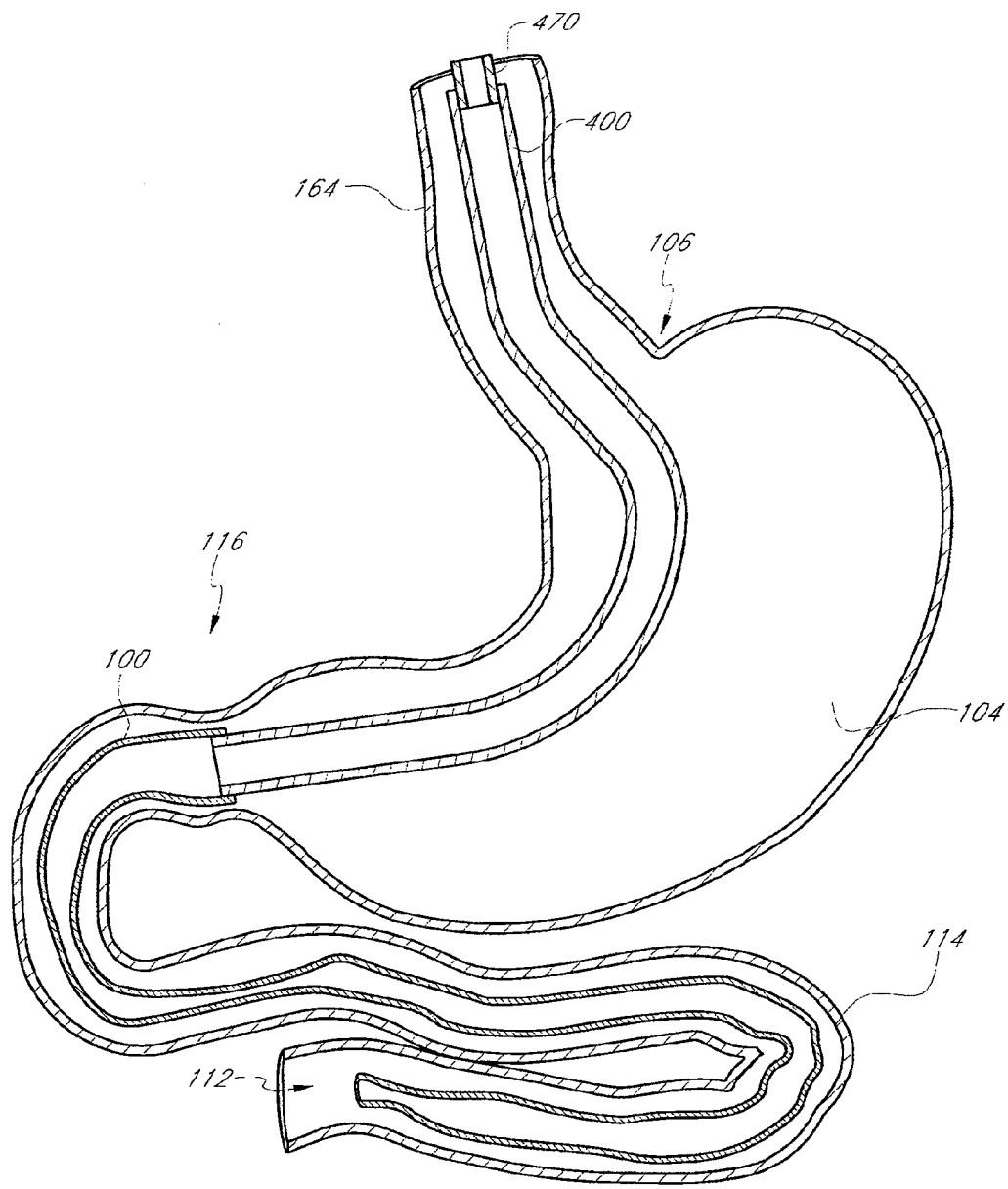
FIG. 3C is a schematic illustration as in FIG. 3B, with the toposcopic sleeve fully deployed within the intestine.

The device utilized to illustrate the sequence of FIGS. 3A through 3C is simplified in a variety of ways. For example, the distal end 402 of the filling catheter 400 is positioned at about, or at any point past the pylorus. The distal end 402 of the filling catheter 400 may be positioned at any of a variety of locations along the desired access pathway, taking into account the desired guidance to be provided to the sleeve 100 to enable it to reach its final fully deployed site. Thus, the distal end 402 may in an antegrade approach to a gastrointestinal access be positioned at least as far as the pylorus, to avoid improper deployment of the sleeve 100 within the stomach. However, depending upon device design, the distal end 402 may be advanced further downstream within the intestinal tract.

The proximal end of sleeve 100 is illustrated as being attached to the filling catheter 400 at its distal end 402. However, the sleeve 100 may be attached to the filling catheter at any of a variety of other locations, such as proximally of the distal end, depending upon the desired location of the finished assembly. For example, the proximal end of the sleeve 100 may be spaced apart from the distal end 402 of the filling catheter 400 by an overlap distance such at least about 5 cm, sometimes at least about 10 cm, or otherwise, depending upon the relationship between the desired attachment site, if any, between the proximal end of the sleeve 100 and the anatomy relative to the desired location of the distal end 402 of filling catheter 400 for the purposes of deployment.

In general, the filling catheter 400 performs at least two functions in the context of the present invention. Once function is to place the sleeve 100 in communication with a motive force which will operate to distally deploy the sleeve 100. Although generally described herein as an inflation media such as a liquid or a gas, the deployment force could also be provided by an elongate flexible push rod, which can be distally advanced through the central lumen to cause toposcopic deployment of the sleeve 100.

In addition, the filling catheter 400 serves the purpose of positioning the proximal end of the sleeve 100 at a predetermined point within the anatomy, from which toposcopic deployment will commence. Thus, the devices disclosed herein generally provide two end-to-end modes of access to a remote site. A first mode of access if provided from the natural or artificially created opening on the surface of the patient along an access pathway to the distal end 402 of the filling catheter 400. This mode of access generally involves conventional distal axial advance of a tubular member, relying either upon its own column strength, or the column strength provided by an associated device. Once the distal end 402 is in position at the desired launch point, the second mode of access is provided by distally deploying the toposcopic sleeve 100. The length of the filling catheter 400 may be varied considerably, depending upon the desired placement site for the distal end 402. In general, lengths of at least about 10 cm, often at least about 25 cm, and in some embodiments, at least about 50 cm, 60 cm, 75 cm, 100 cm, 125 cm, 150 cm, or more may be used.

In the case of particularly tortuous anatomy, more than one toposcopic delivery sleeves in accordance with the present invention may be utilized in series. For example, a first filling catheter may be positioned along a first length of an access pathway. The toposcopic sleeve 100 may then be deployed along a second segment of the access pathway. A second toposcopic delivery system may thereafter be coaxially distally advanced through the first filling catheter and first toposcopic sleeve. A second toposcopic sleeve may thereafter be deployed such that it extends beyond the distal end of the first toposcopic sleeve. In this manner, an access pathway comprising two or three or more coaxially aligned toposcopic sleeves 100 may be utilized.

Figure 4:
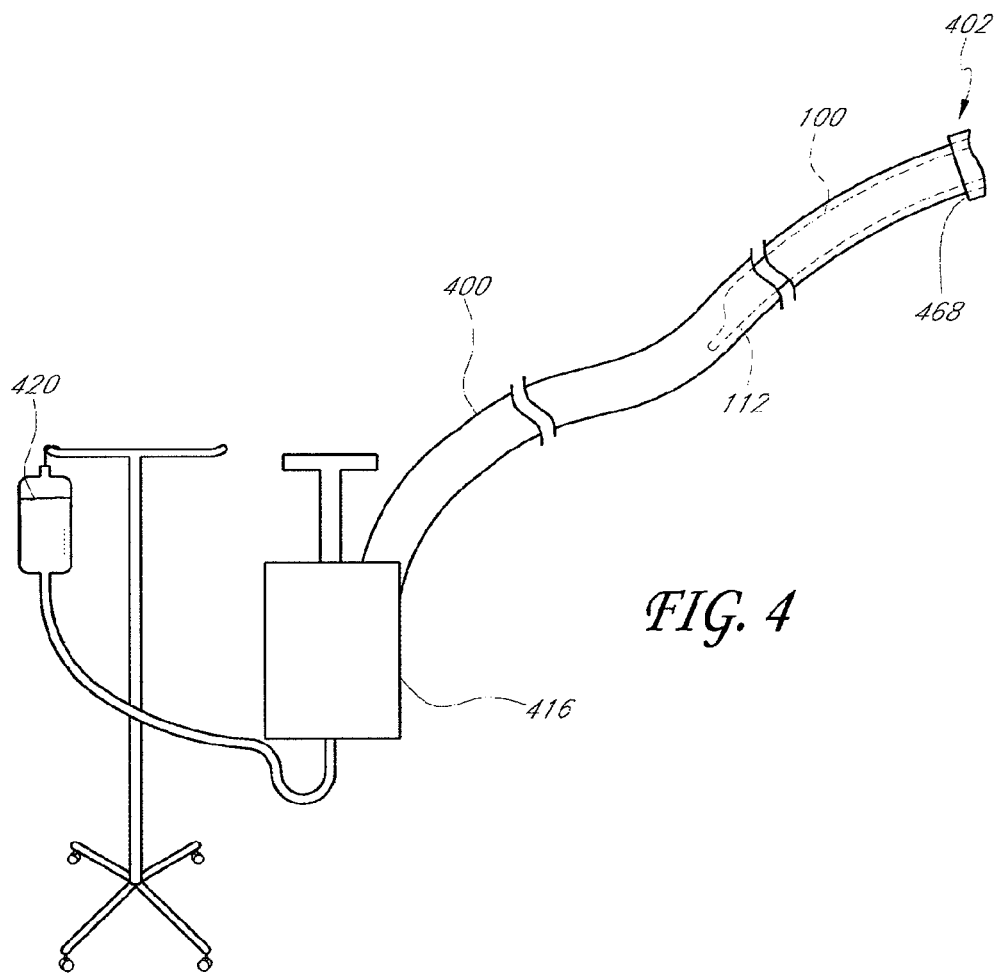
FIG. 4 is a schematic representation of a toposcopic deployment system in accordance with the present invention.

As shown in FIG. 4, filling catheter 400 is placed in fluid communication with a device 416 that infuses filling catheter 400 with inflation media such as a fluid. Device 416 can comprise, for example, an electronic or hand-actuated piston or plunger, hand pump, impeller pump, or peristaltic pump. In some embodiments, an endoscope can flush filling catheter 400 with fluid. Device 416 can in turn be placed in fluid communication with a fluid source 420. For example, device 416 can be in fluid communication with a container 420 that holds fluid. Container 420 can hold volumes of fluid ranging from 0.25 liters to 15 liters or more, depending upon the desired functionality. In certain GI embodiments, container 420 holds between about one and about five liters. Device 420 can flush fluid through filling catheter 400 at a rate ranging from about 5 cc to about 100 cc per stroke or actuation of device 420. In some embodiments, device 420 flushes fluid through filling catheter 400 at a rate of from about 30 cc to about 300 cc per stroke.

Optionally, the filling catheter 400 or the device 416 can have a pressure or volume measurement device to measure the pressure or delivered volume of fluid that is used to evert the sleeve 100. This can be used as an alternative way to determine when the sleeve is fully deployed. The volume measurement can be used to determine when enough fluid has been delivered to fully deploy the sleeve 100. The pressure measurement can be used to detect the pressure drop once the sleeve is fully deployed and the distal end 112 of the sleeve opens up to allow the fluid to pass through with less back pressure. Alternatively, if the distal end of the sleeve is designed not to open up after complete eversion, the pressure will increase upon full deployment of the device and indicate that toposcopic delivery is complete. Furthermore, the pressure or delivered volume measurement device can be utilized to prevent complications of over-filling, such as sleeve or tissue aneurysm formation or perforation, as described further below.

Figure 5:
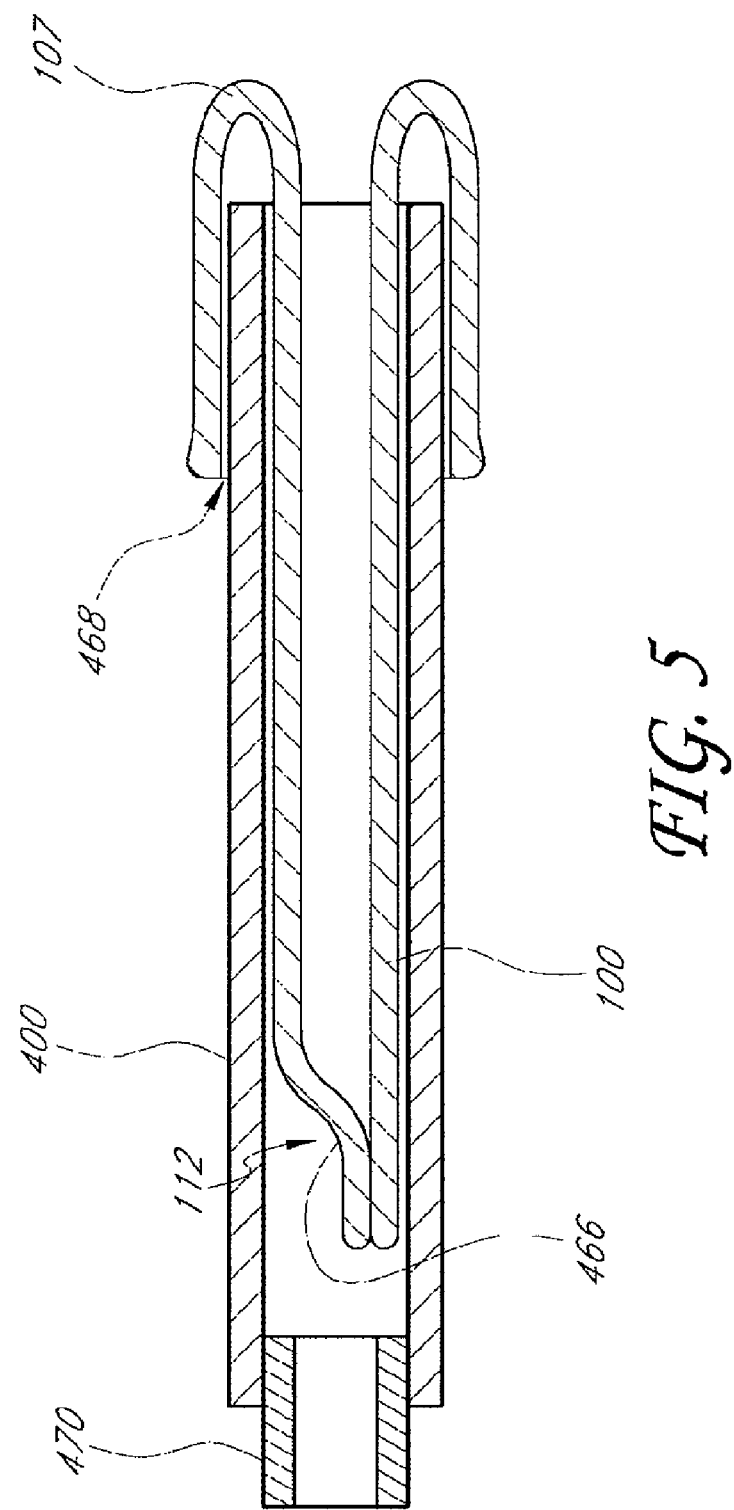
FIG. 5 is a detail view of the distal end of the system illustrated in FIG. 4.

In one embodiment, filling catheter 400 passes into the lumen of sleeve 100 and a fluid-tight seal 468 is created between the proximal end of sleeve 100 and the distal end of filling catheter 400, as shown in FIG. 5. Various ways to create a permanent or temporary (i.e., releasable or non-releasable) seal can be used as described herein and/or known in the art. The distal end 112 of sleeve 100 may then be advanced proximally into the lumen of filling catheter 400. Tubing 470 can be utilized to provide a passageway between filling catheter 400 and device 416. In this embodiment, a temporary barrier 466 can be created at distal end 112 of sleeve 100. Temporary barrier 466 may be created by collapse of distal end 112 caused by the influx of fluid through filling catheter 400. In other embodiments, distal end 112 can be blocked with an absorbable or degradable plug comprising cellulose, sugar-based substances, PLA, as well as other techniques discussed elsewhere herein.

Figure 6A:
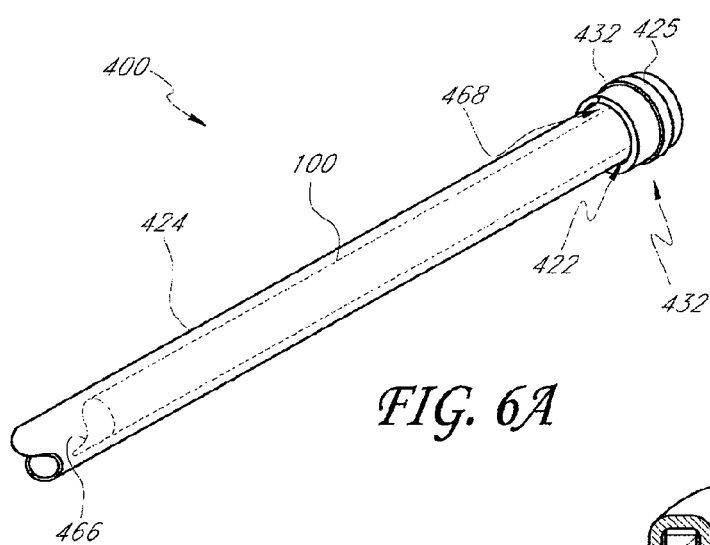
FIGS. 6A and 6B are additional detail views of a toposcopic deployment system.

Various embodiments of filling catheter 400 are contemplated by the present invention. In one embodiment, as shown in FIG. 6A, filling catheter 400 is a pushable tube 424 with an optionally releasable clamp or other connection 425. If releasable, clamp 425 may be released in any of a variety of ways, such as by pulling a pull wire which extends proximally through the overtube. Alternatively, if configured to function just as an access and/or delivery device, the clamp 426 or other connection does not need to be releasable, such as a glued, welded, sutured, or created as a one-piece construction with the filling catheter. In the illustrated embodiment, sleeve 100 extends proximally through the lumen of pushable tube 424 and sleeve rim 432, where the proximal end of sleeve 100 is inverted over and releasably (or alternatively non-releasably) secured to the distal end 422 of tube 424.

Figure 6B:
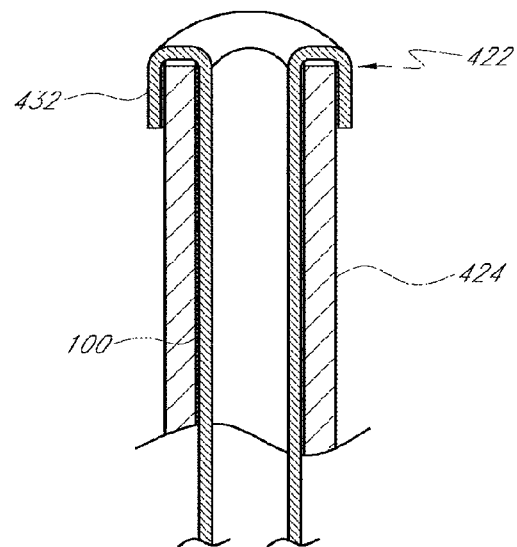
Figure 6C:
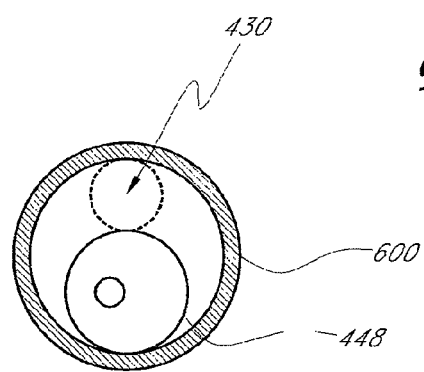
FIG. 6C is a schematic cross sectional view illustrating the available space within an over tube, for an endoscope and a toposcopic deployment system.

FIG. 6B is a longitudinal cross-sectional view of pushable tube 424 showing distal end 422 of tube 424 over which sleeve rim 432 is inverted. FIG. 6C is a transverse cross sectional view of an overtube 600 showing the available working volume 430 remaining within the lumen of overtube 600 for filling catheter 400 when endoscope 448 is within the lumen.

Figure 7A:
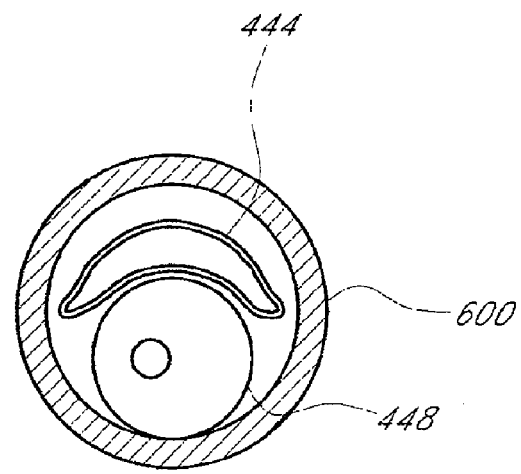
FIG. 7A is a cross sectional view through an over tube, illustrating an endoscope and a collapsible filling catheter.
Figure 7B:
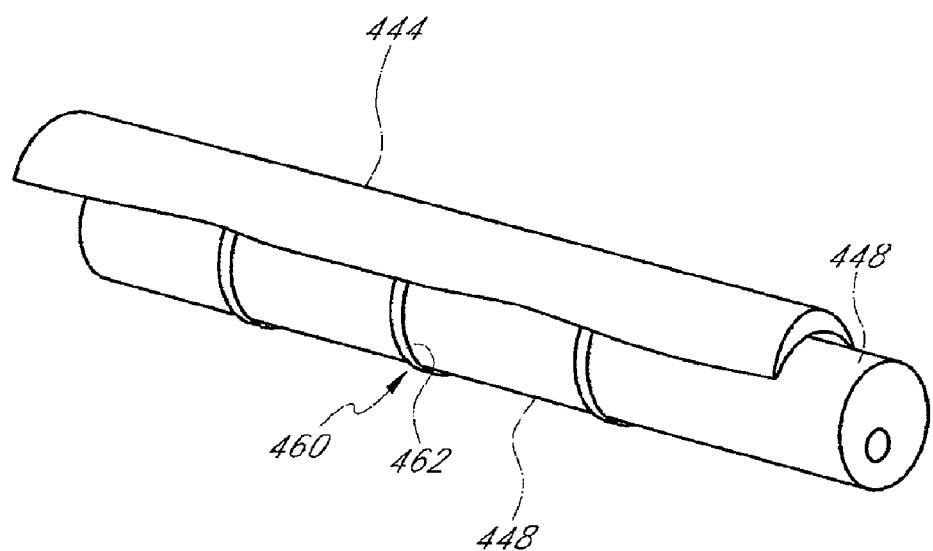
FIG. 7B is a side perspective view of an endoscope, having a collapsible filling catheter attached thereto.

FIG. 7A is a transverse cross section of endoscope 448 and collapsible filling catheter such as lay-flat tube 444 within overtube 600 with tube 444 lying on top of endoscope 448. Lay-flat tube 444 may be attached with means 460 to the outside of endoscope 448 as shown in FIG. 7B to aid in its insertion because the floppiness of tube 444 renders advancement on its own difficult. Alternatively, the lay flat tube can be grasped near the connection with the proximal end of the sleeve 100 and advanced with an endoscope and advanced to the desired location without any direct connection between the lay flat tube and the body of the endoscope. See, e.g., FIG. 10.

Figure 7C:
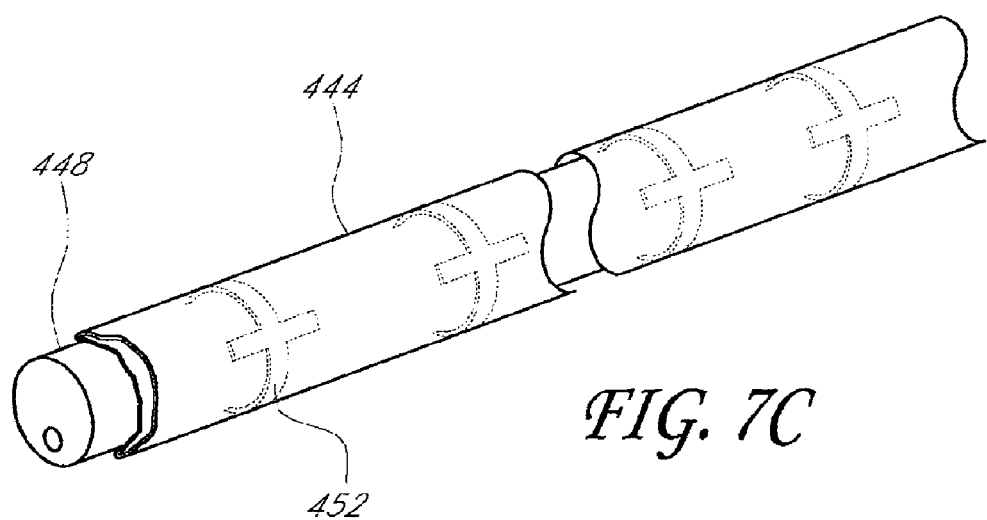
FIG. 7C is an alternate view of an endoscope having a collapsible filling catheter attached thereto.

FIG. 7B depicts tube 444 lying on top of endoscope 448 and means 460 comprising bands 462 wrapped around endoscope 448 and attached to or formed as a part of the tube 444 to attach tube 444 to endoscope 448. Means 460 for attachment can also comprise attachment strips 452, as shown in FIG. 7C, that wrap around at least a portion of the circumference of endoscope 448 and are attached on one side of the lay flat tube 444. Tube 444 is placed on top of endoscope 448 and strips 452 are attached to endoscope 448 by virtue of the adhesive properties of the outward facing surface of strips 452 or by a spring force of the strips 452 that lock onto the housing of the endoscope. Other means 460 for attachment can be used to secure tube 444 to endoscope 448 such as a direct adhesive bond between tube 444 and endoscope 448, first and second complementary mechanical interfit structures, or others as would be understood by those skilled in the art. The means 460 for attachment should allow tube 444 to expand during filling or flushing with fluid.

Figure 8:
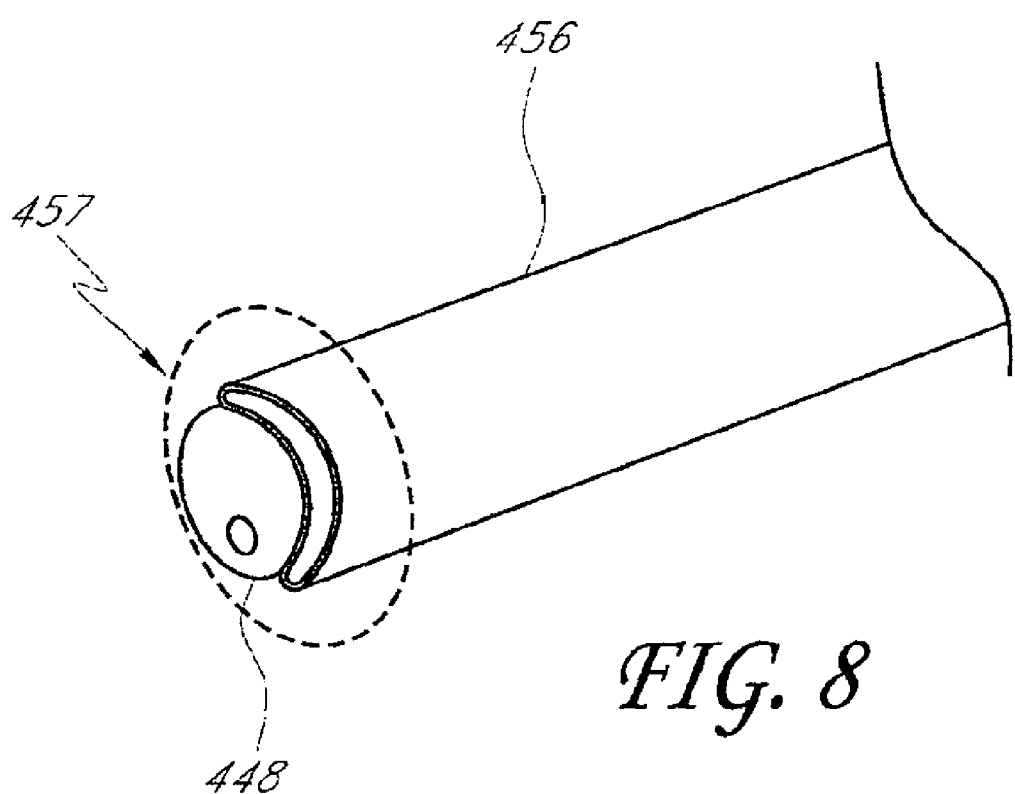
FIG. 8 is a cross sectional view as in FIG. 7A, with a fixed cross sectional configuration filling catheter.

In other embodiments, filling catheter 400 comprises a semi-rigid (fixed cross sectional configuration) catheter 456 which lies adjacent endoscope 448. Semi-rigid catheter 456 can have a crescent or banana-shaped cross-sectional configuration as shown in FIG. 8. Banana-shaped semi-rigid catheter 456, like lay-flat tube 444 (when in the expanded configuration), has a central lumen with a cross sectional area sufficient to receive sleeve 100. Also shown in FIG. 8 is the dimension of the inner diameter 457 of overtube 600 within which endoscope 448 and catheter 456 would reside. In some embodiments, endoscope 448 has an outer diameter of about 12 mm and inner diameter 457 is about 16 mm, leaving a working volume with a transverse dimension of about 4 mm for catheter 456.

In both the lay flat tube 444 configuration and the semi-rigid catheter 456 these devices are alternative devices to the filling catheter 400. Thus, the sleeve 100 (not shown) would be inverted with the distal end 112 retracted proximally into the tube 444 or 456 and the proximal end folded over the distal end of the lay flat tube 444 or semi-rigid catheter 456.

Figure 9:
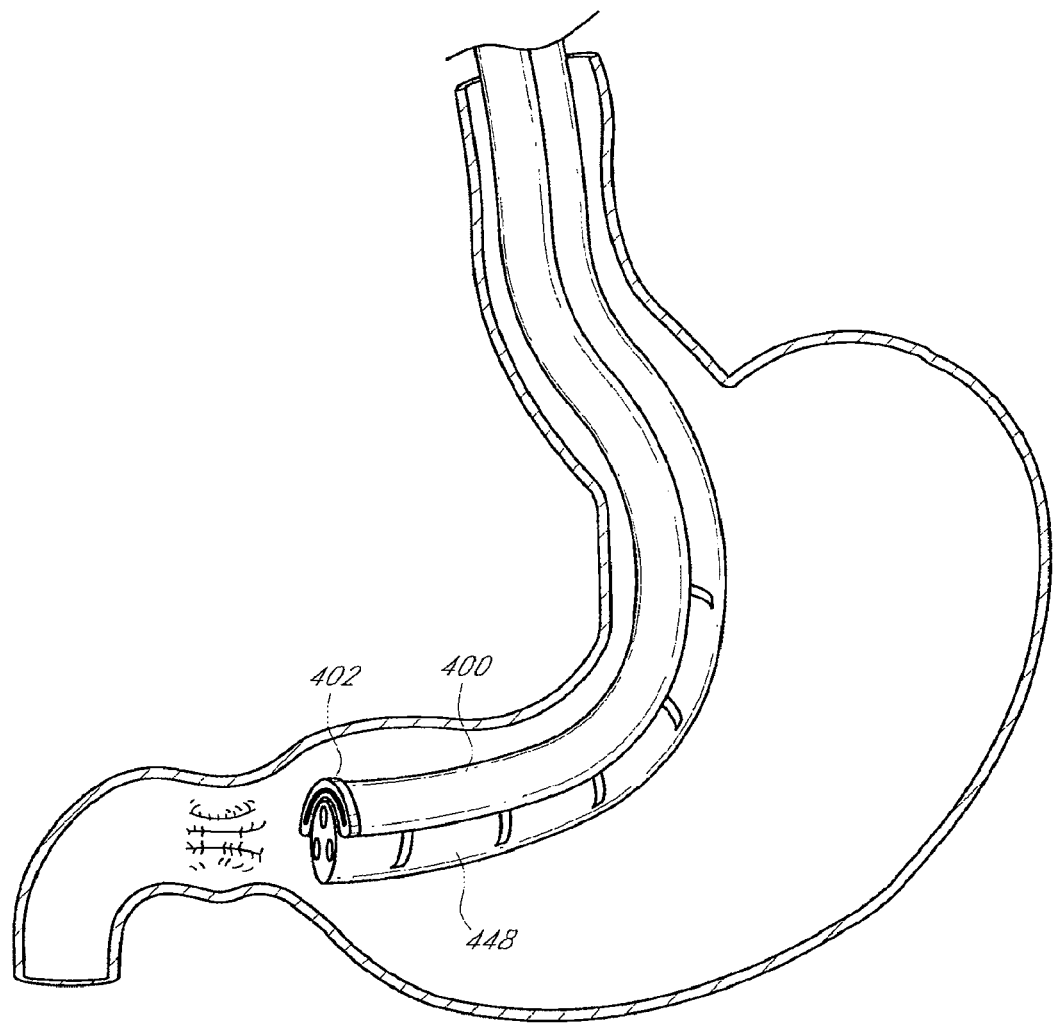
FIG. 9 is a schematic illustration of an endoscope carrying a collapsible filling catheter to a position in the vicinity of the pylorus.

In another embodiment the filling catheter 400 may lack sufficient column strength to be pushable. See FIG. 9. In this embodiment the filling catheter 400 comprises a flexible collapsible conduit for the pressurized medium to act on the everting sleeve.

A separate device is used to provide sufficient column strength to get the distal end 402 of the inverted device to the desired delivery point. The separate pushable device could be a pushable rod, catheter, or any of the types of endoscopes commonly used in GI procedures. These include colonoscopes, pediatric endoscopes, enteroscopes or the double balloon enteroscopes used for accessing small intestine.

The filling catheter 400 could be attached along the length of the pushable device in a piggy-back fashion with the use of clips, adhesives thermal bonding or any of the other methods that would be known to those with skill in the art. Alternatively, the pushable device could only be attached to the filling catheter 400 at or near the interface of the filling catheter with the everting sleeve. The pushable delivery device could be attached at this point or devices such as graspers or clamps, such as those that can be used through a working channel of an endoscope could be used to hold the filling catheter and drag it through the lumen to the desired delivery point. See FIG. 10. The filling catheter 400 could have a "lay flat" design that reduces its cross sectional profile in at least one direction. An example of this lay-flat shape cross section would be crescent shaped. The crescent shaped cross section would allow for maximum cross sectional area of the filling catheter while still having an endoscope along side it in a lumen.

Figure 10:
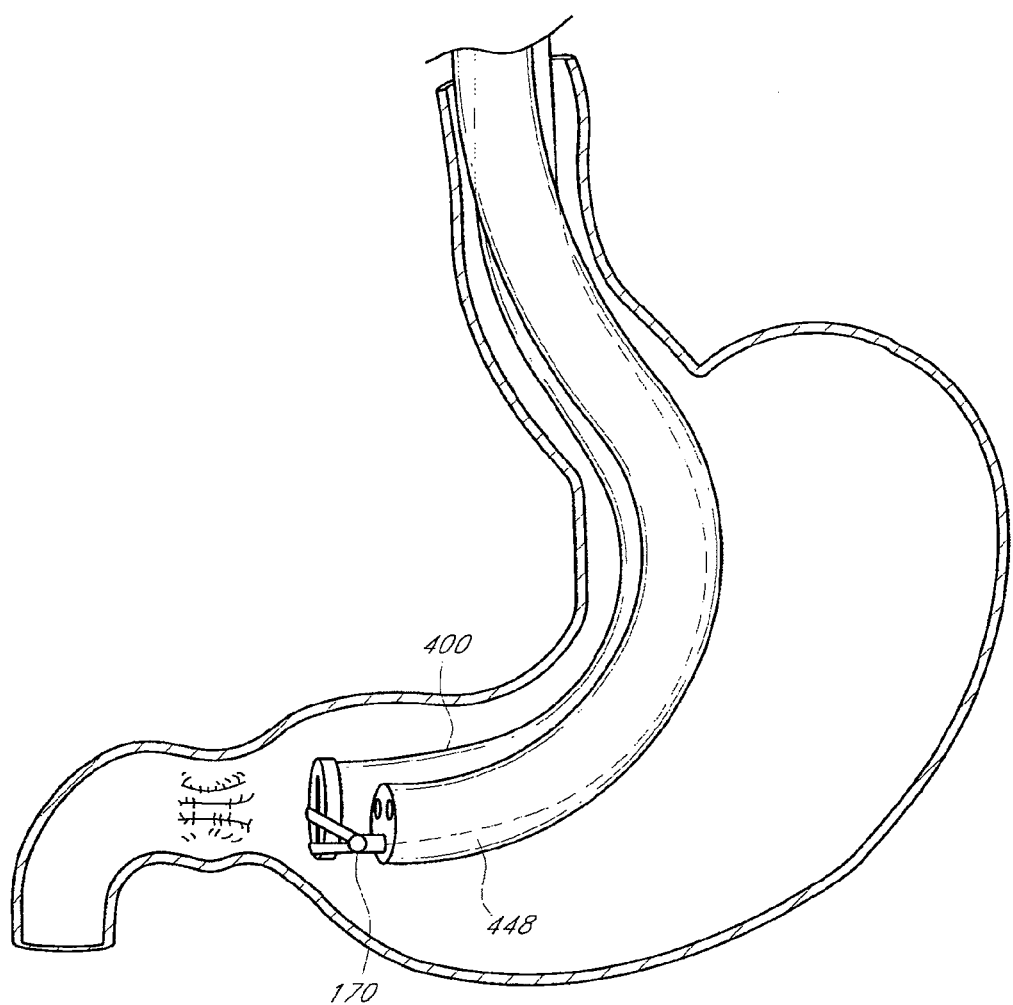
FIG. 10 is a schematic illustration of an alternate method of advancing a collapsible filling catheter to the vicinity of the pylorus.

Referring to FIG. 10, there is schematically illustrated an endoscope 448 which has been advanced into position adjacent the pylorus. A grasper or other connecting tool 170 extends through a working channel on the endoscope 448, for grasping or otherwise removably connecting to the filling catheter 400. This configuration enables the endoscope 448 to "pull" a filling catheter 400 by its distal end, in a distal direction to position the filling catheter 400 at the appropriate site in the anatomy. Filling catheter 400 for this purpose, may have a highly flexible construction with relatively low pushability.

Figure 11A:
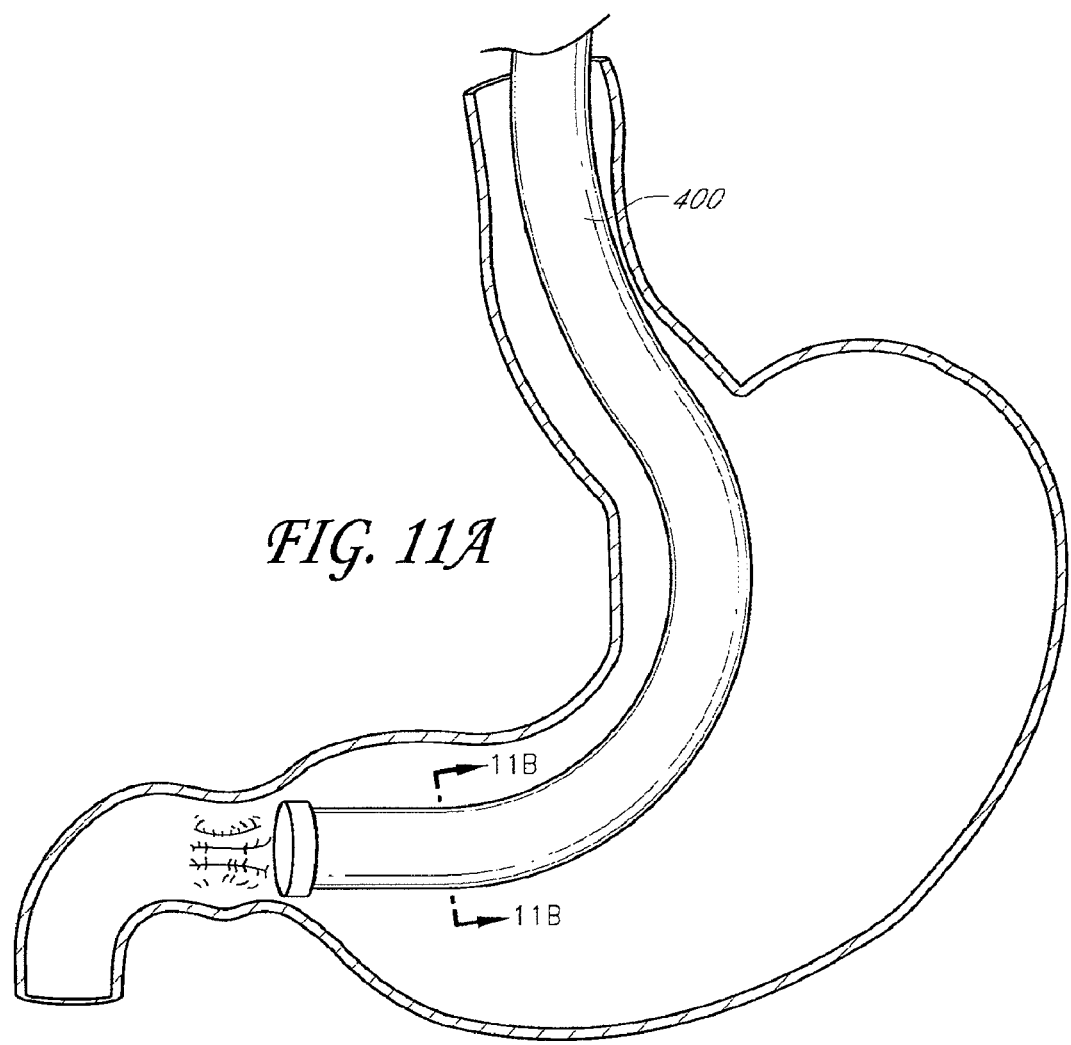
FIGS. 11A and 11B illustrate a steerable filling catheter, with a distal end positioned in the vicinity of the pylorus.
Figure 11B:
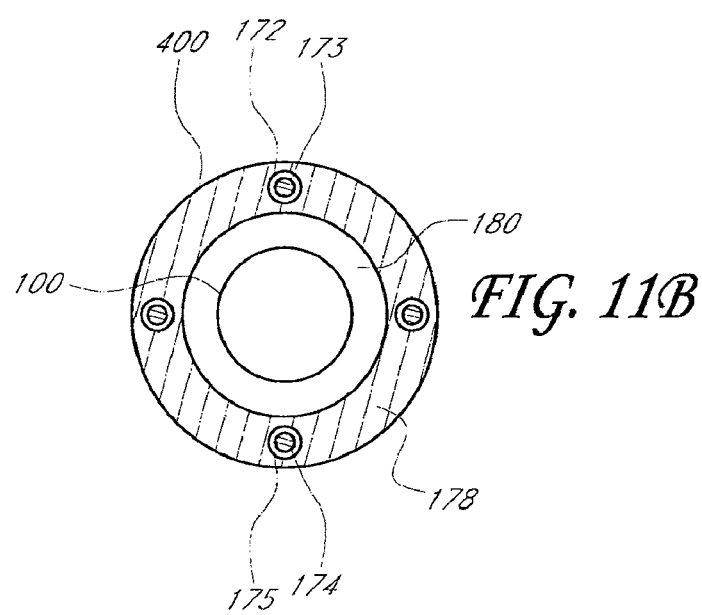

Referring to FIGS. 11A and 11B, there is disclosed a steerable filling catheter 400 in accordance with the present invention. The steerable catheter 400 may be guided to the desired site, through a combination of distal pushing and bending of the catheter body.

Steerability may be accomplished in any of a variety of ways, such as through the use of one or more pull wires. Referring to FIG. 11B, there is illustrated a cross-sectional view through the filling catheter 400. The catheter 400 comprises an elongate flexible tubular body, having a proximal end and a distal end. The tubular body may comprise a multi-lumen extrusion, as is understood in the catheter arts. The catheter 400 includes a tubular wall 178 defining at least one central lumen 180 extending axially therethrough. Within or adjacent the wall 178 there is provided at least one axially extending lumen 172 for axially moveably receiving a pull wire 173. Pull wire 173 is configured such that proximal retraction of the pull wire 173 with respect to the wall 178 causes a deflection of the distal end of the filling catheter 400.

Preferably, at least a second lumen 174 for axially moveably receiving a second pull wire 175 is also provided. The pull wires 173 and 175 may be oriented at approximately 180° apart from each other, with respect to the longitudinal axis of the catheter 400. A third and a fourth pull wire may also be provided, depending upon the desired functionality of the catheter 400.

The implementations of the invention discussed above have been primarily directed towards providing access to a remote location in the body. The toposcopic sleeves of the present invention may additionally be utilized to deliver articles to remote sites, as discussed below. The delivered device may be a diagnostic or therapeutic device, or an alternative access system such as a guidewire or rail. The delivered device may be detached at the delivery site and left in place (an implant) or removed from the body following the diagnostic or therapeutic procedure.

Figure 12A:
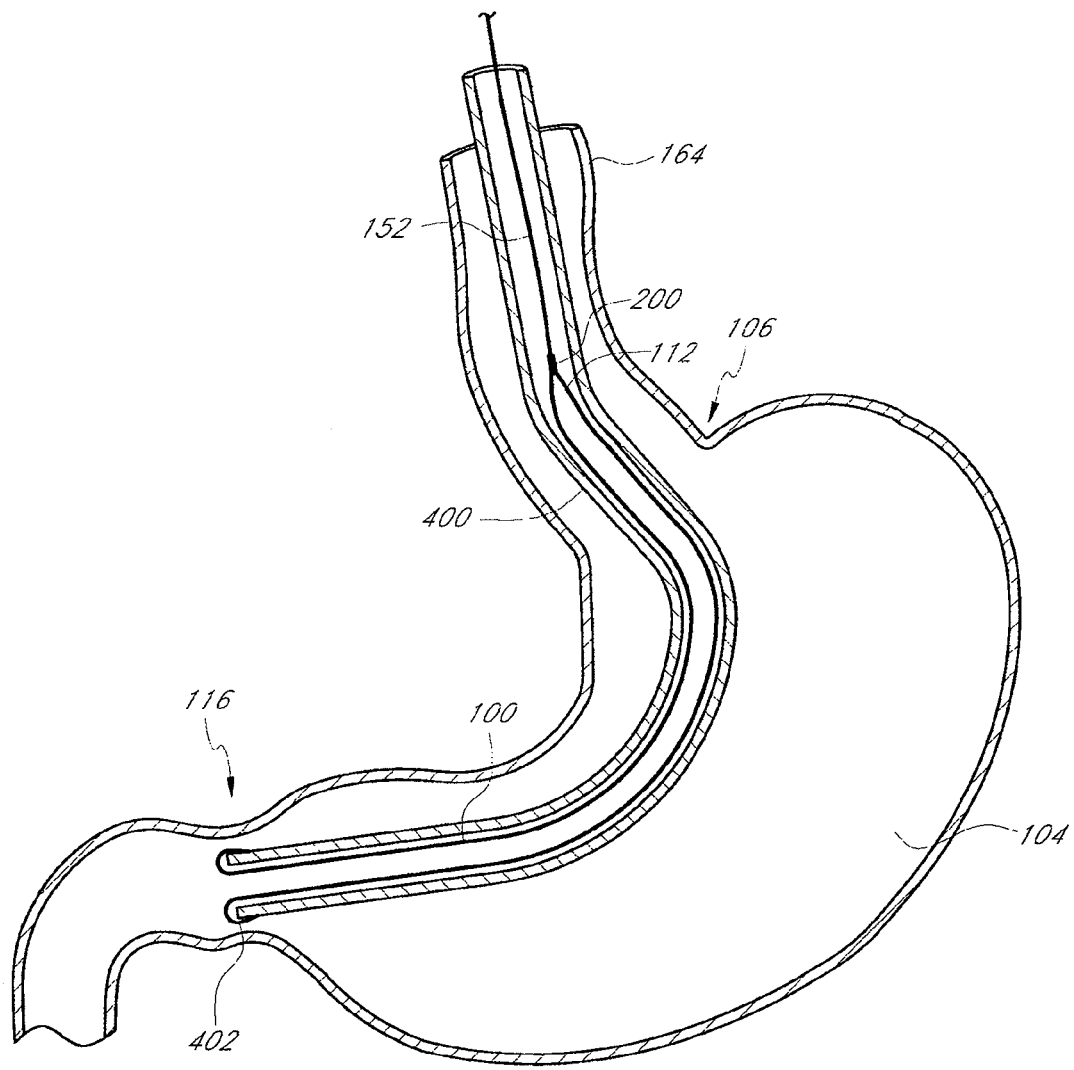
FIGS. 12A and 12B illustrate a toposcopic delivery system in accordance with the present invention, for delivering a guidewire or other device to a remote treatment site.

Referring to FIG. 12A, there is illustrated a delivery device in accordance with the present invention. The delivery device includes a filling catheter 400, illustrated as extending across the stomach such that a distal end 402 is in the vicinity of the pylorus 116. A toposcopic sleeve 100 is proximally retracted within the filling catheter 400 as has been discussed.

Figure 12B:
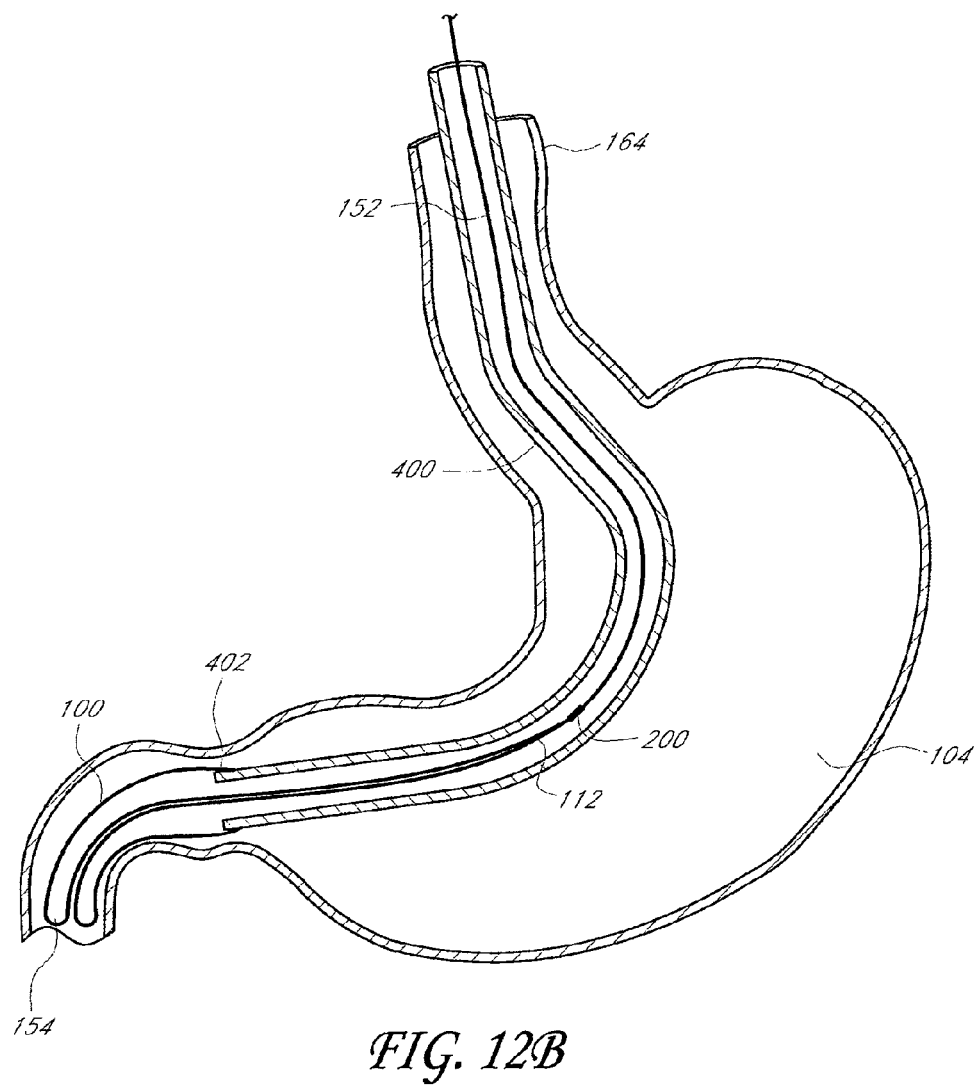

The distal end 112 of the toposcopic sleeve 100 is closed, and provided with a connector 200. As illustrated in FIG. 12B and as will be apparent in view of the preceding discussion, the connector will advance distally in response to the introduction of inflation media through filling catheter 400.

The connector 200 may be removably or permanently connected to any of a wide variety of devices, examples of which have been identified above. In FIG. 12A, the connector 200 is connected to a guidewire 152. As the sleeve 100 is everted distally, the connector 200 advances distally, pulling guidewire 152 in a distal direction. In this manner, a guidewire 152 may be distally axially advanced through a tortuous pathway, within the sleeve 100.

Following complete evertion of the sleeve 100, the connector 200 may be caused to release the guidewire 152. Release may be accomplished in any of a variety of ways, such as by introduction of a solvent through sleeve 100, introduction of a solvent around the outside of the filling catheter 400, thermally releasing a polymeric link through the use of a monopolar or bipolar electrical circuit as is understood in the detachable intracranial aneurysm coil field, or the like. Alternatively, the guidewire 152 may comprise a hollow outer sleeve which axially slideably receives an inner core. Axial, proximal or distal displacement of the core with respect to the sleeve can be utilized to detach the connector 200. The guidewire may also be forcibly detached, by a pushing, twisting or pulling motion.

Following detachment of connector 200 and opening of the distal end of the sleeve, the sleeve 100 may be proximally retracted leaving the guidewire 152 in place. Alternatively, devices may be advanced along the guidewire 152 through the sleeve 100, leaving the sleeve 100 in position.

Any of a wide variety of alternative devices may be attached to the sleeve 100 at connector 200. These include various sensors, or other diagnostic or therapeutic devices described above.

Figure 13E:
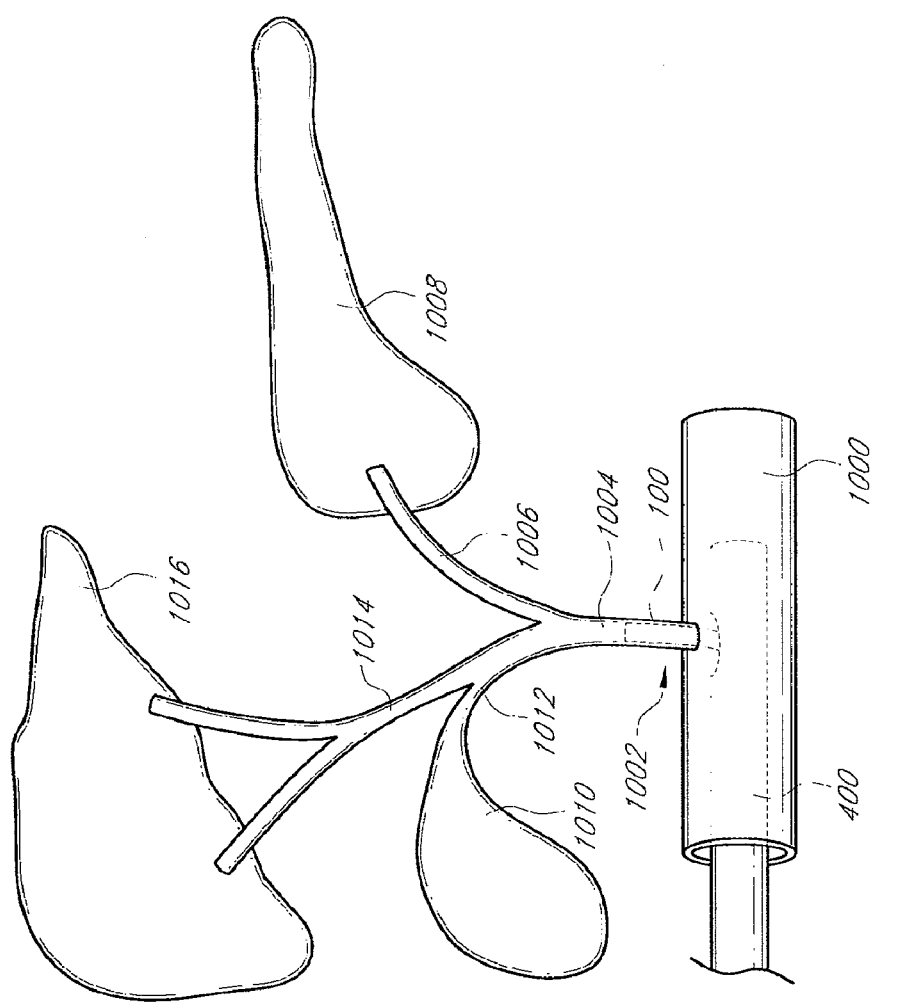
FIG. 13E schematically illustrates a sleeve being deployed into the common bile duct, according to one embodiment of the invention.

An alternative guidewire placement system is illustrated in FIGS. 13A-13D. Referring to FIG. 13A, an elongate flexible tubular filling catheter 400 is provided in a dual lumen configuration. A first lumen 210 is provided for receiving the toposcopic sleeve 100 as has been discussed. Toposcopic sleeve 100 may be provided with a connector 200, for connection to a pull wire 152.

The filling catheter 400 is additionally provided with a second wire guide or lumen 212. Two lumen tubular bodies may be formed in accordance with extrusion techniques which are well understood in the medical catheter arts.

The second lumen 212 receives a guidewire 214. The guidewire 214 is the procedure guidewire which is to be left in position following removal of the filling catheter 400.

Referring to FIG. 13A, the procedure guidewire 214 extends around the distal end 402 of the filling catheter 400 and into the interior of the toposcopic sleeve 100. In the illustrated embodiment, the distal end 216 of guidewire 214 is positioned in the vicinity of the connector 200.

As the connector 200 is advanced distally in response to introduction of inflation media, the sleeve 100 everts in a distal direction, and the guidewire 214 is laid down along the outside of the sleeve 100.

Referring to FIG. 13C, following complete deployment of the toposcopic sleeve 100, the guidewire 214 has been laid down along the pathway until distal end 216 is released from the toposcopic sleeve 100.

Referring to FIG. 13D, proximal retraction on pull wire 152 proximally retracts the toposcopic sleeve 100 back into the filling catheter 400, leaving the guidewire 214 in position along the desired access pathway. The filling catheter 400 may thereafter be proximally retracted, as may be desired, leaving the guidewire 214 extending throughout the length of the desired access pathway.

Proximal retraction of the filling catheter 400 is preferably accomplished in a manner that does not displace guidewire 214. This may be accomplished by providing a guidewire 214 having a sufficient proximally extending length that the portion extending outside of the patient is longer than the length of the filling catheter 400. Alternatively, the filling catheter 400 may be constructed in a rapid exchange configuration, in which the guidewire 214 exits a proximal side aperture on filling catheter 14 which is in communication with the second lumen 212. The side aperture may be positioned along the length of the filling catheter 400, such as within about 10 or 20 cm of the distal end.

The leading bend 154 on toposcopic sleeve 100 may be characterized by a 180° turn having a relatively small radius of curvature. This may prevent the use of a relatively stiff guidewire, as will be appreciated by those of skill in the art.

For this purpose, the guidewire 214 may comprise a highly flexible, small diameter outer sleeve having a removable central stiffening core therein. The outer guidewire sleeve may be toposcopically deployed as illustrated in FIGS. 13A-13D. Following complete deployment of the guidewire sleeve, the central stiffening core may be distally advanced therethrough, to form a final guidewire construct. Alternatively, the flexible guidewire sleeve may be proximally retracted following placement of the guidewire core, leaving the guidewire core in place to facilitate a subsequent access. The guidewire sleeve may comprise any of a variety of configurations, such as a thin walled collapsible polymeric tube, or a spiral wrapped tube comprising a polymeric or flat metal ribbon as are understood in the flexible catheter arts.

Referring to FIG. 13C, the guidewire 214 extends along the outside of the fully deployed toposcopic sleeve 100. As an alternative, a lumen may be provided within the wall or attached to the wall of the toposcopic sleeve 100 to enclose the free end of the guidewire 214. This lumen may be formed by bonding a concentric sleeve to the toposcopic sleeve 100 to provide a dual layer sleeve, having a mandrel removably positioned during the bonding process such removal of the mandrel results in a guidewire lumen which may be in communication with the second lumen 212. Alternatively, a flexible sleeve may be bonded to the exterior surface of the toposcopic sleeve 100. Removal of the filling catheter 400 may be accomplished as previously described, leaving the guidewire 214 in position to provide subsequent access to the target site.

The toposcopic tube may be made from any of a variety of materials, depending upon the desired performance of the finished device. Polyurethane may be a preferred tube material for certain implementations, as it has low distensibility (that is, stress rises rapidly and non-linearly with strain), and is tough and penetration-resistant. For colonoscopy, a polyurethane liner may have a diameter between about ½ inch and 1 inch, and a wall thickness between about 0.002 inch and 0.007 inch. Polyurethane tube about ¾ inch in diameter and having a wall thickness 0.003 inch formed by dielectric sealing of 3 mil polyurethane sheet can be everted using fluid pressures of a few pounds per square inch, when lubricated as described further below.

Latex rubber may also be a suitable tube material for low pressure eversion. A latex liner may have an inner diameter between about ½ inch and about 1 inch, and a wall thickness between about 0.010 inch and 0.030 inch. Latex tube about ¾ inch in diameter and having a wall thickness 0.015 inch can be everted using fluid pressures in the range 1-2 pounds per square inch when well-lubricated. Latex may be less preferred than polyurethane, however, as latex is more easily stretched and distended than polyurethane.

In general, the sleeve should be made of a material that allows it to be sufficiently flexible to conform to the shape of a device being placed therethrough. For most applications, the material, which is typically thin, should exhibit resistance to tearing and stretching (i.e., have good linear strength). Generally, the sleeve should be smooth and lubricious such that the sleeve, as it is laid down by the advancement of the device, or being withdrawn from the body, is atraumatic to delicate linings of the body, such as sphincters, tissue folds, ducts, and other passages. Another material with desirable properties is expanded polytetrafluoroethylene (ePTFE). Custom extruded ePTFE, which is available from Zeus Medical Products, Inc., Orangeburg, S.C., is produced from polytetrafluoroethylene (PTFE) tubing that is expanded under controlled conditions which advantageously adds microscopic pores throughout the material. The result is a soft, flexible material with increased linear strength. The wall thickness of the sleeve depends largely on the application and material used and may typically range from 0.001-0.01" for ePTFE. A more preferred range for ePTFE when introducing a standard ERCP device would be in the 0.002-0.005" range, most preferably around 0.0025". Many other polymeric films, such as high-density or low-density polyethylene, have desirable properties, particularly those with adequate linear strength. Their lower cost can be significant, particularly for longer devices. Other possible materials include latex, woven fabrics, or biomaterials that can be fabricated into a thin, flexible sheet or tube of sufficient strength. The sleeve can also be coated or impregnated with other compounds and materials to achieve the desired properties.

In some embodiments, the sleeve itself may be degradable and formulated to dissolve within a desired time such as no more than approximately 1 day, 3 days, 7 days, 14 days, 1 month, 3 months, 6 months, 9 months, 12 months, 18 months, 24 months, or 36 months. This can be advantageous when the sleeve is used primarily as a delivery device for another diagnostic or therapeutic device as described elsewhere in the application, or if the sleeve is intended as a temporary bypass, such that a subsequent removal procedure for the sleeve becomes unnecessary.

In some embodiments, the sleeve may be made of a biodegradable polymer. Examples of polymers that may be used for the biodegradable sleeve include, for example, poly(L-lactide) (PLLA), poly(D,L-lactide) (PLA), polyglycolide (PGA), poly(Llactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly(phosphate ester), poly(amino acid), poly(hydroxy butyrate), polyacrylate, polyacrylamide, poly(hydroxyethyl methacrylate), elastin polypeptide co-polymer, polyurethane, polysiloxane and their copolymers.

A film (a sheet or layer) of polyurethane (an elastomeric material) may be laminated with lubricous coatings (layers) of polyvinylpyrrolidone (PVP) by applying heat and pressure between the film and coatings with heated rollers. PVP is a linear polymer which forms a lubricous coating on the polyurethane when wet. The resultant laminated polyurethane-PVP sheet may then be formed into multiple tubes each of which will serve as an everting tube and has interior and exterior surfaces of PVP. The tubes are preferably sufficiently thin, pliable, and slippery to be used in endoscopy, and yet rugged enough to withstand the puncture forces that are apt to be applied during use.

The PVP surfaces of the laminated tubes are quite lubricous, particularly when exposed to water during emplacement of the liner, thereby facilitating both the emplacement of the tube into the colon or other lumen and the insertion and manipulation of the colonoscope within the tube. The PVP coatings are durable and do not deteriorate or peel off in storage or during use, and because the PVP is laminated to the polyurethane, the everting tubes include no adhesive to possibly harmfully interact with body tissue during use. Although some of the PVP will dissolve in water during use, the lamination procedure embeds sufficient PVP in the polyurethane surfaces to maintain lubricousness throughout the colonoscopic procedure. The durability of the coating (i.e., its resistance to removal by dissolution in the presence of water) can be increased by forming cross-links in the PVP through the application of heat or gamma radiation, as is understood in the art.

The fluid pressure for effecting eversion causes the stored portion of the tubing to collapse upon itself. Without lubrication, the collapsed tubing walls tend to stick to one another with a force that increases with increasing pressure, so that it may be desirable to use tube materials having a low coefficient of friction, or to provide a lubricant that is sufficiently viscous that it is not substantially displaced from the contacting wall surfaces under the pressure of the fluid.

Moreover, the everting fluid itself will preferably have some degree of lubricity to aid in minimizing the friction between the collapsed, not yet everted, inner portion of the tube and the everted outer portion of the tube as the inner portion slides against the outer portion during eversion. The viscosity of the everting fluid is preferably low enough to minimize the pressure drop between the chamber and the everting margin.

For latex tube materials, suitable lubricants for the everting fluid include an aqueous hydrogel such as, for example, K-Y Jelly mixed with water in a proportion as great as about 30% jelly, and preferably between about 1:10 and 1:5. A suitable lubricant for the contacting surface of the collapsed tubing is an aqueous hydrogel such as, for example, K-Y Jelly and water in a proportion at least about 1:2.

An aqueous hydrogel can be suitable for a lubricating everting fluid for a polyurethane tube as well, as described generally in, for example, D. R. Shook et al., 1986, Trans. ASME, Vol. 108, pp. 168-74. More preferably the coefficient of friction of polyurethane tube and/or of the guide/storage tube is reduced by coating the wall surfaces with a hydromer such as, for example, polyvinylpyrrolidone ("PVP"), which has a very low coefficient of friction when wet, as described generally in, for example, D. R. Shook et al., 1986, Trans. ASME, Vol. 108, pp. 168-74.

Other tube materials can be used, such as natural and synthetic rubber, silicone rubber, polyethylenes, segmented polyurethanes, polyolefins such as polyethylene and polypropylene, copolymers of ethylene or propylene and vinyl acetate, polyvinyl chloride or copolymers of vinyl chloride, woven materials, Kevlar, Mylar and the like. The tubing can be reinforced using, for example, materials such as synthetic fibers or threads derived from cotton, silk, nylon, polyester, and the like.

Other lubricants can be used, such as water alone, water containing hydroxyethylcellulose (for example, Natrosol®) or other water "thickeners" such as other cellulose derivatives and glycerin, water containing a surfactant or a mixture of surfactants, or mineral or vegetable oil.

The dimensions of the tube can be selected to adapt the apparatus for any of a wide variety of applications ranging from human adult to human pediatric use, as well as for veterinary uses in any of various mammals. It will be appreciated that the tube can be used to facilitate insertion of any of a wide variety of diagnostic or therapeutic instruments and to facilitate insertion of instruments such as, for example, endoscopes, into any natural or created body passages. A tube having a diameter about ¾ inch and a length at least 80 inches can form an everted tube having a length at least 30 inches when fully everted within the intestine suitable for colonoscopy in an adult human. A shorter tube having a diameter about ¾ inch can form a tube having an everted diameter as described for colonoscopy and an everted length about 12 inches, suitable, for example, to facilitate insertion of a sigmoidoscope.

The length and shape of the sleeve can be quite variable, depending on the application. As shown schematically in FIG. 13E, in an embodiment used as a biliary catheter for an ERCP procedure in an adult patient, the delivery catheter 400 preferably has a side-port for delivery of a sleeve 100 that is preferably tubular and typically measures from 6-10 cm in length, preferably 7-8 cm, so that an inner member (not shown), such as an ERCP scope or a stent, can cannulate both the opening of the common bile duct 1004 at the sphincter of Oddi 1002 and any strictures that may exist therein. Preferably, the sleeve 100 should not be so long that it cannot completely evert during the procedure, since in this particular embodiment, removal of the sleeve 100 is desired after the inner member is in position. An everting sleeve configured to cannulate the biliary tree via the sphincter of Oddi can be especially advantageous, as multiple unsuccessful attempts to cannulate the bile duct via conventional ERCP can increase the risk of complications such as subsequent biliary duct or sphincter stenosis as well as post-ERCP pancreatitis.

Other procedures may require a longer sleeve. For example, the sleeve used to introduce a standard feeding tube, e.g., a nasal-gastric (NG) or nasal-jejunal feeding tube, would be more in the 20-40 cm range, more preferably around 30 cm. The sleeve is used to protect the feeding tube through the nasal passage past the deviation of the septum until it reaches the back of the throat where natural peristalsis takes over and helps to urge the feeding tube downward through the esophagus and into the stomach or jejunum.

A shorter sleeve, e.g., 7-10 cm may be desired for nasal introduction if the inner member is merely serving as a short conduit for the subsequent introduction of another device, such as an endoscope, therethrough. The second device can then be introduced much more comfortably than would be otherwise possible. Conversely, a much longer sleeve, e.g., 150-160 cm, might be used for a colonic procedure. Ideally, the sleeve for a particular application, should be properly sized such that it completely everts from the inner member, if so desired, to allow it to be removed while maintaining the inner member within the patient.

In some embodiments, the toposcopic deployment system includes one or more safety devices designed to reduce the risk of damage, e.g., aneurysm formation or perforation, to the sleeve, body lumen and other associated structures of barotrauma or volutrauma. When delivering a sleeve toposcopically, at least three delivery pressures should be taken into account: (1) the internal sleeve pressure (e.g., when the distal end of the sleeve is tightly sealed); (2) the pressure the distally-advancing sleeve exerts on the wall of the body lumen (e.g., an intestine); and (3) the pressure that might be exerted on the bowel from the inflation media used to evert the sleeve. As described above herein, the distal end of the sleeve is preferably sealed such that all or substantially all of the internal sleeve pressure created by infusion of inflation media within the sleeve is not transmitted to the body lumen outside of the sleeve. By successfully sealing the sleeve, preferably no pressure should be exerted on the bowel from the inflation media used to evert the sleeve. The internal sleeve pressure is preferably below the pressure required to deform the sleeve, as deformation of the sleeve (e.g., aneurysm formation) can undesirably allow transmission of pressure to the body luminal wall, such as via direct contact between the sleeve aneurysm and the body luminal wall, which can in turn cause damage to the body luminal wall. While the deformation pressure of the sleeve depends on a variety of factors, including the material and dimensions of the sleeve, in some embodiments, it is desirable to maintain the internal sleeve pressure at no more than about 10, 9, 8, 7, 6, 5, 4.5, 4, 3.5, 3, 2.5, 2, 1.5, 1 psi, or less. The use of a mechanical assisting device, such as a push wire or snare, as described further below, can enable the use of a lower eversion pressure than would have otherwise been required to provide a given net distal force on the inside of the toposcopic sleeve. One point in which this can be especially advantageous is when the inverted sleeve needs to overcome the frictional force of the filling catheter against the sleeve to promote eversion of the sleeve.

The distally-advancing sleeve can also exert a pressure on the body lumen when, for example, the sleeve contacts a wall of the body lumen. One specific example is when the sleeve navigates around a sharp turn or bend in the lumen, such as an intestinal wall. Deploying the sleeve at a high velocity, which may occur when the sleeve is filled with inflation media at a high pressure, can increase the pressure transmitted from the sleeve to the luminal wall, causing complications such as bleeding, if a vessel is contacted, or perforation. Furthermore, a deformed portion of the sleeve (e.g., a sleeve aneurysm) could also come into direct contact with the body lumen wall, causing damage. Perforation of a body lumen such as the intestine may cause life-threatening peritonitis caused by translocation of gut flora into the sterile peritoneal cavity, often necessitating emergent surgical repair. Therefore, it is desirable to keep the pressure exerted by the sleeve on the wall of the body lumen to a pressure less than the pressure required to deform the body luminal wall (e.g., the aneurysm pressure), which may be, in some cases, no more than about 4, 3.5, 3, 2.5, 2, 1.5, 1 psi, or less. Safety devices that will mechanically assist in reducing the net pressure the sleeve exerts on the body lumen, such as control wires and grasping devices such as loop snares are disclosed herein. In some embodiments, the safety device, such as a control wire can function as a "brake" to reduce the velocity of the distally advancing sleeve by providing a proximally retracting force on the sleeve, which in turn will reduce the net pressure the sleeve exerts on the luminal wall when the sleeve comes into contact with the luminal wall. The safety device, e.g., a control wire can also mechanically assist in eversion of the sleeve, reducing the internal sleeve pressure and thus reducing the risk of sleeve deformation that could in turn transmit pressure to the body luminal wall by direct contact, or alternatively by the inflation media if the sleeve actually ruptures.

In some embodiments, it may be desirable to provide mechanical assistance to supplement the deployment force provided by the inflation media, to evert the sleeve, or alternatively to provide a proximally retracting force on the sleeve in some embodiments. Such a control wire may have pushing and/or pulling capabilities with respect to the sleeve. In some embodiments, mechanical assistance can be conveniently provided by axially distally advancing a push wire or other pushable structure, inside of the sleeve as the sleeve everts. The push wire may comprise any of a variety of structures having sufficient flexibility to navigate the GI pathway, and sufficient pushability to exert a distally directed force on a distally advancing aspect of the sleeve. The net distal force on the distally advancing end of the sleeve will be the sum of the force attributable to the inflation media, and the force attributable to the push wire if one is used. The use of a push wire thus enables the use of a lower eversion media pressure than would have otherwise been required to provide a given net distal force on the inside of the toposcopic sleeve. This can be especially advantageous, for example, at the start of the eversion process when the sleeve is inverted within the filling catheter, and the sleeve needs to overcome the frictional force of the filling catheter against the sleeve to promote eversion of the sleeve.

The control wire, which may be a push wire, may be configured in either of two basic forms. In one, a distal end of the push wire is advanced against the inside surface of distal end 154, as it advances distally. In this configuration, the distal end of the push wire is in sliding contact with the inside surface of the sleeve, and is preferably provided with a blunt tip as well as a low friction surface or coating. In an alternate configuration, the push wire is attached to the distal end 112 of the sleeve, and is advanced distally along with the eversion of the sleeve. Preferably, the push wire is releasably attached to the sleeve, so that it may be released and removed following full deployment. This may be accomplished, for example, by the provision of a releasable connector such as an erodable bond, releasable snap or other interference fit structure, or a push wire having a distal grasping member such as a snare for grasping the distal end 112. In some embodiments, the push wire is releasably attached to the sleeve but does not reside within the lumen of the sleeve along its length. The push wire can be housed, for example, within a separate lumen in the filling catheter in these embodiments.

In one implementation, the control wire includes a grasping member can be a semi-rigid elongate member, such as a snare, and configured to provide a mechanical force on an inverted distal end of the sleeve to promote eversion, (or to promote elongation if an axially compressed accordion-like sleeve is utilized). The grasping member can also be utilized to invert the sleeve prior to eversion. The grasping member can be used in combination with, or a substitute for inflation media used in everting a sleeve, as described elsewhere in the application.

Use of a grasping member in combination with inflation media for eversion of a sleeve can advantageously allow for use of a lower inflation media pressure and/or volume as some of the force can be provided mechanically by the eversion-assisting member. Furthermore, using the grasping member to function as a "brake" to reduce the velocity of the distally advancing sleeve by providing a proximally retracting force on the sleeve, can advantageously reduce the net pressure the sleeve exerts on the luminal wall when the sleeve comes into contact with the luminal wall, as described above. As noted, maintaining the internal sleeve pressure at a pressure below the deformation pressure of the sleeve, as well as keeping the pressure the sleeve exerts on the wall of the body lumen at a pressure below the deformation pressure of the wall of the body lumen can reduce the risk of barotrauma or volutrauma to the sleeve, body lumen, or other structure which in turn can undesirably lead to complications such as aneurysm formation or perforation.

In some embodiments, the grasping member is a loop snare. Other grasping members as known in the art such as forceps, jaws, clamps, and the like can also be used. The snare can be made of any appropriate material known in the art. In some embodiments, the snare may be made of a metal such as stainless steel. In other embodiments, the snare may be made of nitinol or a shape-memory polymer.

Figure 14A:
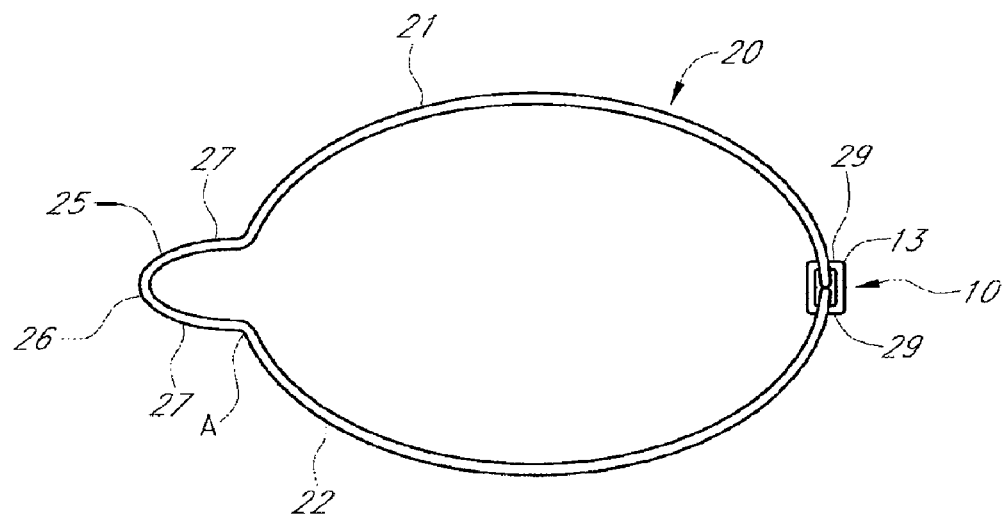
FIG. 14A is a top view of a loop snare that can be utilized during toposcopic delivery, according to one embodiment of the invention.
Figure 14B:
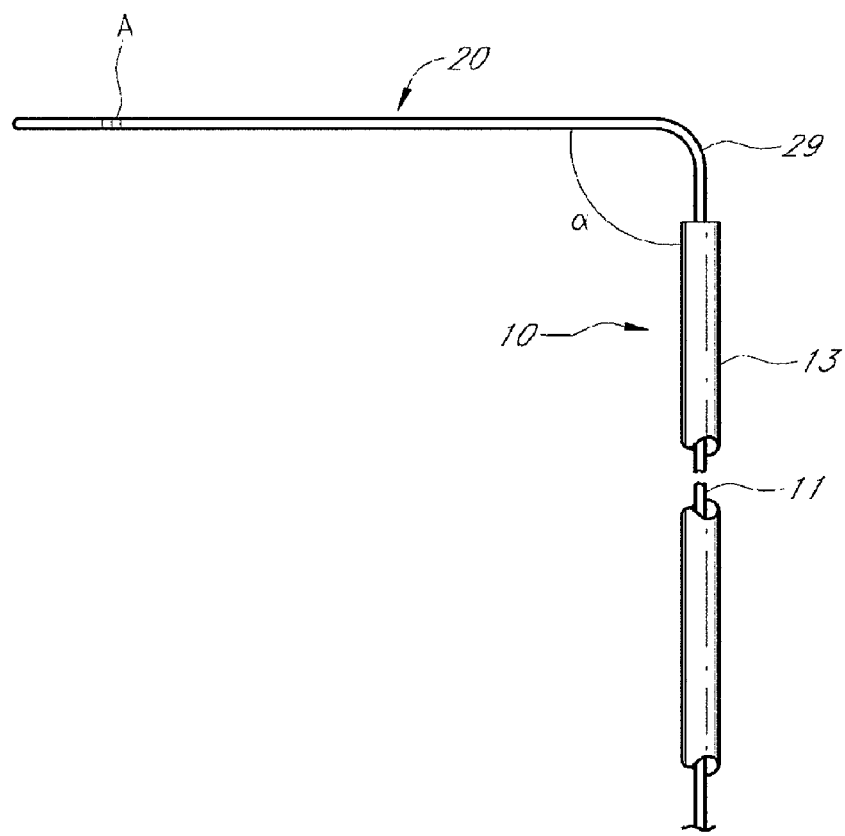
FIG. 14B is a side view of the loop snare in FIG. 14A, better illustrating the proximal portion of the snare.

FIGS. 14A and 14B show top and side views, respectively, of one embodiment of a loop snare that can be utilized to facilitate toposcopic delivery of a sleeve. The snare includes a proximal member 10 and a distal segment 20. The distal segment 20 includes a loop formed of an appropriate material, such as a metal, for example, a superelastic alloy wire. Although the loop may be of any useful shape, it is desirably generally either circular or elliptical in shape. While an axis of the loop may be parallel to the long axis of the proximal member 10, it is preferred that an axis of the loop is not parallel to the axis of the adjacent portion of proximal member 10 and, in some embodiments, it is substantially perpendicular thereto. When the loop is deformed and inserted into the proximal end of a catheter, this axis will generally coincide with the axis of the proximal member.

Adjacent the ends of the loop, the two sides of the loop can gradually taper away from the axis. This makes initial insertion of the device into a catheter easier than if the two sides of the loop diverged from one another more sharply. As the device is entered into the lumen of the catheter, once a small portion of the loop has entered the lumen, the catheter walls will easily collapse the rest of the loop about the axis so that the two sides of the loop are held close to one another within the catheter lumen.

In a preferred embodiment, the distal segment 20 includes a distal tip 25 which facilitates entry of the loop into the proximal end of a catheter. Desirably, the tip includes a generally U-shaped arch 26 at its distal end with each leg 27 extending rearwardly toward the loop from a side of the arch. These legs may be substantially parallel, as shown, or they may taper slightly away from one another. Although the legs could also taper toward one another away from the arch without any significant loss in utility, this embodiment is generally not preferred because then the transition from the tip to the loop is more abrupt. Desirably, this transition is fairly gradual, with the legs of the tip meeting the respective sides of the loop at an obtuse angle. This makes insertion of the snare into the catheter easier because there is no sharp bend in the wire to impede entry.

The loop and the distal tip desirably lie generally flat in a single plane, as shown, but the major axis of the loop may instead be curved. If such a curved configuration is utilized, it is preferred the apex of the curve be disposed away from the proximal end of the device.

In the substantially planar embodiment illustrated in FIGS. 14A and 14B, the axis of the proximal member 10 meets the plane containing the loop at an angle alpha which in some embodiments is between about 45-135 degrees. An angle of about 90 degrees may present the full area of the loop in a distal direction, enhancing the ability to slip the loop over tail members 801 on the distal end 112 of the sleeve 100 (not shown). This angle alpha is provided between the loop and the proximal segment by forming bends 29 in the wire 21 of the loop at a position adjacent the distal end of the proximal member 10. These bends 29 are desirably generally rounded, yet provide the desired angle in a relatively short distance.

Figure 14C:
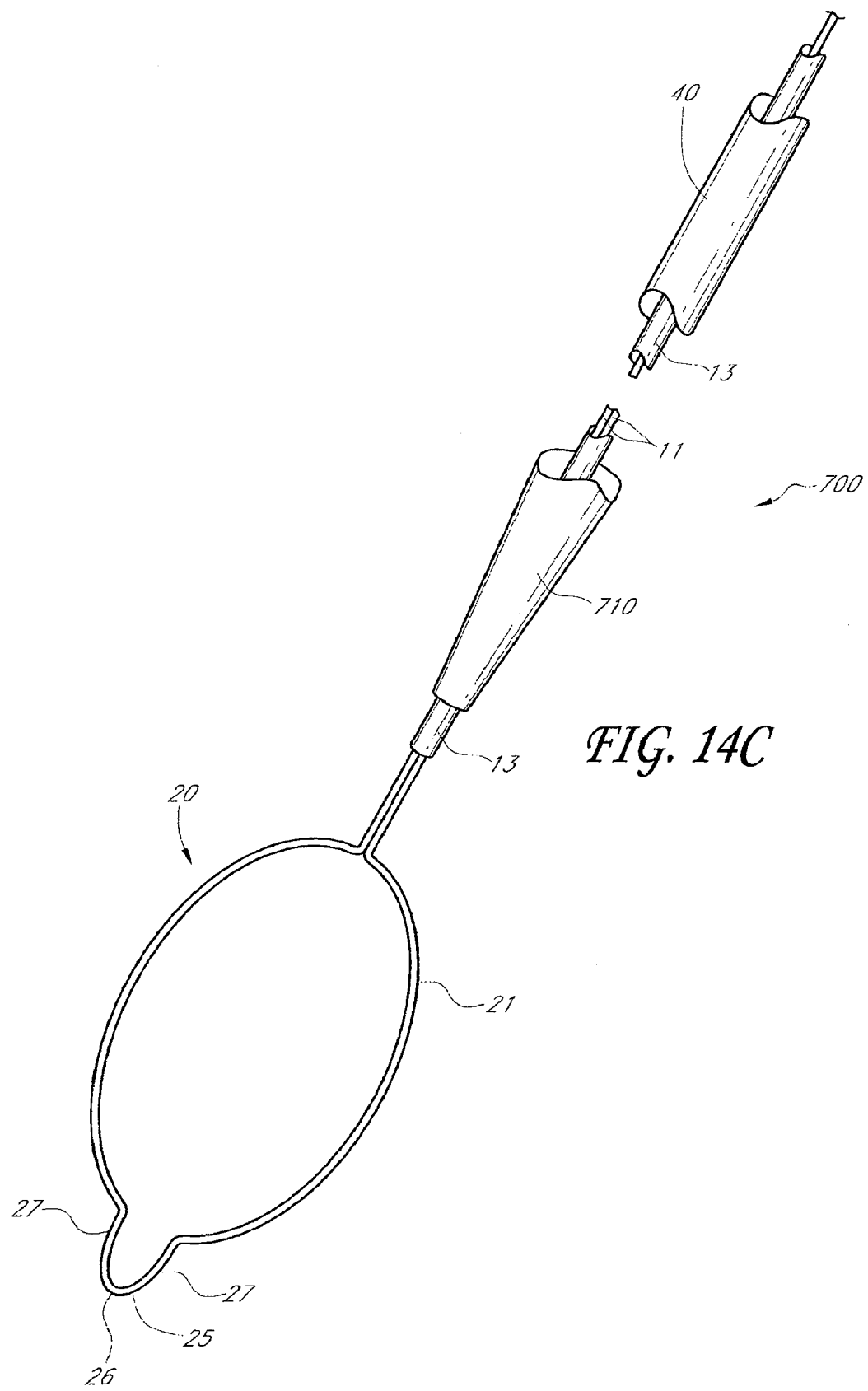
FIG. 14C schematically illustrates another embodiment of a loop snare, according to one embodiment of the invention.

FIG. 14C schematically illustrates the loop snare 700 in a perspective view, as well as better illustrating various features of the snare 700. In contrast to the embodiments depicted in FIGS. 14A-14B, the loop snare 700 depicted in FIG. 14C shows the proximal member 10 substantially coaxial with the distal member 20, which could advantageously minimize the profile of the snare while in use. The proximal member 10 can comprise a single, elongate member which extends proximally from these bends 29 and is secured thereto. In a preferred embodiment, the proximal member 10 comprises two parallel wire segments 11 that are gripped together, or bonded to, one another. Desirably, these two wire segments 11 are extensions of the single wire 21 defining the loop. The two wires 11 may be bonded or gripped together by any convenient means to avoid relative axial movement therebetween. Inasmuch as shape memory alloys are often relatively difficult to braze or solder, an organic adhesive, such as an epoxy resin, is preferred. The proximal member 10 may also include an outer sheath 13 carried about these two wire segments 11 to reduce friction between the proximal member 10 and the lumen of the catheter as the snare is passed therethrough. The sheath 13, which may serve to grip together the wire segments 11, may cover substantially the entire length of the proximal member 10, or it may terminate at a position spaced away from the proximal end of this member 10, as desired. Preferably, the wall of the sheath 13 is very thin, e.g., on the order of about 0.002-0.010 inches in thickness, to keep the outer diameter of the entire proximal member 10 small; this allows use of the loop snare with catheters of smaller inner diameter. Shrink wrap tubing of polytetrafluoroethylene or the like may be employed to form the sheath 13. After the wires 11 are passed through the shrink wrap tubing, the tubing may be heated to cause it to shrink into tight engagement with the wire segments 11. Catheter 40 circumscribes proximal member 10 and is configured such that relative movement between the catheter 40 and the proximal member 10 and distal portion 20 of the snare 700 allows for releasable grasping of, for example, distal tails of a sleeve to promote inversion or eversion of the sleeve.

In some embodiments, the distal portion 710 of the catheter 40 (tubing surrounding the snare wire(s)) is tapered as shown schematically in FIG. 14C to increase flexibility of the snare 700, such that it can more easily navigate turns and bends within a body lumen. In some embodiments, no more than about 5 cm, 10 cm, 15 cm, 20 cm, or 25 cm of the distal tubing portion 710 is tapered such that the radial thickness of the distal tubing 710 gradually decreases distally.

In some embodiments, the snare may be as described or modified from U.S. Pat. No. 5,171,233 to Amplatz et al. or U.S. Pat. No. 6,913,612 to Palmer et al., which are both incorporated by reference herein in their entirety.

Figure 14D:
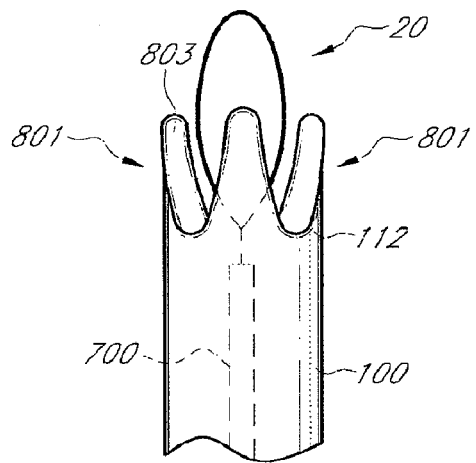
FIGS. 14D-14F depict a method of creating a seal at the distal end of a sleeve by sequentially folding down a plurality of distal tail elements using a loop snare, according to one embodiment of the invention.
Figure 14E:
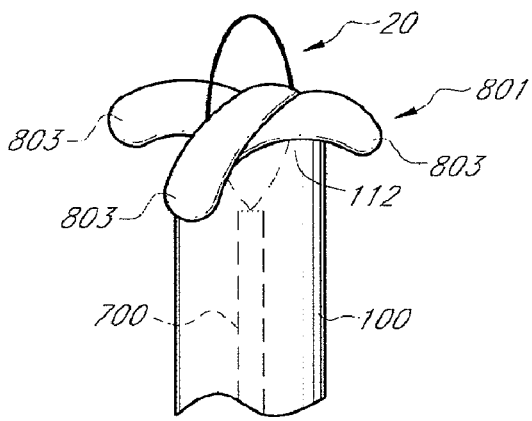
Figure 14F:
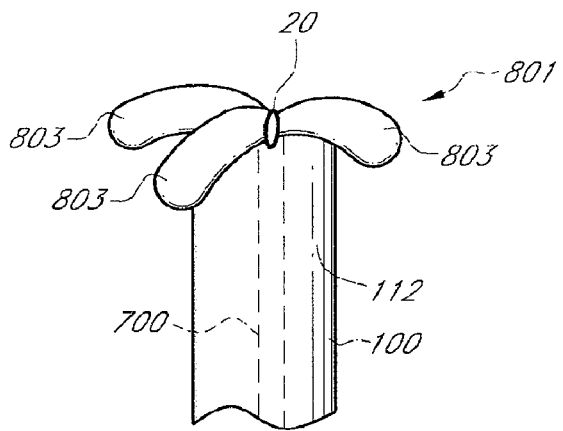
Figure 14G:
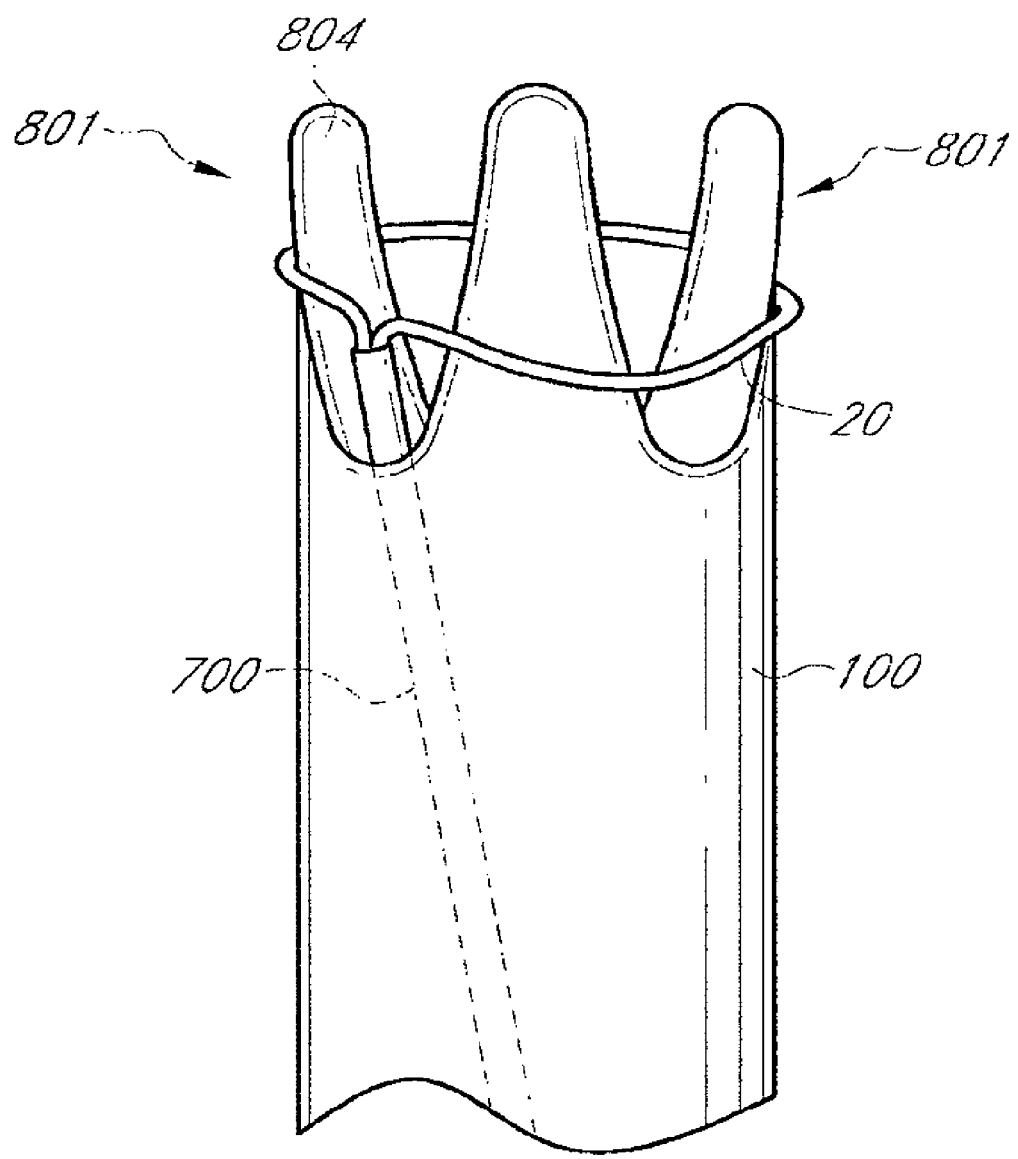
FIGS. 14G-14H illustrate another method of creating a seal at the distal end of a sleeve using the elements shown in FIGS. 14D-14F.
Figure 14H:
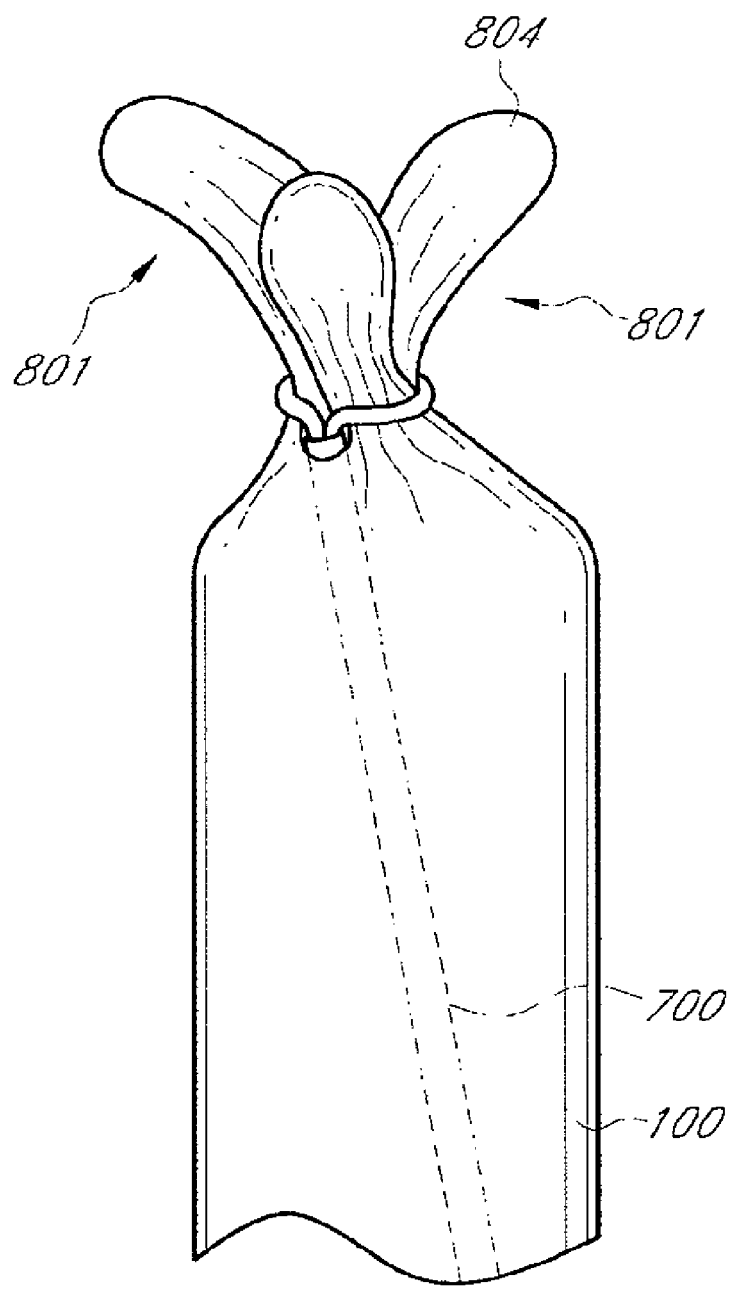

A grasping member such as a loop snare can be used to form a seal with respect to the distal end of a sleeve as follows. In FIG. 14D, a sleeve 100 as shown in FIG. 1C with a plurality of distal tail members 801 is illustrated with the distal portion 20 of loop snare 700 extending distally out from the lumen of the sleeve 100. The distal portion 20 of snare 700 is then actuated to sequentially fold down each tail member 801, such as at its distal end 803 such that the tail members 801 overlap, such as piled on top of one another as shown, preferably in an axis that is substantially orthogonal to the long axis of the sleeve 100, as shown in FIG. 14E. The loop 20 of the snare 700 can then be cinched such that the tail members 801 and the loop of the snare 20 form a fluid-tight or near fluid-tight seal at the distal end 112 of the sleeve 100, as shown in FIG. 14F. the sleeve can be pinned between the loop 20 and the distal tip of the snare loop catheter 40. The cinching be performed by either (1) retracting one strand of the folded wire, making the loop smaller, or (2) relative movement between the wire and the catheter, such as by advancing the catheter over the wire until it closely contacts the ensnared distal tail members 801. The snare 700 can then be retracted proximally to invert the sleeve 100 within a delivery catheter for later eversion, as will be shown in FIGS. 15A-G below. In other embodiments, rather than the loop 20 of snare 700 sequentially folding down each tail member 801 individually to form a seal over the distal end 112 of the sleeve 100 as shown in FIG. 14E, the tail members 801 may all be secured simultaneously using the loop 20 of the snare 700, as shown in FIGS. 14G-14H.

Figure 15A:
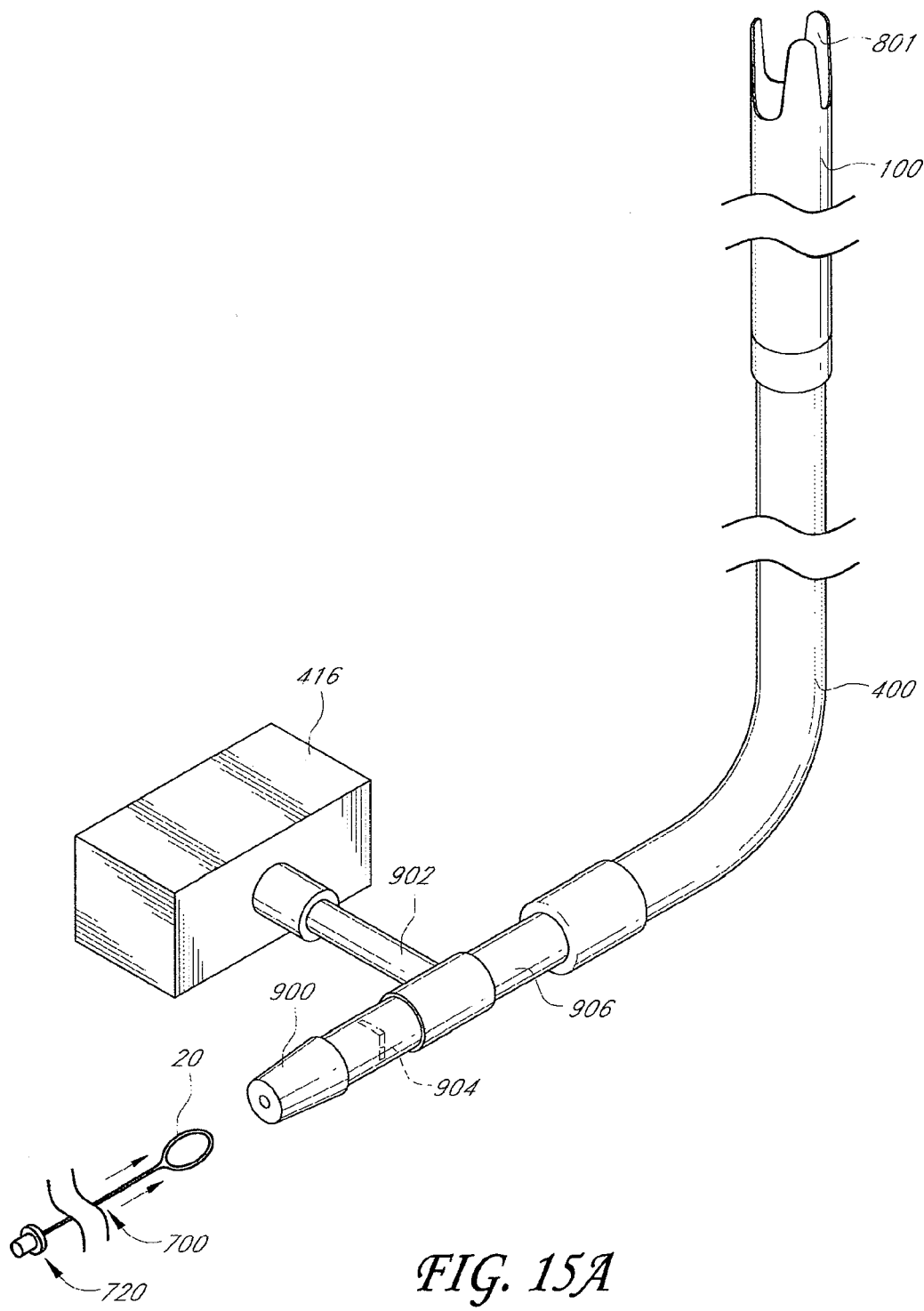
FIGS. 15A-15G schematically illustrate a sleeve being inverted within into a toposcopic delivery system using a grasping element, according to one embodiment of the invention.

A method of using a loop snare within a delivery system to facilitate toposcopic delivery of a sleeve will now be described, and illustrated in connection with schematic FIGS. 15A-16B. FIG. 15A is a schematic perspective view of a toposcopic delivery system. Shown is the distal portion 20 of the snare 700 about to be threaded through a lumen in a port 900 of a connector, such as the T-connector 906. Other connectors, such as Y-connectors can also be utilized. Snare 700 also has a proximal control element 720 such as a handle to facilitate movement of snare 700 as well as to facilitate relative movement of snare catheter 40 (not shown) relative to distal loop 20 to engage distal tail members 801 of the sleeve 100. The inflation media control element 416 is shown operably connected to the lumen of T-connector 906 via port 902. A valve 904, which is preferably a one way valve 904 prevents backflow of inflation media through port 900. Proximal end of sleeve 100 is operably connected to the distal end of the filling catheter 400 as described elsewhere herein.

Figure 15B:
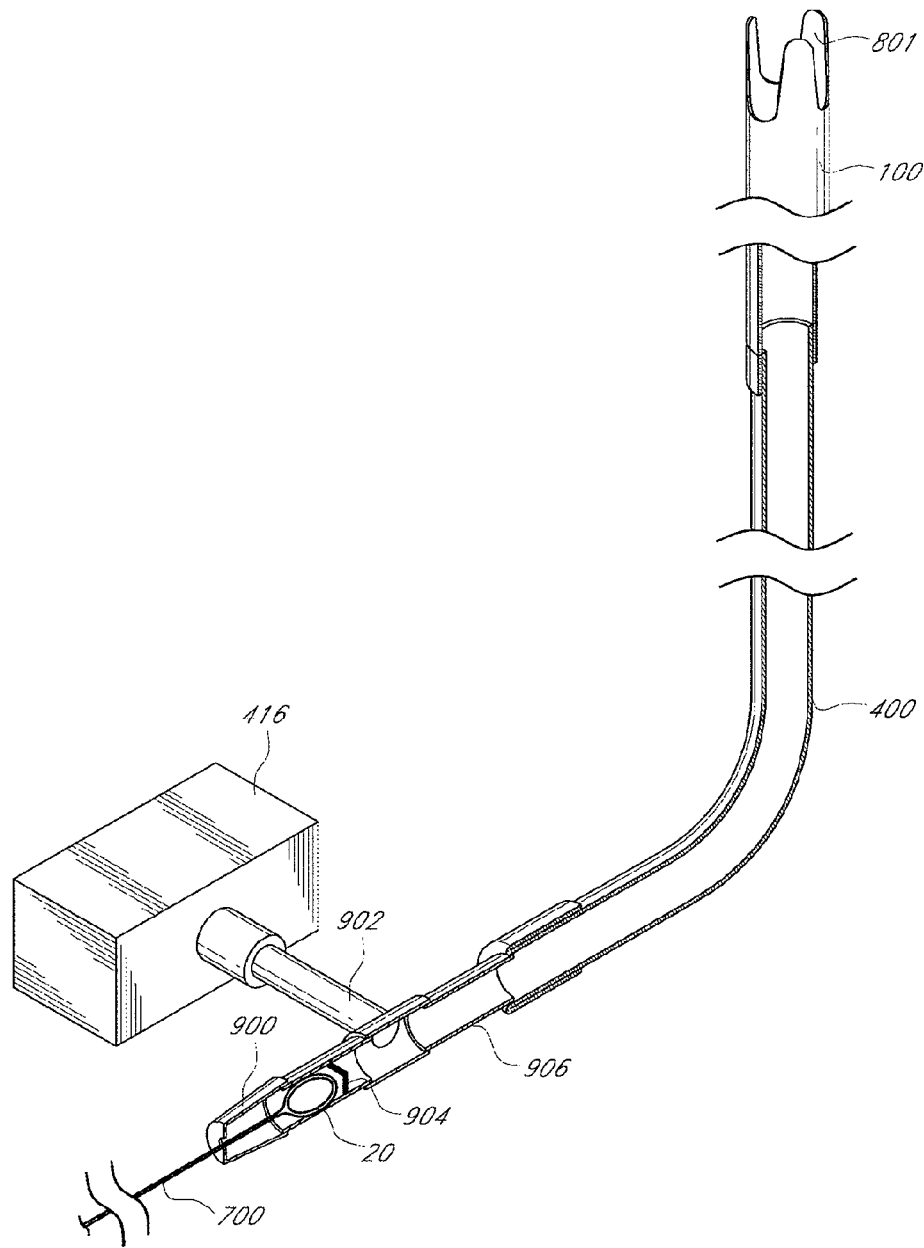
Figure 15C:
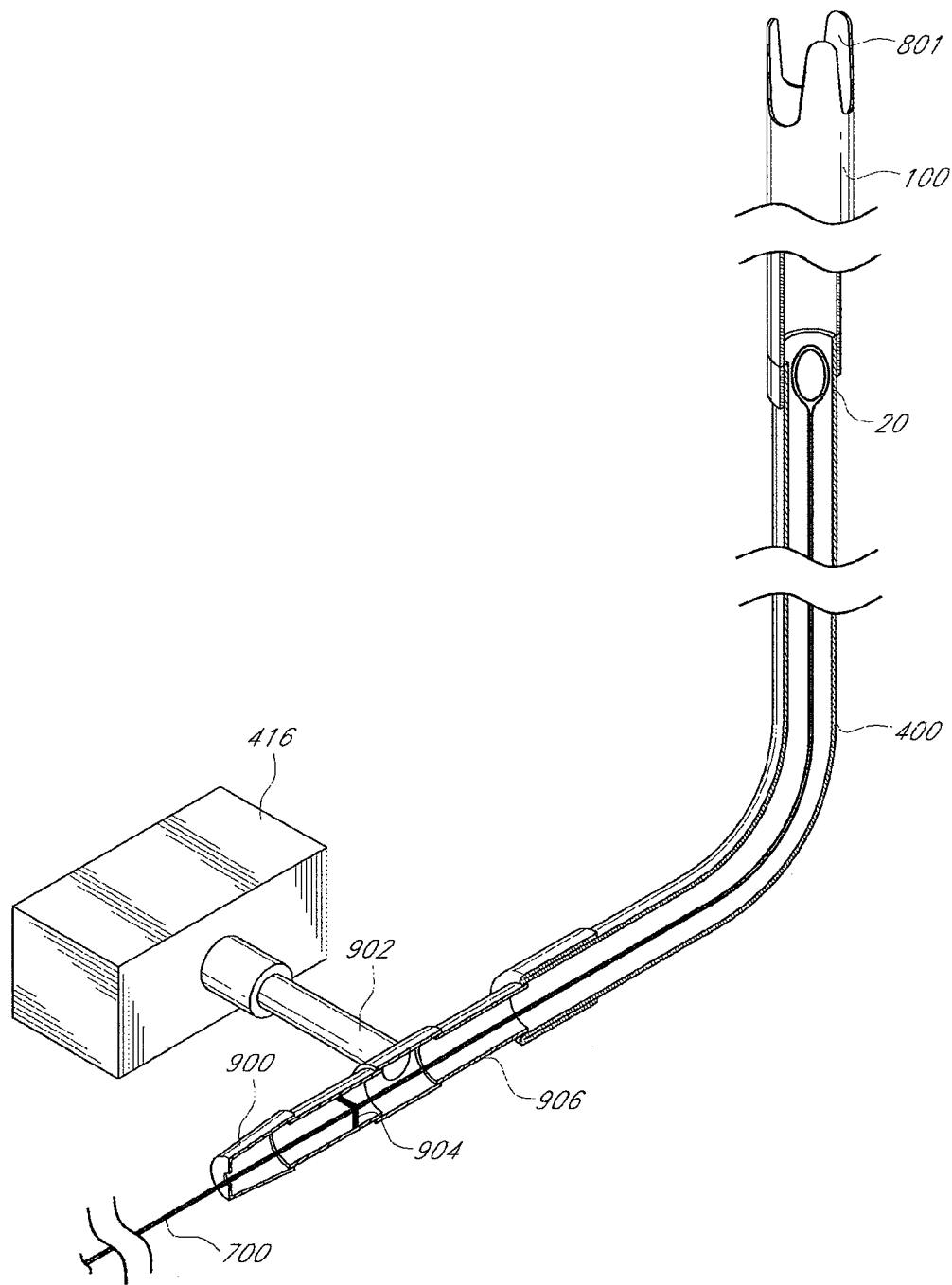
Figure 15D:
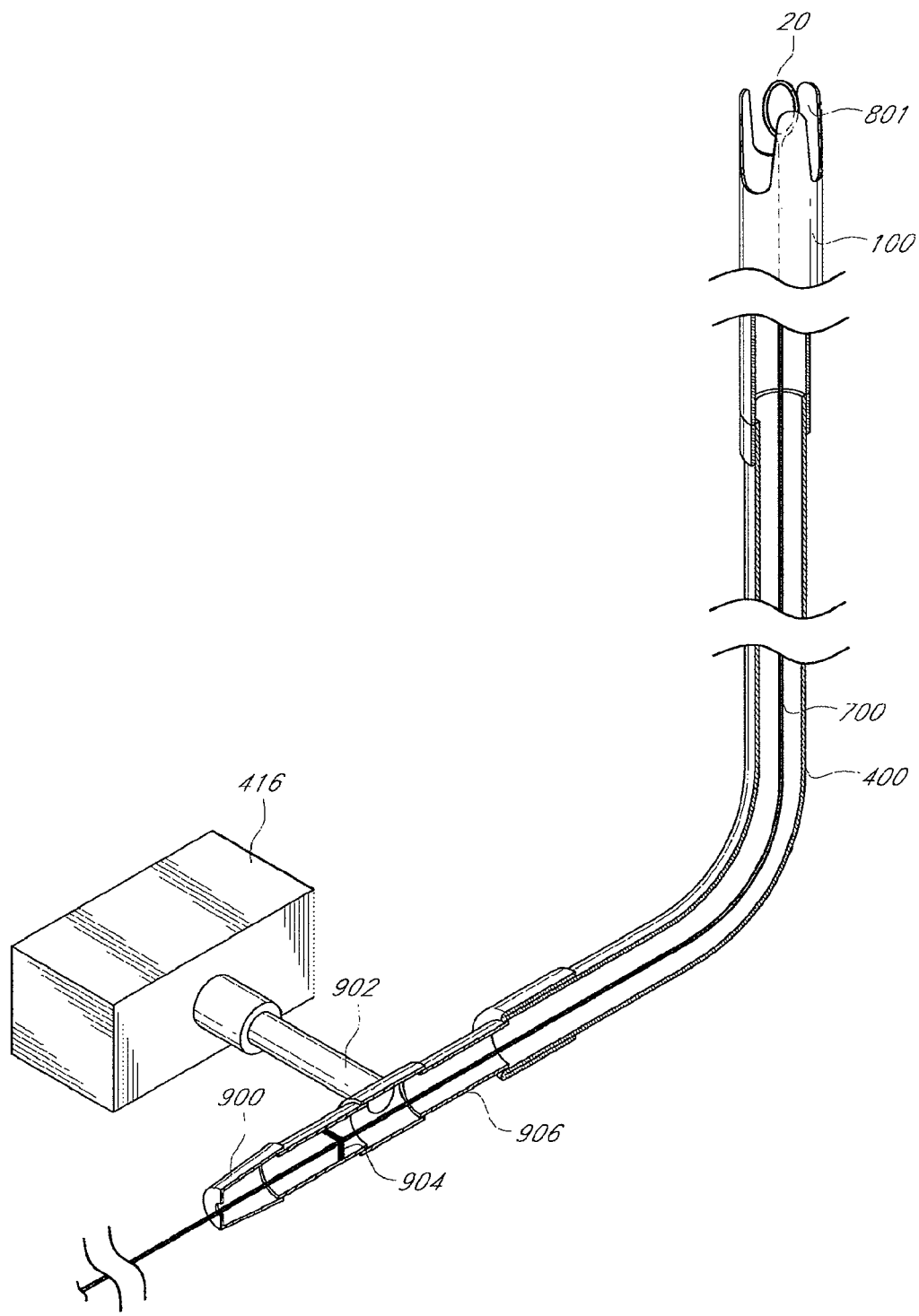
Figure 15E:
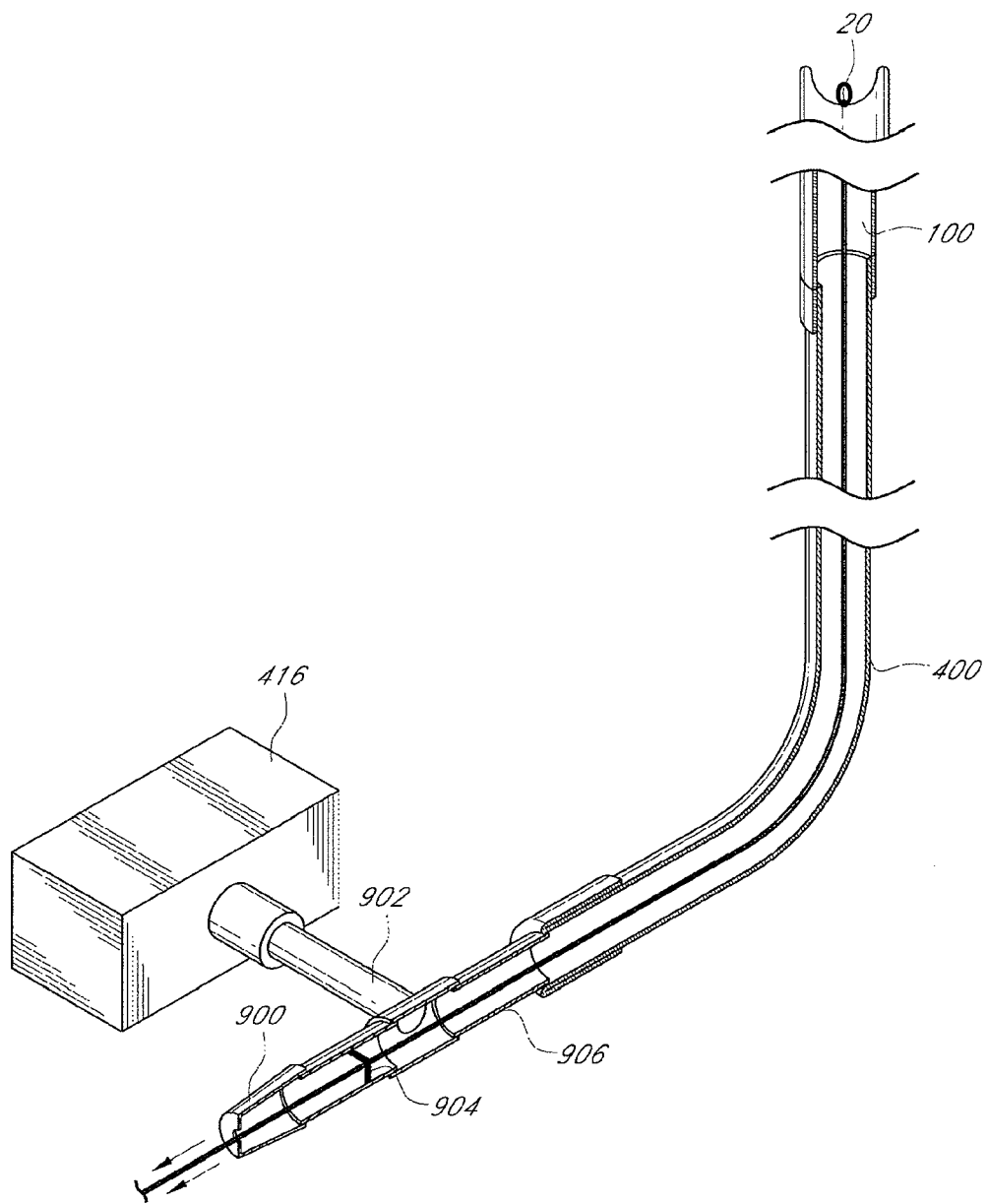
Figure 15F:
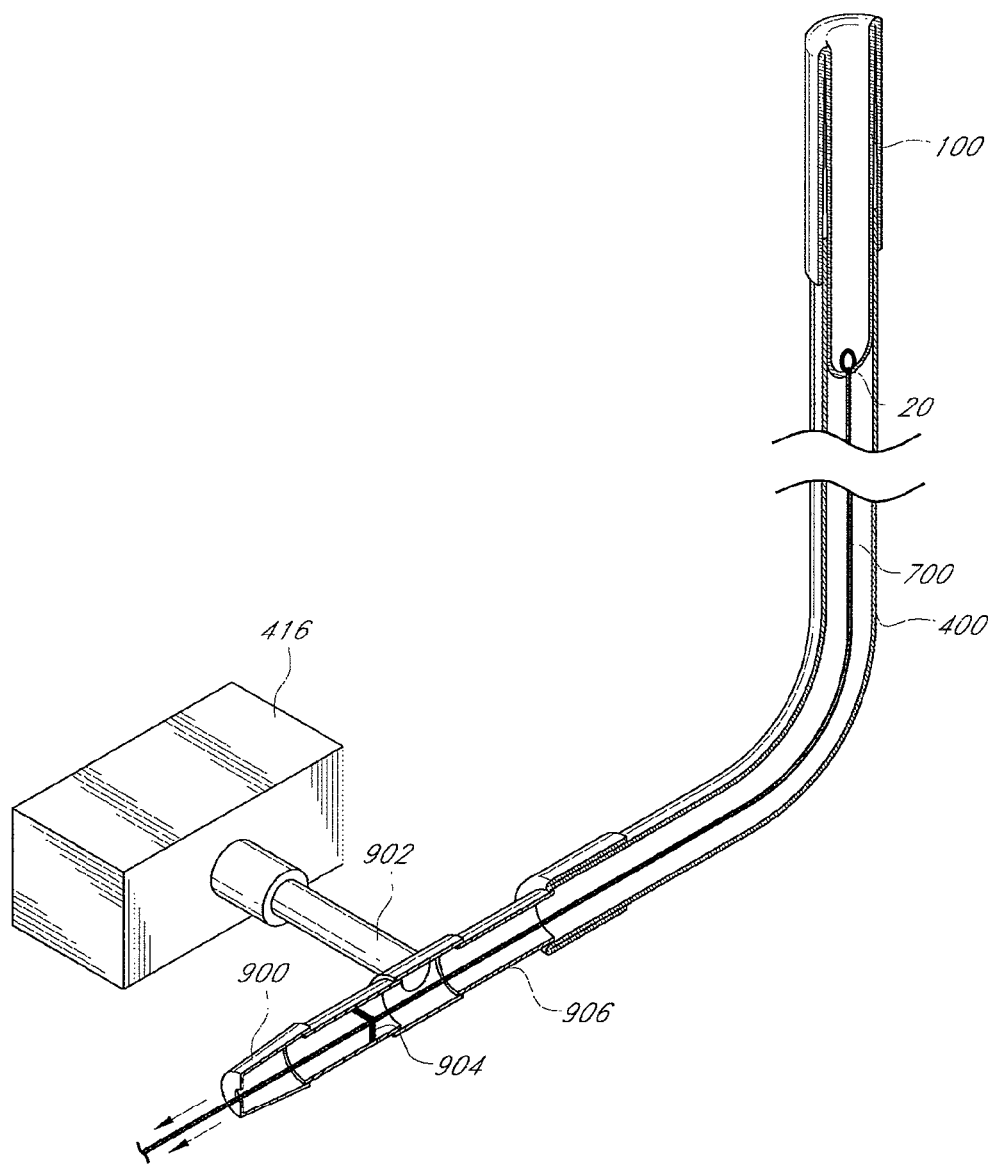
Figure 15G:
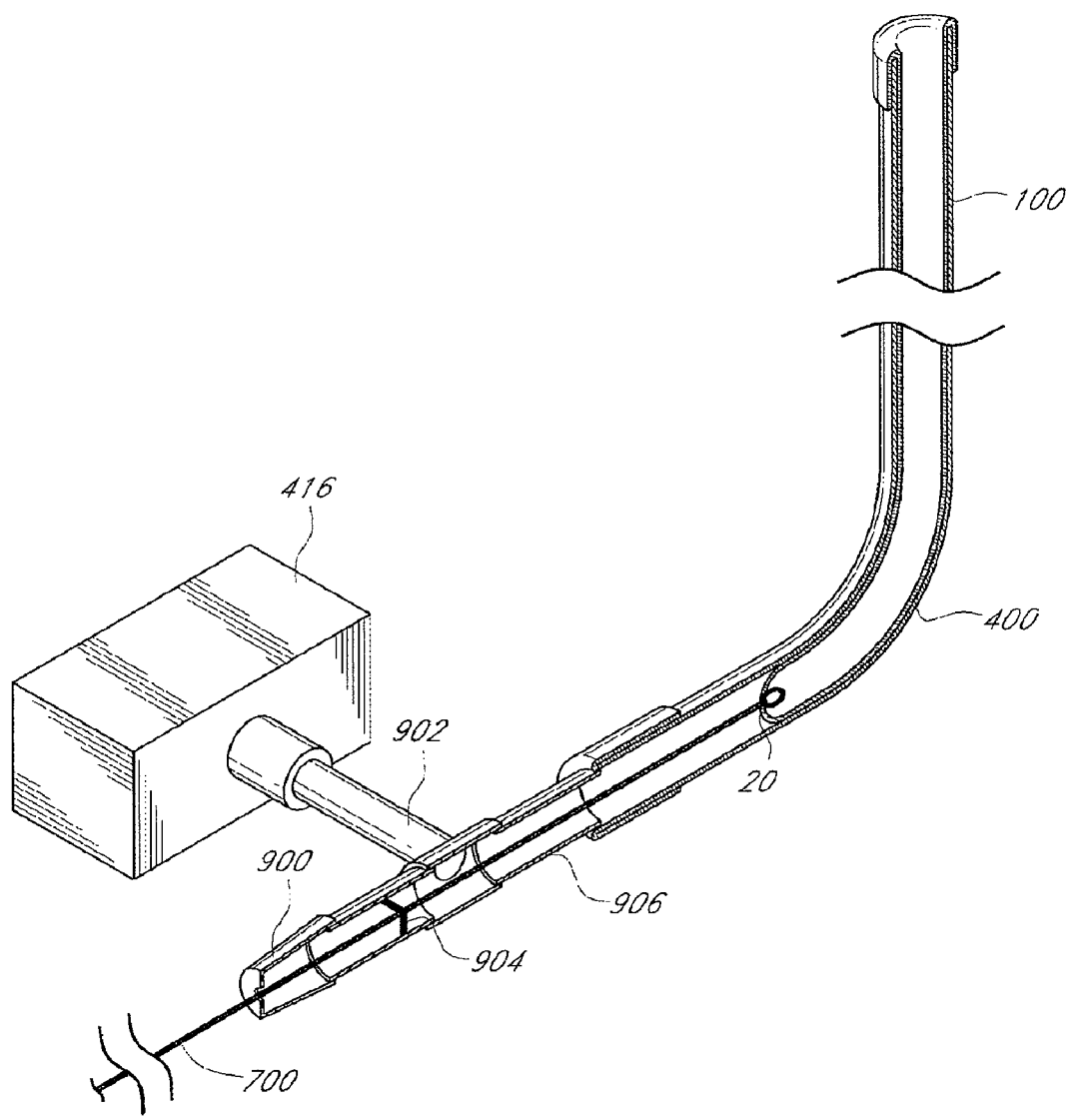

FIG. 15B is a cut-away schematic view of the toposcopic delivery system shown in FIG. 15A, and illustrating distal portion 20 of the snare 700 through port 900 and about to be threaded through one-way valve 904. As shown in FIG. 15C, snare 700 is threaded further distally into the filling catheter 400. Next, as shown in FIG. 15D, the snare 700 is threaded through the sleeve 100, and the snare loop 20 emerges distal to the tail members 801 of the sleeve 100. Next, the tail members 801 of the sleeve 100 are engaged with the snare loop 20 and a seal is formed as illustrated and described, for example, in connection with FIGS. 14D-14F. The snare 700 can then be retracted proximally while operably engaging the distal tail members 801 (no longer shown for clarity) in order to invert the sleeve 100, as shown in FIG. 15E. FIGS. 15F-G illustrates the snare 700 further retracted proximally such that the sleeve 100 is inverted within the filling catheter 400. The filling catheter 400 can then be delivered to a patient in preparation for eversion of the sleeve 100, as previously described.

Figure 15H:
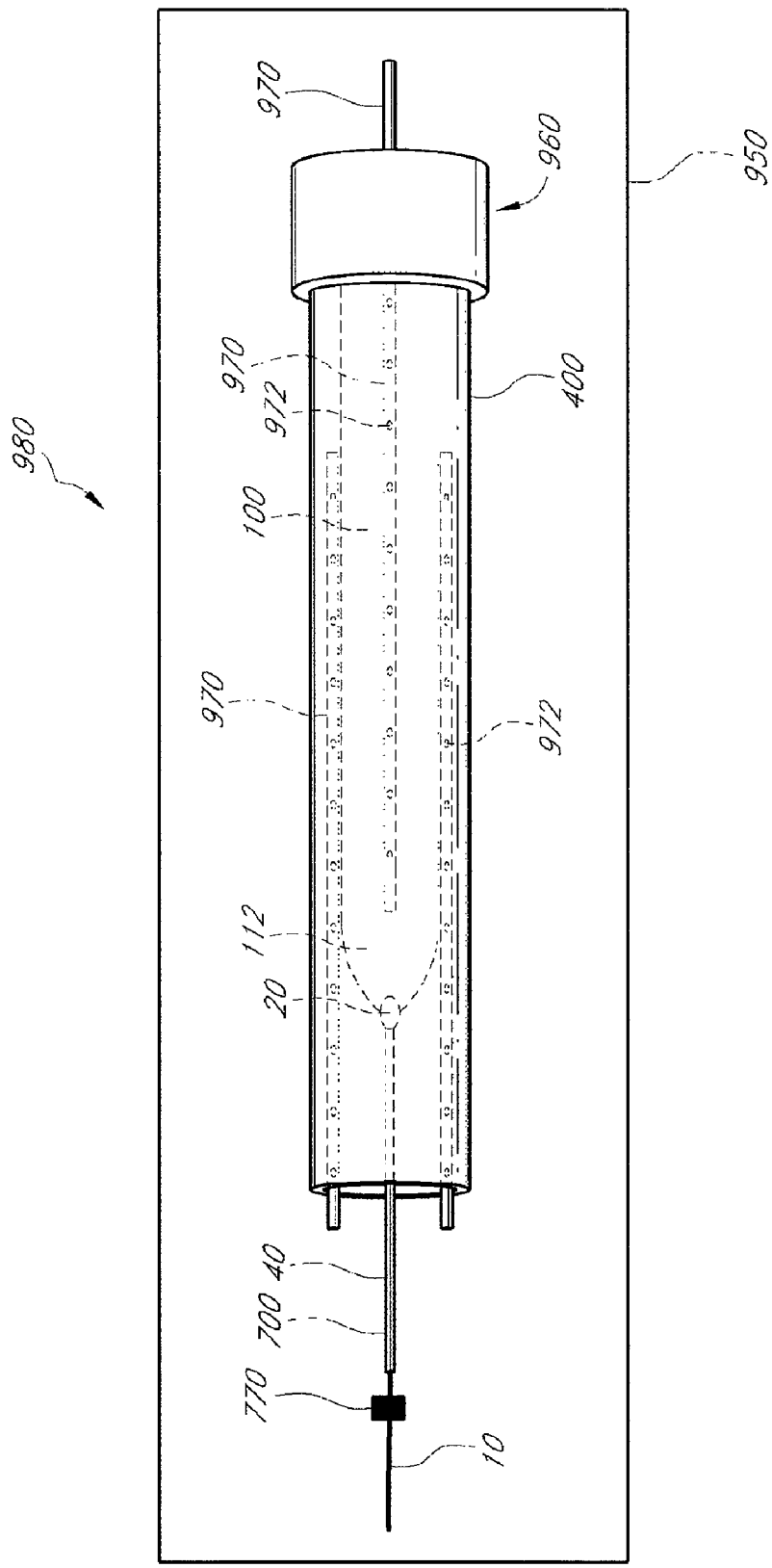
FIG. 15H schematically illustrates a filling catheter and sleeve kit, according to one embodiment of the invention.

FIG. 15H is a schematic illustration of a sleeve and filling catheter kit 980, with the sleeve 100 inverted within the filling catheter 400, and the proximal end of the sleeve operably connected with the distal end of the filling catheter at 960. Control wire, such as the loop snare 700 previously described with a proximal catheter portion 40, can be operably attached at its distal end 20 to the distal end 112 of the sleeve 100. The snare 700 may also have a releasable proximal element, such as a clamp 770 to maintain the snare wire 10 in place relative to the filling catheter 400. Hydration tubing 970 preferably is in proximity to or abuts the sleeve as shown. Hydration tubing 970 preferably has pores or weep holes 972 to facilitate hydration of the sleeve 100 to assist in the eversion process.

The assembly 980 is preferably contained within packaging 950 in a sterile manner. The sleeve inversion process can occur, for example, as described in connection with FIGS. 15A-G above, and can be especially convenient and time-saving as the sleeve inversion process need not be performed in the operating room immediately prior to toposcopic delivery in a patient.

In one embodiment, the kit 980 can be used in the following manner. After removal of packaging 950, fluid, such as water or saline, can be delivered through hydration tubing 970 to hydrate the sleeve 100 in preparation for eversion. Next, the control wire 700 including clamp 770 can be back-loaded through inflation media device connector 906 in a retrograde direction, and out port 900 (elements shown, e.g., in FIG. 15A, except delivery catheter 400 is not yet attached to connector 906). In embodiments where the control wire 700 is a grasping member, the clamp 770 can then be removed and replaced by a control handle to facilitate relative movement of grasping catheter 40 with respect to distal grasping portion 20. The filling catheter 400 can then be attached to connector 906 of inflation media control system and deployed to a body lumen of the patient as described, for example, below. The control wire 700 may then be removed, or retained for use as, for example, a guidewire.

Figure 16A:
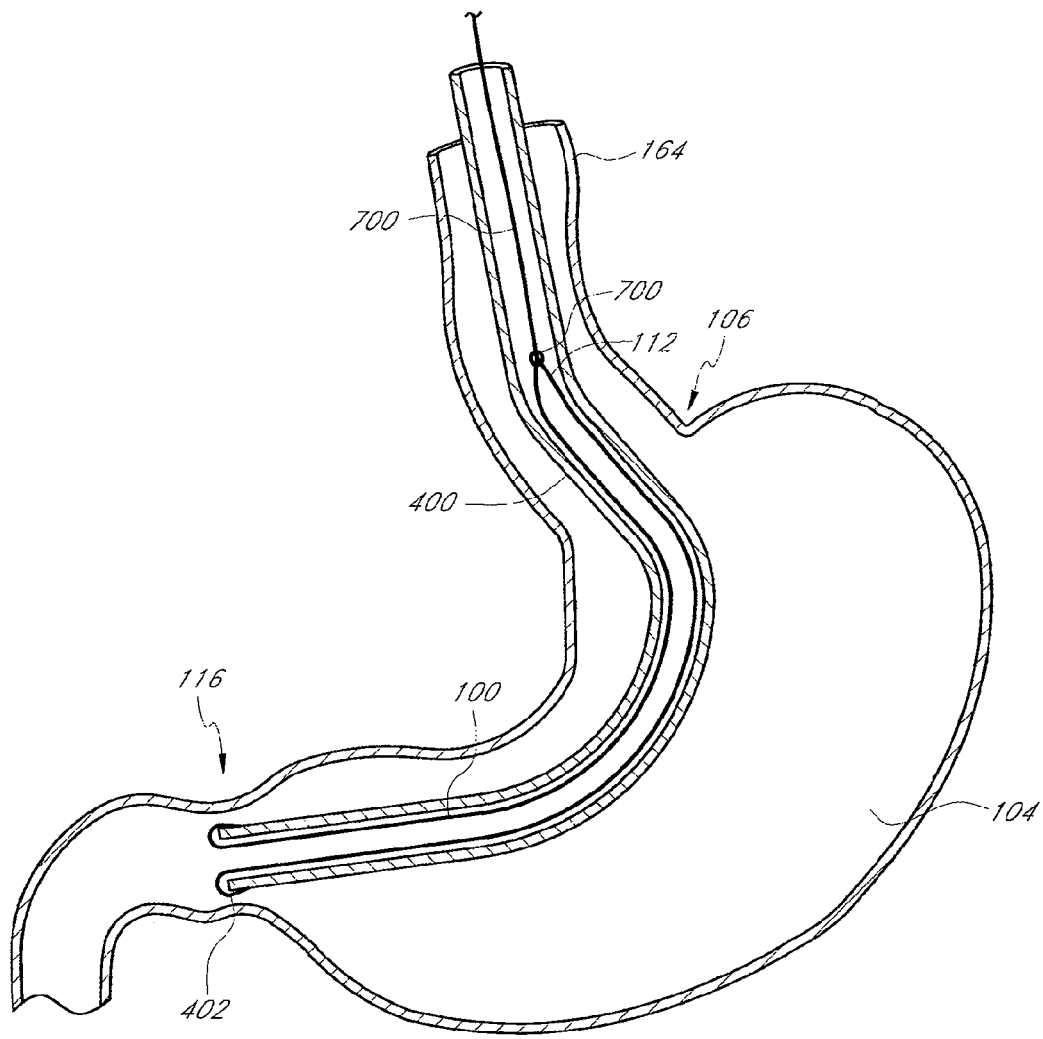
FIGS. 16A-16B illustrate a toposcopic delivery system including a snare in accordance with the present invention, for delivering a sleeve to a remote treatment site.

Referring to FIG. 16A, there is illustrated a delivery system in accordance with the present invention. The delivery system includes a filling catheter 400, illustrated as extending across the stomach such that a distal end 402 is in the vicinity of the pylorus 116. A toposcopic sleeve 100 is proximally retracted within the filling catheter 400 as has been discussed.

Figure 16B:
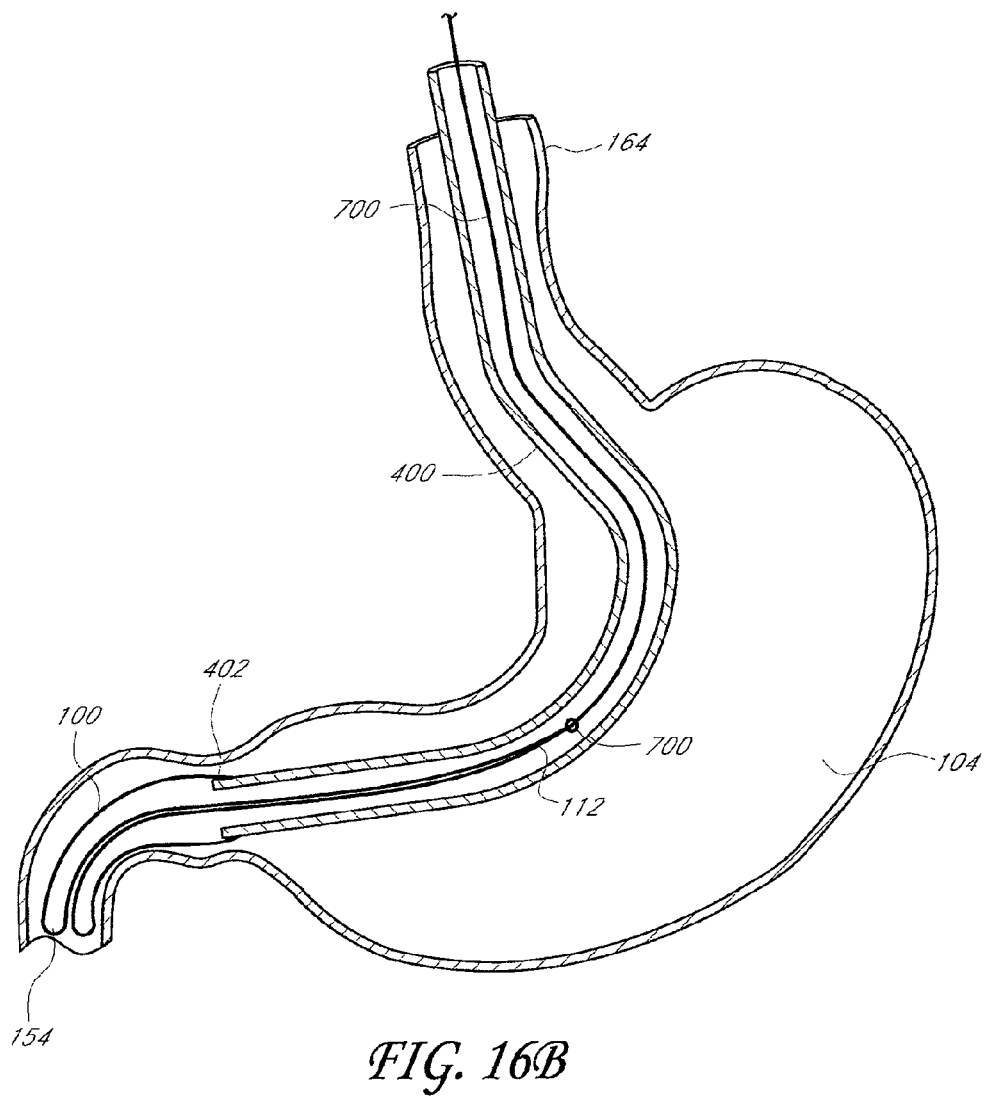

The distal end 112 of the toposcopic sleeve 100, such as at the distal tail members 801 (not shown for clarity) of the sleeve 100 is closed using a grasping element, such as a loop snare 700 previously described. As illustrated in FIG. 16B and as will be apparent in view of the preceding discussion, the loop snare 700 can be manually advanced by a physician to facilitate eversion of the sleeve, concurrently with the introduction of inflation media through filling catheter 400. Use of a loop snare 700 can advantageously reduce the pressure and/or volume of inflation media required as previously described. Using a snare-type device in combination with inflation media as described above can advantageously allow for a lower inflation media pressure, which is the internal sleeve pressure assuming a fluid-tight seal of the distal end of the sleeve.

The loop snare 700 may be removably or permanently connected to any of a wide variety of devices, examples of which have been identified above. As the sleeve 100 is everted distally, the loop snare 700 is also manually advanced distally, pulling the desired diagnostic or therapeutic device (not shown) in a distal direction. In this manner, a device may be distally axially advanced through a tortuous pathway, within the sleeve 100.

After eversion (or axial expansion of the accordion-like sleeve embodiment) has been completed, the snare 700 can be detached from the distal end 112 of the sleeve 100 and then withdrawn. Alternatively, the snare 700 can be left in place to serve as a guidewire. In some embodiments, the snare 700 is configured to fit within an endoscopic working channel. The snare 700 preferably has an axial length that is greater than the length of the sleeve 100 and filling catheter 400.

Use of a grasping member such as a loop snare in connection with the sleeve can be especially advantageous when additional diagnostic or therapeutic items are delivered along with the sleeve. For example, the method described above can be used in connection with capsule endoscopy. In capsule endoscopies, a patient swallows a capsule, and a micro-camera takes thousands of pictures as it travels through the gastrointestinal tract. The camera transmits these images to a special recording device using wireless technology. These images can be transformed into a video, so the physician can see images of the full gastrointestinal tract. However, the specific location within the GI tract in which a particular image is taken cannot be readily determined. Using the disclosed method, a capsule endoscope can be operably attached to either the distal end of the snare or the sleeve. As the total length of the snare as well as the length of the snare positioned within the patient are known, the precise location of the capsule at the time that an image is taken can be advantageously determined. In a similar fashion, other diagnostic or therapeutic modalities such as drug delivery, biopsy, cautery, hemostasis, sclerotherapy, embolization, and the like can be performed at a particular location with greater specificity.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

We claim:

1. A toposcopic deployment system, comprising: a filling catheter; a sleeve having a proximal end and a distal end and configured to be delivered within a body lumen, the sleeve at least partially inverted within the filling catheter, wherein the proximal end of the sleeve is removably connected to the distal end of the filling catheter; wherein the sleeve comprises a plurality of tail elements on its distal end such that the distal end of the sleeve can be closed to promote eversion of the sleeve; and a grasping member configured to be attached to the said tail elements of the sleeve and mechanically promote eversion of the sleeve.

2. The toposcopic deployment system of claim 1, further comprising a pump for infusing inflation media to the filling catheter.

3. The toposcopic deployment system of claim 1, further comprising a source of filling media.

4. The toposcopic deployment system of claim 1, wherein the grasping member comprises a loop snare.

5. The toposcopic deployment system of claim 1, comprising three tail elements spaced substantially equidistant with respect to the circumference of a lumen of the sleeve.

6. The toposcopic deployment system of claim 1, wherein the filling catheter comprises a pushable tube.

7. The toposcopic deployment system of claim 1, wherein the filling catheter is collapsible.

8. The toposcopic deployment system of claim 1, wherein the filling catheter is semi-rigid.

9. The toposcopic deployment system of claim 1, further comprising at least one pull wire operably attached to the filling catheter to steer the filling catheter within a body lumen.

10. The toposcopic deployment system of claim 1, further comprising a guidewire.

11. The toposcopic deployment system of claim 1, further comprising an overtube.

12. The toposcopic deployment system of claim 1, wherein the sleeve is biodegradable.

13. The toposcopic deployment system of claim 1, further comprising a diagnostic or therapeutic device operably connected to the sleeve selected from the group consisting of: endoscopes, guidewires, catheters, tubular bypass conduits, drugs, adhesives, radiopaque contrast media, cameras, lasers, ultrasound transducers, electrodes, LEDs, cryogenic energy sources, balloons, forceps, graspers, electrosurgical instruments, snares, biopsy devices, needles, and rail systems.

* * * * *

UNITED STATES PATENT AND TRADEMARK OFFICE
CERTIFICATE OF CORRECTION

| | | |
|---|---|---|
| PATENT NO. | : 8,118,774 B2 | Page 1 of 1 |
| APPLICATION NO. | : 11/861156 | |
| DATED | : February 21, 2012 | |
| INVENTOR(S) | : Dann et al. | |

It is certified that error appears in the above-identified patent and that said Letters Patent is hereby corrected as shown below:

Title Page, Item (75) Inventor is corrected to read:

-- Mitchell Dann, Wilson, WY (US); Greg Fluet, Jackson, WY (US); James Wright, Carpinteria, CA (US); Cole Chen, Westlake Village, CA (US) --.

Signed and Sealed this
Thirteenth Day of January, 2015

Michelle K. Lee
*Deputy Director of the United States Patent and Trademark Office*